United States Patent
Christofidou-Solomidou

(10) Patent No.: US 10,966,995 B2
(45) Date of Patent: Apr. 6, 2021

(54) USE OF SECOISOLARICIRESINOL DIGLUCOSIDES (SDGS) AND RELATED COMPOUNDS FOR PROTECTION AGAINST RADIATION AND CHEMICAL DAMAGE

(71) Applicant: THE TRUSTEES OF THE UNIVERSITY OF PENNSYLVANIA, Philadelphia, PA (US)

(72) Inventor: Melpo Christofidou-Solomidou, Eagleville, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 0 days.

(21) Appl. No.: 16/678,734

(22) Filed: Nov. 8, 2019

(65) Prior Publication Data
US 2020/0179423 A1    Jun. 11, 2020

Related U.S. Application Data

(63) Continuation of application No. 15/315,349, filed as application No. PCT/US2015/033501 on Jun. 1, 2015.

(60) Provisional application No. 62/101,293, filed on Jan. 8, 2015, provisional application No. 62/005,330, filed on May 30, 2014.

(51) Int. Cl.
| | |
|---|---|
| *A61K 31/7032* | (2006.01) |
| *A61K 31/365* | (2006.01) |
| *A61K 31/05* | (2006.01) |
| *A61K 31/09* | (2006.01) |

(52) U.S. Cl.
CPC .......... *A61K 31/7032* (2013.01); *A61K 31/05* (2013.01); *A61K 31/09* (2013.01); *A61K 31/365* (2013.01)

(58) Field of Classification Search
None
See application file for complete search history.

(56) References Cited

U.S. PATENT DOCUMENTS

2010/0239696 A1*  9/2010  Christofidou-Solomidou .............
                                                A61K 36/55
                                                424/768
2011/0135641 A1   6/2011  Senberg et al.

FOREIGN PATENT DOCUMENTS

WO    WO-2008/147563    12/2008
WO    WO-2014/200964    12/2014

OTHER PUBLICATIONS

Ayella et al., "Cytostatic inhibition of cancer cell growth by lignan secoisolariciresinol diglucoside"—Nutrition Research, Elsevier Inc., Nov. 2010, vol. 30, No. 11, pp. 762-769.
Chen et al., "Flaxseed and Pure Secoisolariciresinol Digulcoside, but Not Flaxseed Hull, Reduce Human Breast Tumor Growth (MCF-7) in Athymic Mice[1,2]"—The Journal of Nutrition Sep. 23, 2009, vol. 139, No. 11, pp. 2061-2066.
Christofidou-Solomidou et al., "Radioprotective Role in Lung of the Flaxseed Lignan Complex Enriched in the Phenolic Secoisolariciresinol Diglucoside (SDG)"—Radiat Res. Dec, 2012; 178(6): pp. 568-580.
Hongyan et al., "Lignans are involved in the antitumor activity of wheat bran in colon cancer SW480 cells"—J. Nutr. (2005) 135: pp. 598-602.
Lee et al., "Dietary Flaxseed Prevents Radiation-Induced Oxidative Lung Damage, Inflammation and Fibrosis in a Mouse Model of Thoracic Radiation Injury"—Cancer Biol & Ther. Jan. 2009; 8(1): 47-53.
Li et al., "Dietary supplementation with secoisolariciresinol diglycoside 9SDG) reduces experimental metastasis of melanoma cells in mice"—Cancer Letters, Jul. 19, 1999, vol. 142, No. 1, pp. 91-96.
Mishra et al., "Novel Synthetic (S,S) and (R,R)-Secoisolariciresinol Digulcosides 9SDGs) Protect Naked Plasmid and Genomic DNA From Gamma Radiation Damage"—Radiation Research (2014), 182(1), pp. 102-110.
Moree et al., "Secoisolariciresinol Diglucoside—A Phytoestrogen Nutraceutical of Flaxseed: Synthesis and Evaluation of Antioxidant Potency"—Free Radicals and Antioxidants, Oct. 1, 2011, vol. 1, No. 4, pp. 31-38.
Pietrofesa et al., "Radiation mitigating properties of the lignan component in flaxseed"—BMC Cancer, Biomed Central, London, GB, Apr. 4, 2013, vol. 13, No. 1, p. 179.
Thompson et al., "Antitumorigenic effect of a mammalian lignan precursor from flaxseed"—Nutrition and Cancer 1996, vol. 26 No. 2, pp. 159-165.
Partial Supplementary EP Search Report dated Dec. 19, 2017 for EP Appln No. 15799095.3.
Mishra et al. " Synthesis and antixoidant evaluation of (s,S)- and (R, R)-secoisolariciresinol diglucosides (SDgs)." Bioorg Med Chem Lett. Aug. 2, 2013 (Aug. 2, 2013), vol. 23, No. 19, pp. 5325-5328. entire document.
Machlin et al. " Free radical tissue damage; protective role of antiocidant nutrients," FASEB J. Dec. 1, 1987 (Dec. 1, 1987), vol. 1, No. 6, pp. 441-445, entire document.
Huang et al. "Natural phenolic compounds from medicinal herbs and dietary plants; potential use for cancer prevention," Nutr Cancer, Dec. 29, 2009 (Dec. 29, 2009), vol. 62, No. 1, pp. 1-20, entire document.

\* cited by examiner

*Primary Examiner* — Traviss C McIntosh, III
(74) *Attorney, Agent, or Firm* — Mark S. Cohen; Pearl Cohen Zedek Latzer Baratz, LLP

(57) ABSTRACT

The invention provides compositions and methods for radioprotection and chemoprevention using therapeutic and prophylactics methods of using (S,S)-SDG (R,R)-SDG, (S,R)-SDG (R,S)-SDG, SDG, SECO, EL, ED, analogs thereof, stereoisomers thereof and other related molecules.

9 Claims, 60 Drawing Sheets

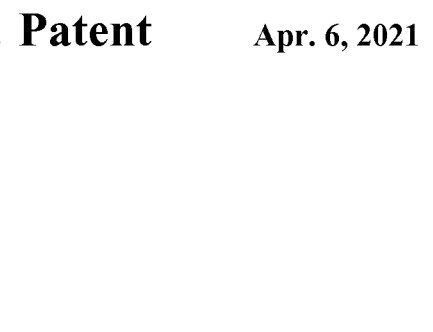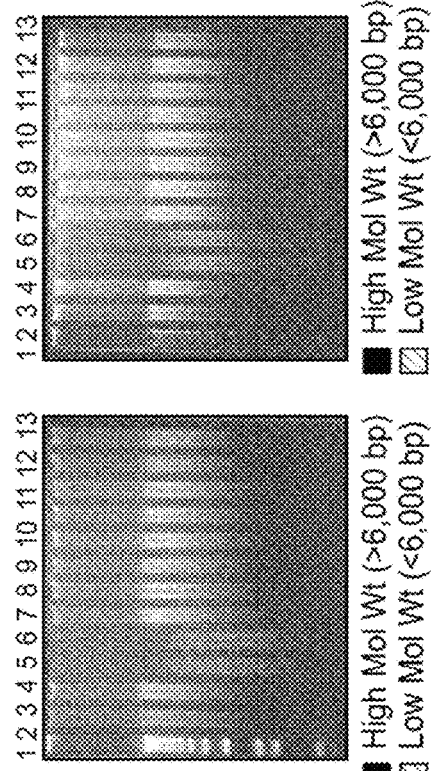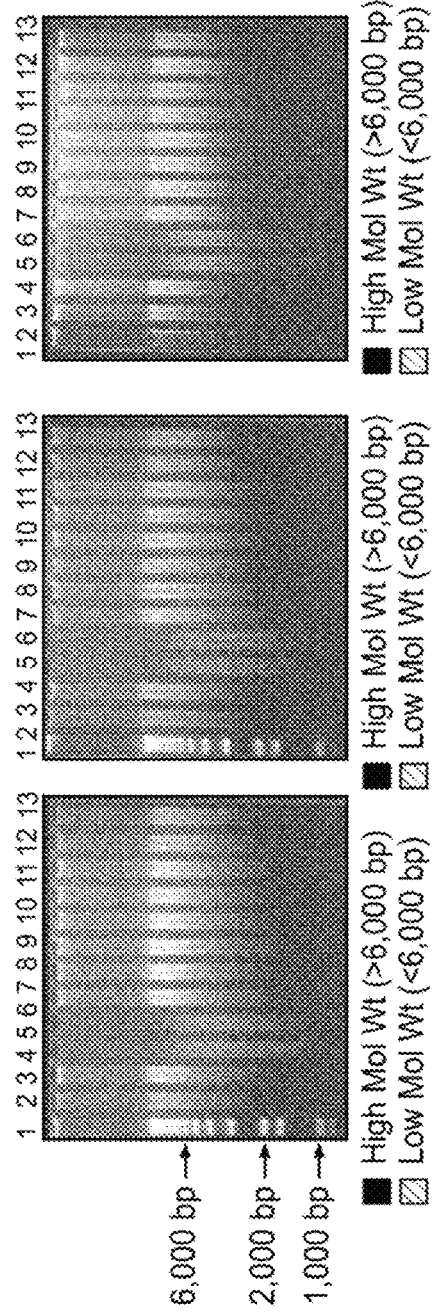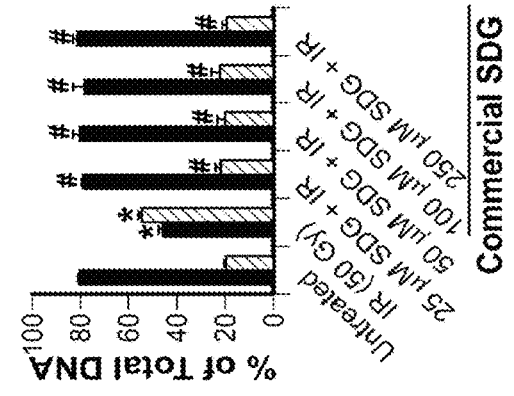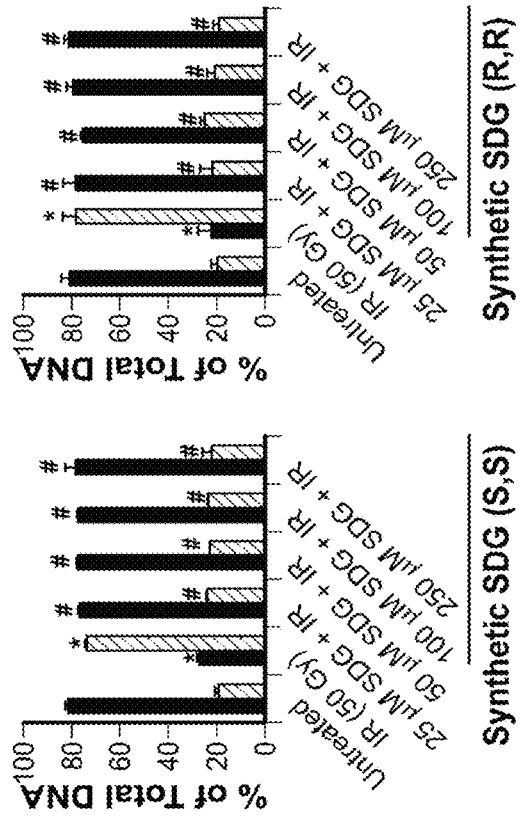

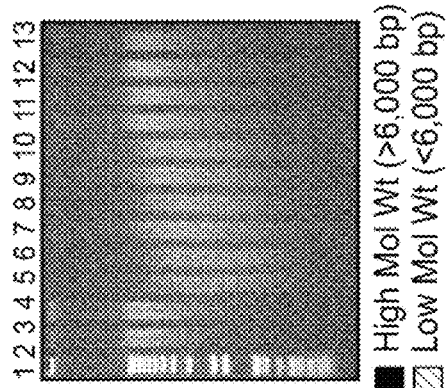
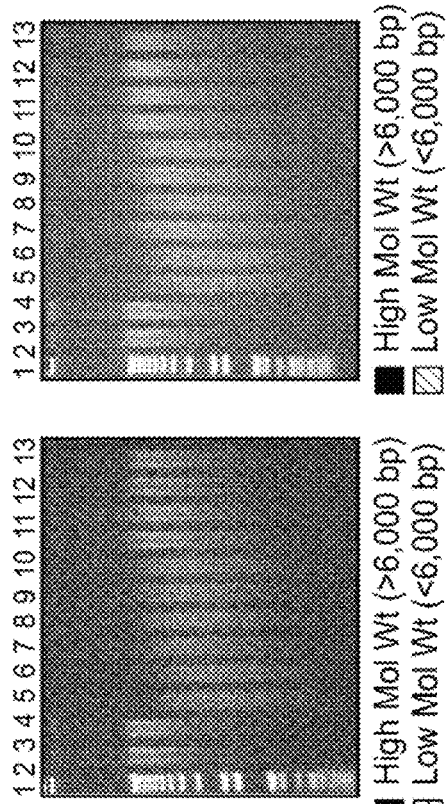
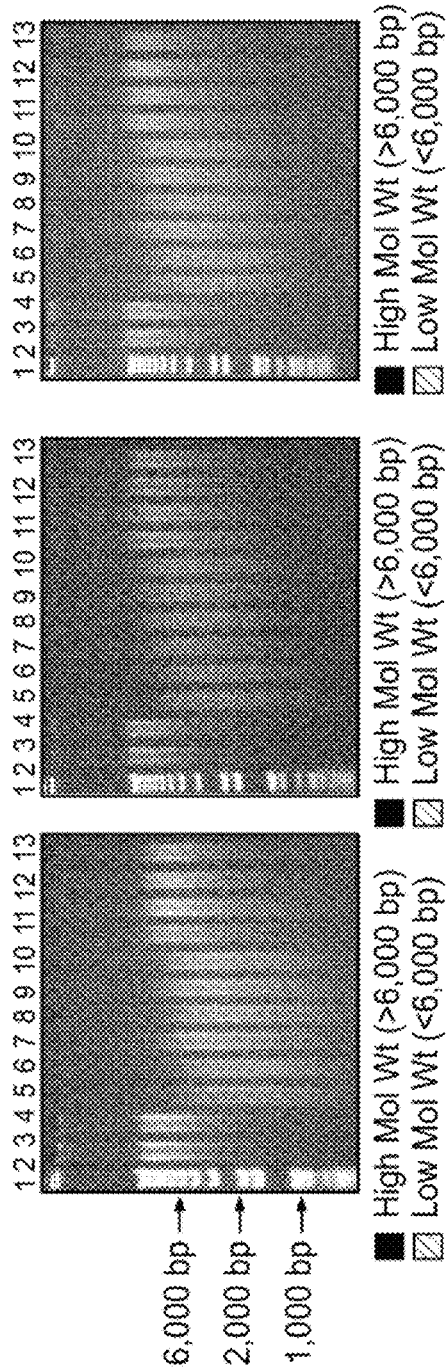
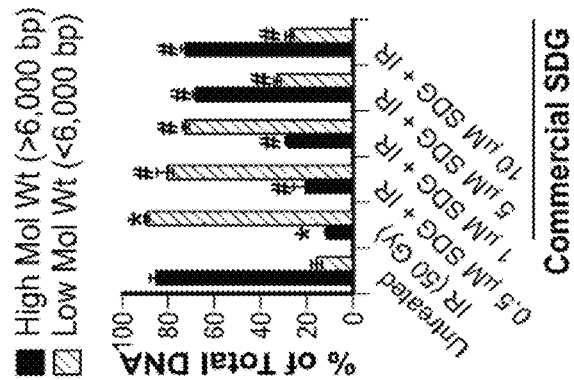
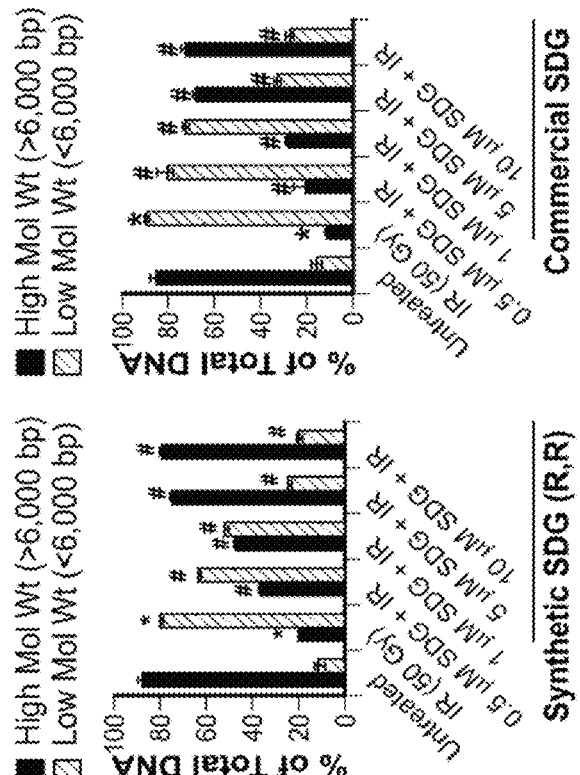
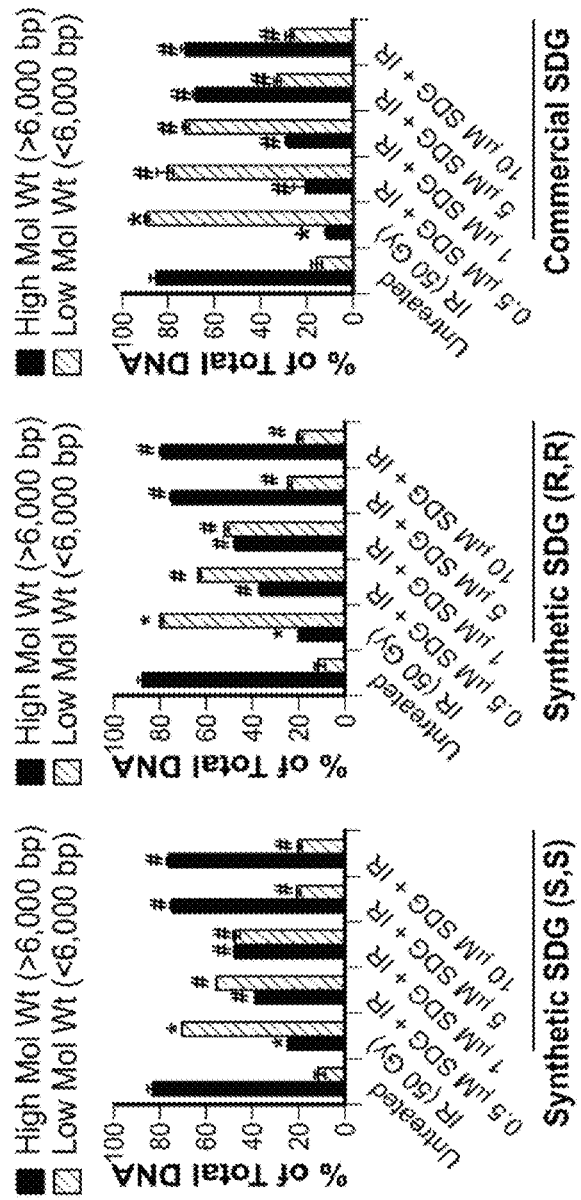

Epithelial Cells

Endothelial Cells

WT Fibroblasts

Epithelial Cells

Endothelial Cells

WT Fibroblasts

Epithelial Cells

Endothelial Cells

WT Fibroblasts

Epithelial Cells

Endothelial Cells

WT Fibroblasts

Figure 29
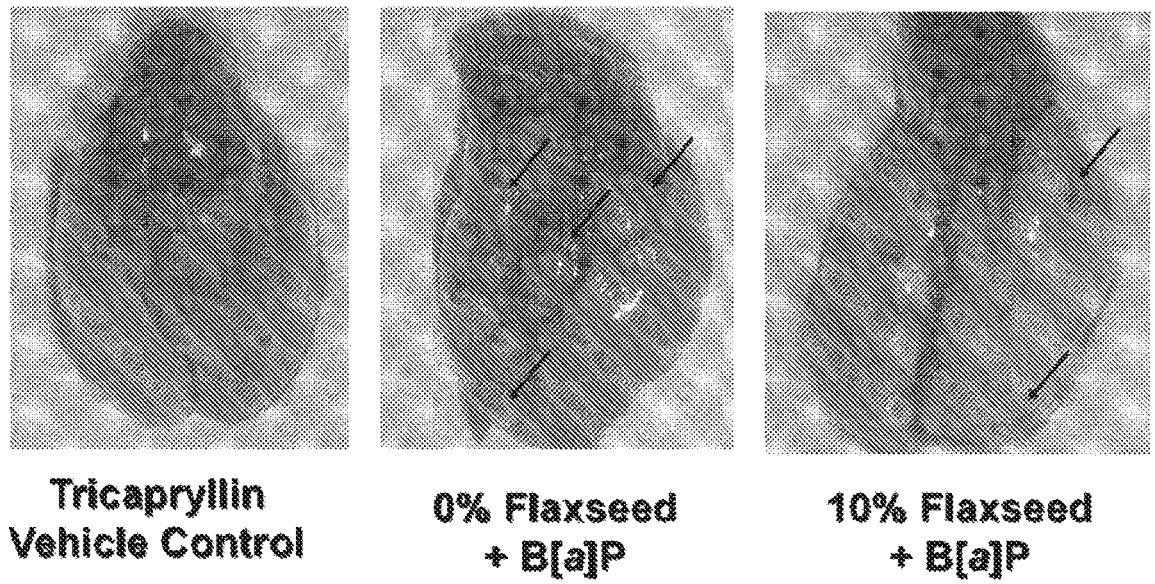
Tricapryllin Vehicle Control     0% Flaxseed + B[a]P     10% Flaxseed + B[a]P
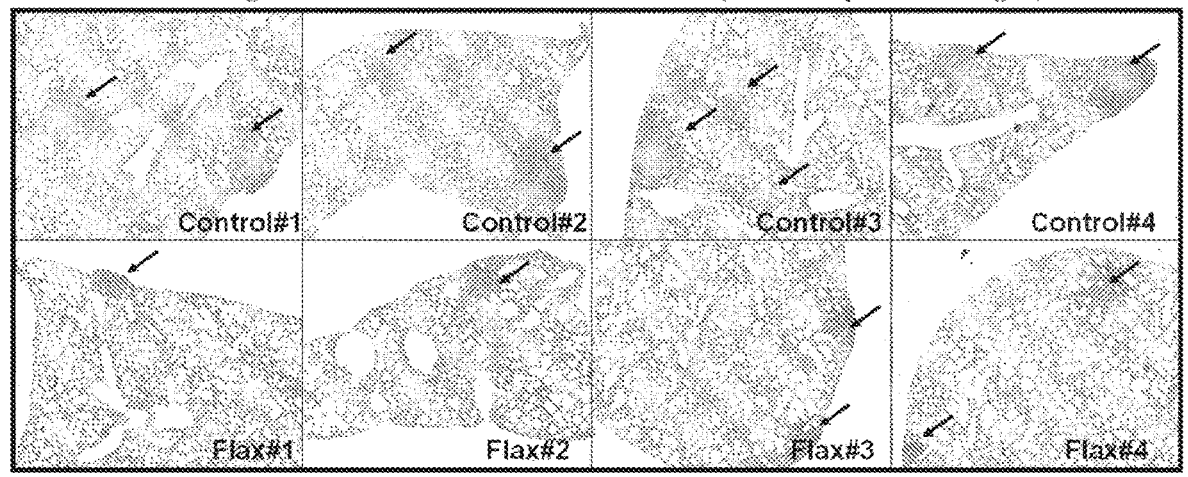
Figure 30

Figure 35
Sustained systemic metabolite levels following daily flaxseed or flaxseed-lignan ingestion
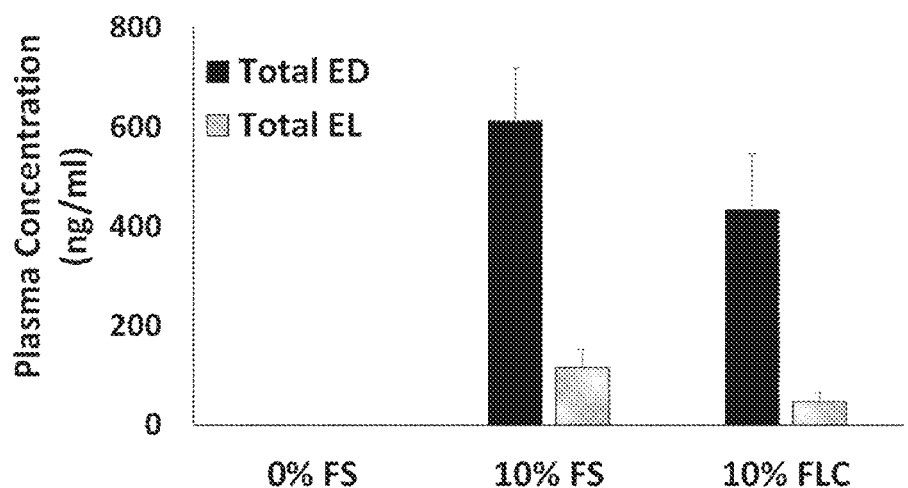
Flaxseed (FS) and Flaxseed Lignan Component (FLC) Prevent Asbestos-induced Abdominal Inflammation
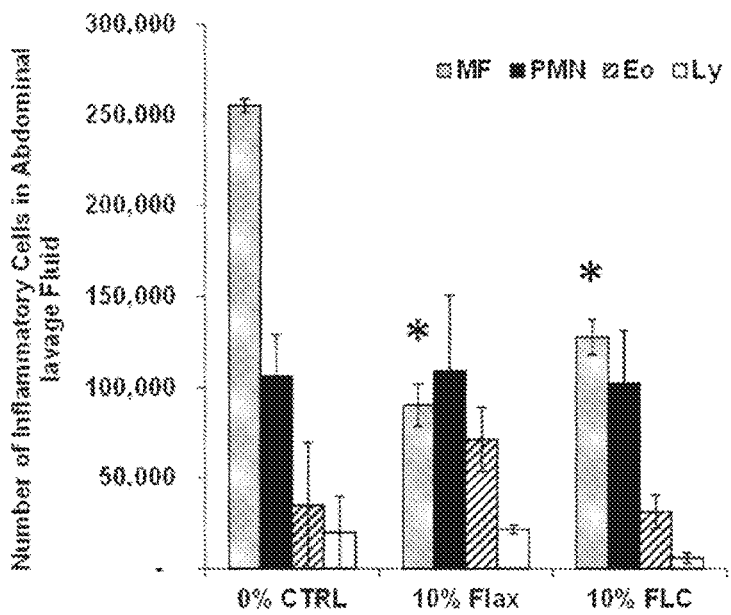
Figure 36

Flaxseed and FLC Prevent pro-inflammatory Cytokine Secretion Induced by Asbestos in Mice Figure 42B
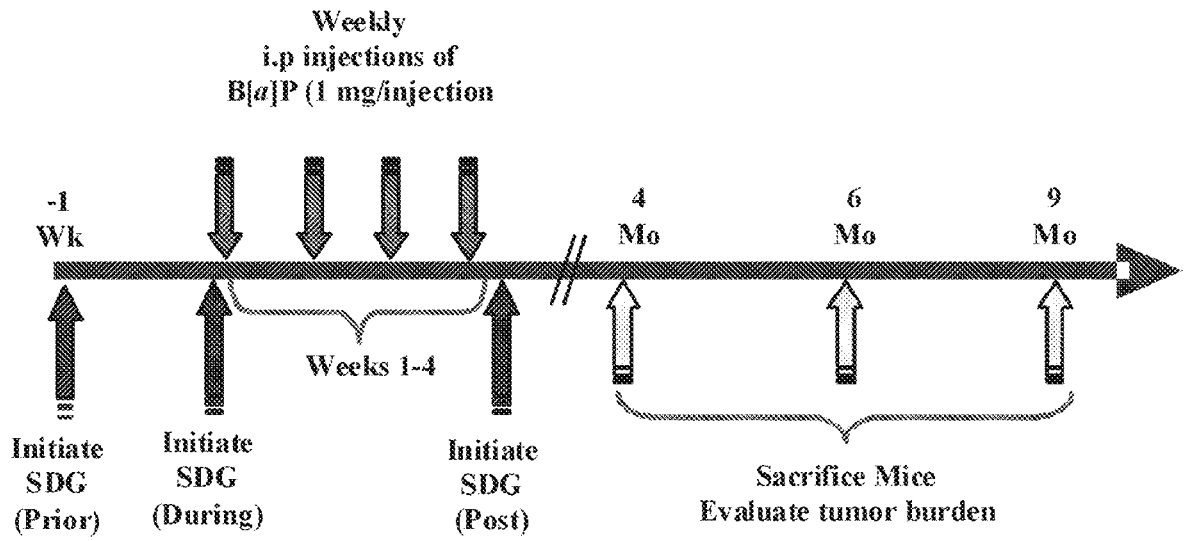
Experimental Study: Cross-Over Design
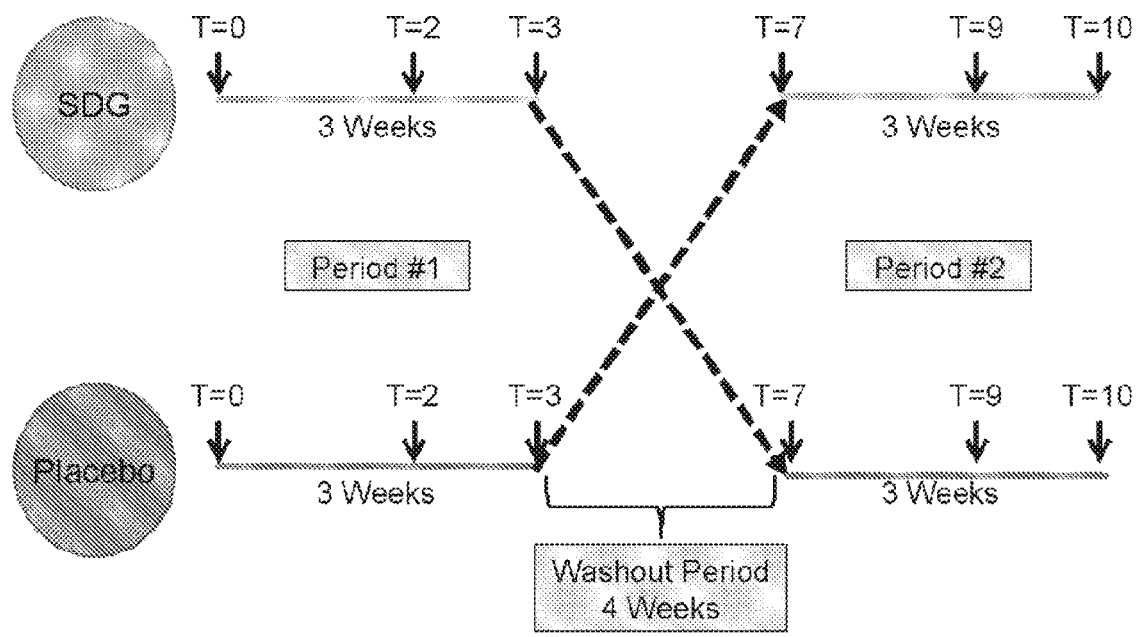
↓ Indicates collection time point of oral epithelium (obtain by a mouth swab), urine, blood, and exhaled breath condensate (EBC)
Figure 43

Figure 44
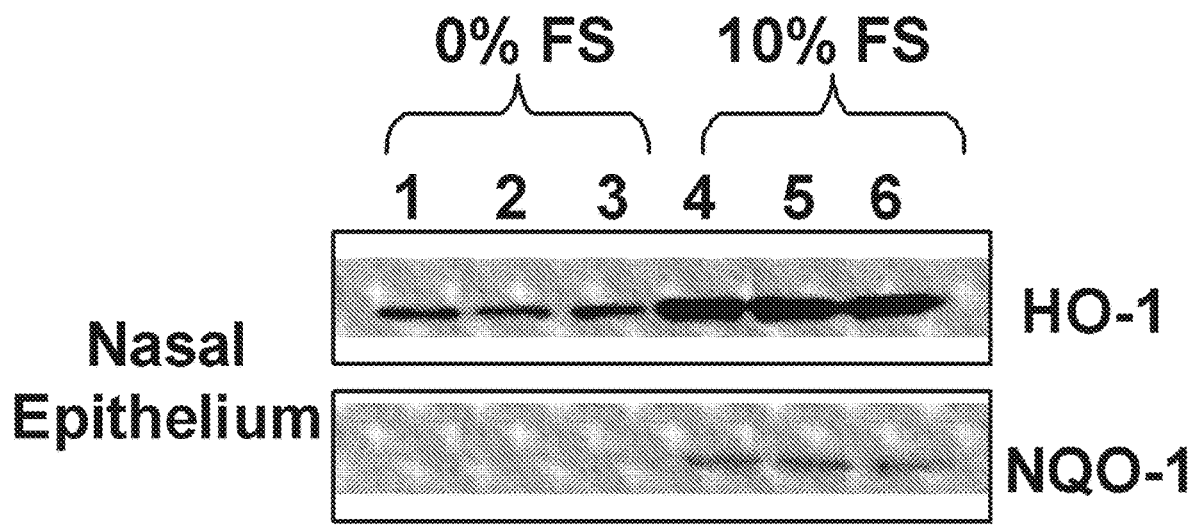
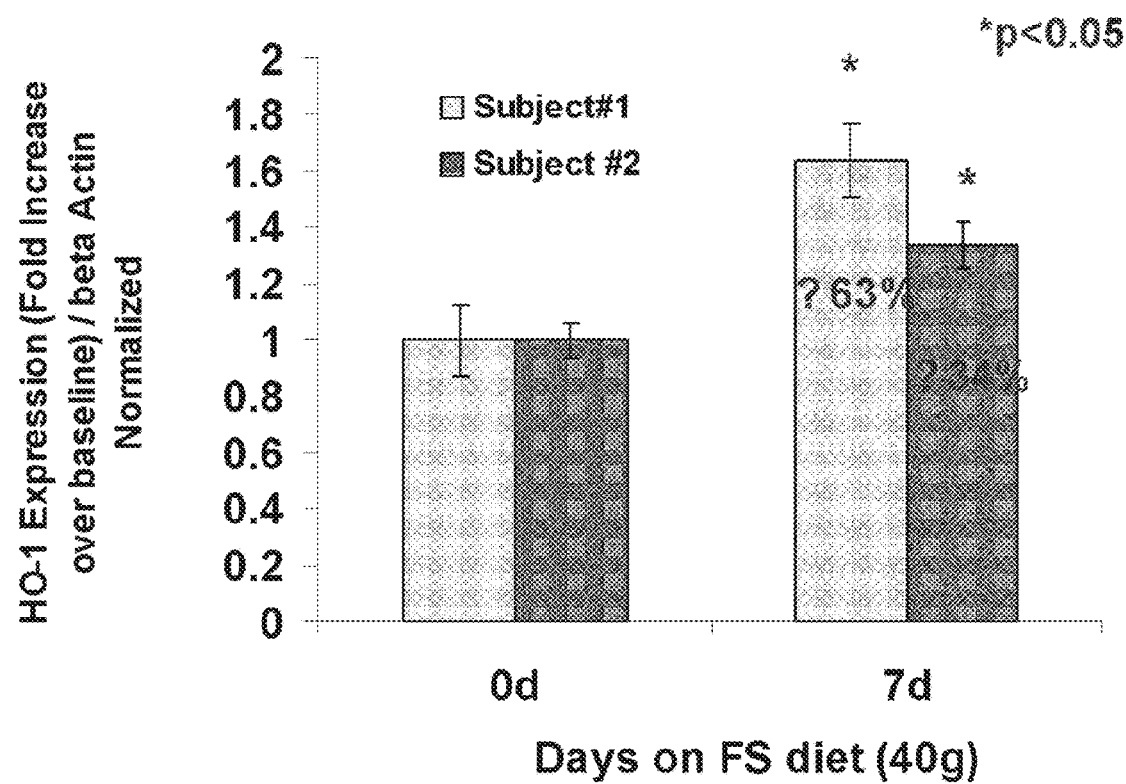
Figure 45

Figure 48
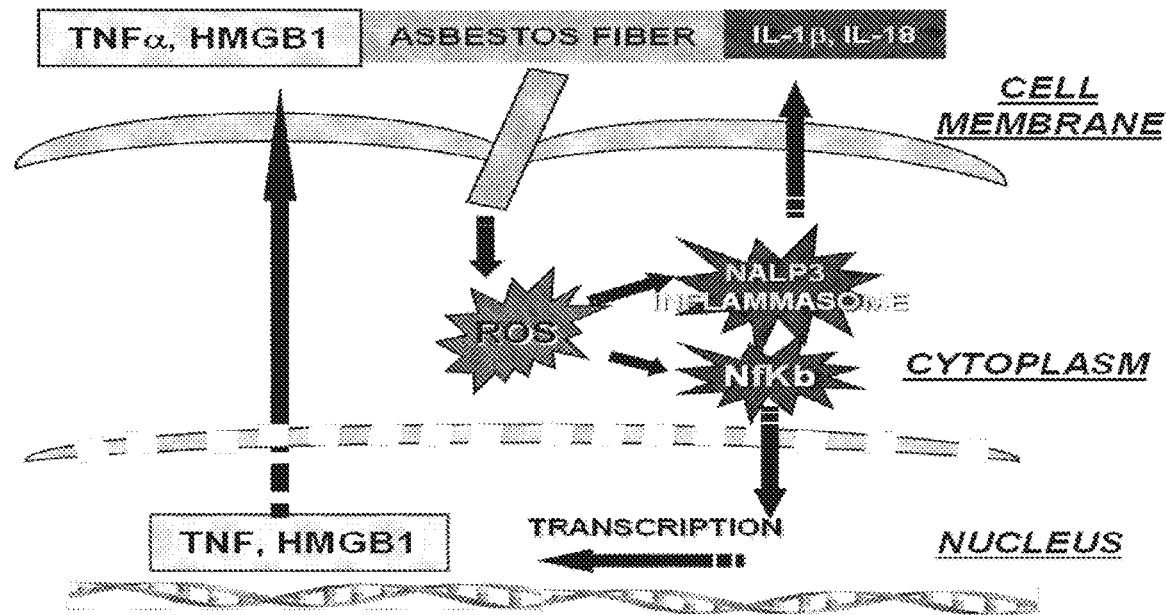
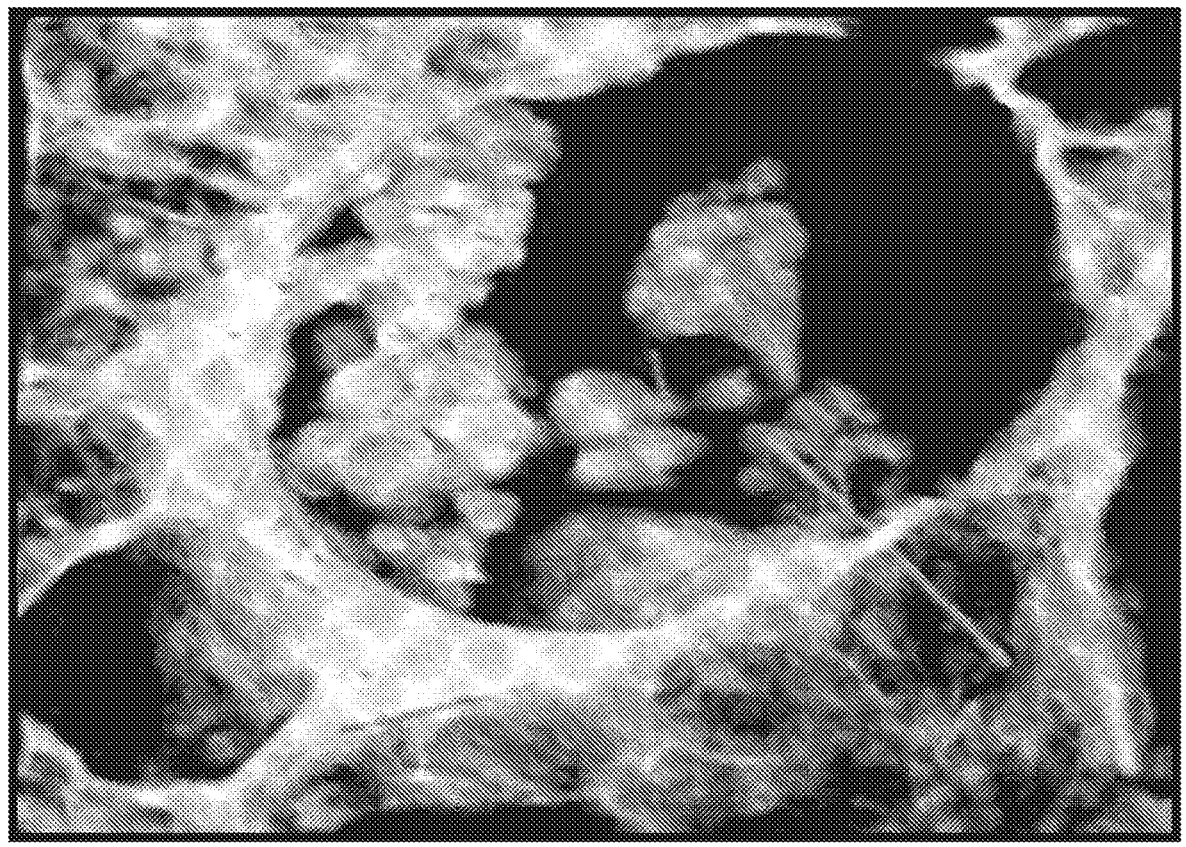

Figure 51
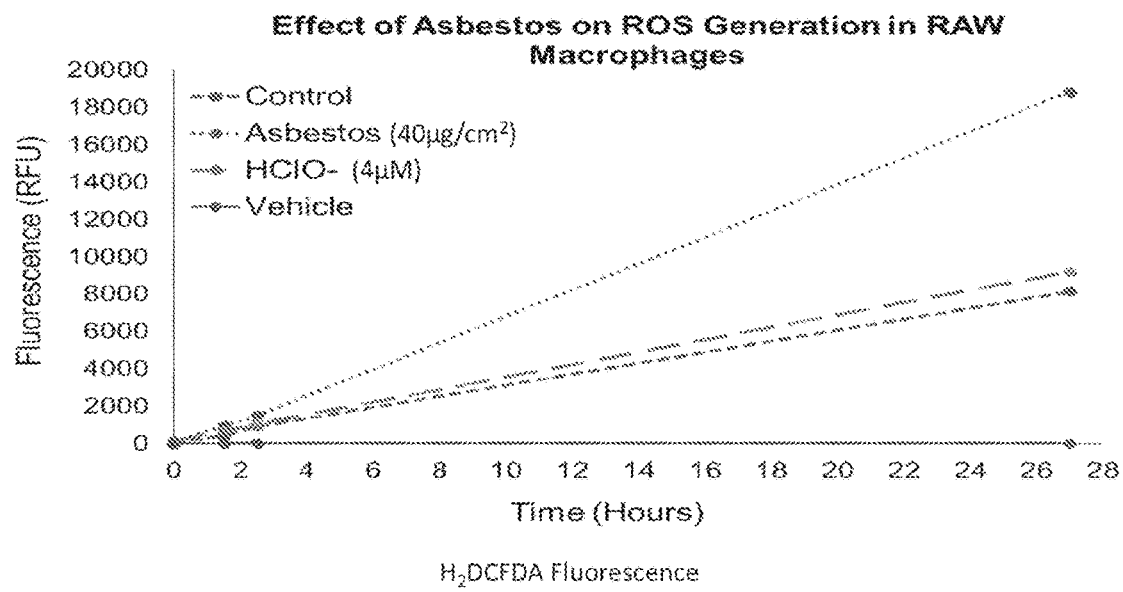
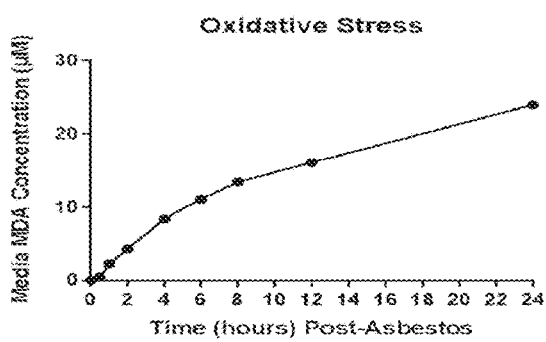
Figure 52A
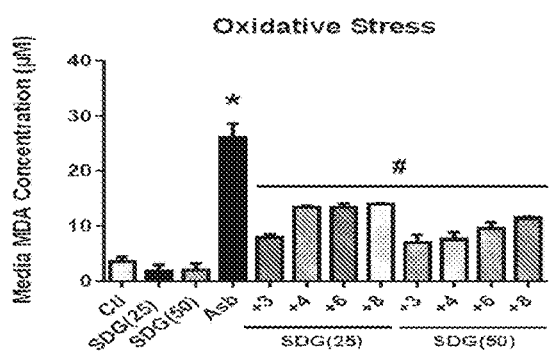
Figure 52B

Nitrosative Stress

IL-1β

TNFα

USE OF SECOISOLARICIRESINOL DIGLUCOSIDES (SDGS) AND RELATED COMPOUNDS FOR PROTECTION AGAINST RADIATION AND CHEMICAL DAMAGE

CROSS-REFERENCE TO RELATED APPLICATIONS

This application is a continuation of U.S. patent application Ser. No. 15/315,349, filed on Nov. 30, 2016, which is a National Phase Application of PCT International Application PCT/US15/33501, filed Jun. 1, 2015, claiming priority to U.S. Provisional Patent Applications 62/101,293, filed Jan. 8, 2015 and 62/005,330, filed May 30, 2014. Each of the above-identified applications is incorporated by reference herein in its entirety.

GOVERNMENT INTEREST

This invention was made with government support under Grant Numbers CA133470, ES013508, AI081251, ES023720, CA180548 and CA016520 awarded by the National Institutes of Health. The government has certain rights in the invention.

FIELD OF THE INVENTION

Provided herein are compositions and methods for radioprotection and radiation mitigation and for chemoprevention, such as from carcinogen-induced lung cancer and mesothelioma or from hypochlorite ions, using secoisolariciresinol diglucoside (SDG), secoisolariciresinol (SECO), enterodiol (ED), enterolactone (EL), stereoisomers thereof, metabolites thereof, and analogs thereof.

BACKGROUND OF THE INVENTION

Ionizing radiation produces a wide range of deleterious effects in living organisms. Humans are exposed to radiation as an occupational hazard, during diagnostic and therapeutic radiographic procedures, when using electronic devices, from background radiation of nuclear accidents, during air and space travel, as well as from prolonged exposure to the sun (e.g., sun bathers or outdoor workers). Exposure to natural radiation can occur in many forms: natural resources such as air, water, and soil may become contaminated when they come in contact with naturally-occurring, radiation-emitting substances (radionuclides); radon is one such common source of natural radiation. Current global developments have additionally established terrorism as a dangerous means by which potentially large numbers of people can be exposed to lethal amounts of radiation. It is, therefore, of high importance to identify agents that can be administered before and during exposure to radiation (i.e., radioprotective agents), and as treatment after radioactive exposure (i.e., radiation mitigators).

In addition, lung cancer is the leading cause of cancer mortality in the United States. Despite novel targeted therapeutic agents, improved staging and surgical techniques, and increased utilization of concomitant chemoradiation therapy for locally advanced lung cancer there has only been a minimal decrease of overall mortality rates (Tan & Spivack (2009) *Lung Cancer* 65:129-137). Cancer chemoprevention has been defined as the use of dietary and pharmacological intervention with specific natural or synthetic agents designed to prevent, suppress, or reverse the process of carcinogenesis before the development of malignancy (Hong & Sporn, (1997). *Science* 278:1073-1077). One strategy for lung cancer chemoprevention focuses on the use of agents that modulate the metabolism and disposition of tobacco, environmental and other carcinogens through upregulation of detoxifying phase II enzymes. Many synthetic and naturally occurring compounds are known to induce the expression of phase II enzymes. There have been numerous reports that support the idea that Nrf2/ARE-regulated phase II enzyme induction is a highly effective strategy for reducing susceptibility to carcinogens. We have data to show that flaxseed (FS) and its main lignan SDG, both from enrichment of the natural material and synthetically derived, are effective lung cancer chemoprevention agents in a mouse model of chemical carcinogen-induced lung cancer.

Approximately 85% of lung cancer is caused by smoking. Major lung carcinogens in tobacco smoke are polycyclic aromatic hydrocarbons, typified by benzo[a]pyrene (BaP). Until better treatments are developed, the best hope for decreasing deaths will be prevention through screening, smoking cessation, or chemoprevention. Chemopreventive agents must be given for prolonged periods of time in large numbers of exposed, but relatively healthy subjects. They must be safe, non-toxic, palatable, and ideally, affordable. A number of chemopreventive agents have been studied in lung cancer, however none have met these criteria. One of the most promising approaches is upregulation of Phase II anti-oxidant and detoxifying enzymes. Unfortunately, the Phase II enzyme activators tested in patients to date, such as Oltipraz or Sulforophane, have proven to be unacceptably toxic (Pendyala et al. (2001). *Cancer Epidemiol Biomarkers Prev* 10:269-272.). Safe, non-toxic chemopreventive agents that are effective in preventing the oxidative stress and the DNA damage induced by lung carcinogens in tobacco smoke are thus desperately needed.

Another well-known environmental carcinogen is asbestos, which refers to a group of naturally occurring hydrated fibrous silicate fibers used commercially for insulation. It has now been clearly established in both animal models and in patients that asbestos fiber inhalation can lead to neoplastic diseases such as malignant mesothelioma (MM) and lung cancer (Carbone & Yang (2012). *Clin Cancer Res* 18:598-604; Neri et al. (2012). *Anticancer Res* 32:1005-1013), as well as pulmonary fibrosis. MM is a highly aggressive cancer that arises from the mesothelial cells of the pleura and peritoneum with a median survival of about 1 year (Sterman et al. (2005). Clin Cancer Res 11, 7444-7453; Sterman et al. (1999). Chest 116, 504-520; Benard et al. (1999). J Nucl Med 40, 1241-1245). Current therapies, other than surgery in very early disease, are not curative (Sterman & Albelda (2005). Respirology 10, 266-283.). Presently, MM causes about 3,000 deaths per year in the US and an additional 5,000 deaths/year in Western Europe.

Although asbestos use has been restricted in many western countries, it is still used in many countries around the world and it is estimated that more than 2 million tons were mined in 2008 (Survey, B. G. (2010). World Mineral Production 2004-08. Nottingham, UK, British Geological Survey). There will thus likely be a dramatic increase in MM cases in the third world (especially in India) where the use of asbestos has increased with few precautions taken. However, even in the developed world, important exposures still exist. These include many types of occupations that expose workers to pre-existing asbestos (i.e. plumbers, pipefitters, insulators, insulation removal, etc.) as well as superfund asbestos hazardous waste sites. There are also environmental and domestic exposures. For example, there is an increased risk of MM in areas where mining or asbestos factories have closed.

A major issue in the link between asbestos and cancer is that inhaled asbestos fibers can persist in the lung for very long periods of time resulting in continuous damage, even if the patient is removed from the exposure. Because of this long latency period (often up to 30-50 years), individuals exposed in the past remain at increased risk of MM and other cancers throughout their lives.

Chemoprevention of cancer aims to prevent, arrest, or reverse either the initiation phase of carcinogenesis or the progression of neoplastic cells to cancer. Although this definition sounds simple, it has been very difficult to find effective chemopreventive agents. First, the mechanisms by which carcinogens induce cancer usually involve multiple mechanisms, making efficacy challenging and requiring an agent with multiple activities. Second, since the agent will be used to prevent a small number of tumors in a large population of healthy, but at-risk individuals, it must be extraordinarily non-toxic, well-tolerated, and affordable.

It is, therefore, also of high importance to identify agents (i.e., chemopreventive agents) that can be administered before, during, and exposure to carcinogens or other harmful chemical agents, such as chemical warfare agents, chlorine and hypochlorite ions and other harmful toxicants.

SUMMARY OF THE INVENTION

In one aspect, the invention relates to a method for protecting a biomolecule (such as genetic material like a nucleic acid, a protein or a lipid), a cell, or a tissue, from radiation damage in a subject in need thereof, the method comprising: administering to said subject an effective amount of flaxseed, its bioactive ingredient, degradant or a metabolite thereof. Administration to said subjects encompasses administration prior to, during and after exposure to damaging radiation exposure. The time prior, during and post could be seconds, minutes, hours, days, weeks, months or even years. The bioactive ingredient encompasses secoisolariciresinol diglucoside (SDG), secoisolariciresinol (SECO), enterodiol (ED), enterolactone (EL), analogs thereof, stereoisomers thereof, or a combination thereof.

In another aspect, the invention relates to a method for treating or preventing radiation damage in a subject who has been or will be exposed to radiation, the method comprising: administering to said subject an effective amount of at least one bioactive ingredient, wherein said bioactive ingredient comprises secoisolariciresinol diglucoside (SDG), secoisolariciresinol (SECO), enterodiol (ED), enterolactone (EL), analogs thereof, stereoisomers thereof, or a combination thereof.

In another aspect, the invention relates to a method for protecting biomolecule (such as genetic material like a nucleic acid, a protein or a lipid), a cell, or a tissue, from radiation damage resulting from accidental radiation exposure in a subject in need thereof, the method comprising: administering to said subject an effective amount of flaxseed, its bioactive ingredient, degradant or a metabolite thereof.

In another aspect, the invention relates to a method for protecting biomolecule (such as genetic material like a nucleic acid, a protein or a lipid), a cell, or a tissue, from radiation damage resulting in aging.

In another aspect, the invention relates to a method for protecting a biomolecule (such as genetic material like a nucleic acid, a protein or a lipid), a cell, or a tissue from damage resulting from exposure to chemical carcinogens and toxicants both natural and synthetic.

In another aspect, the invention relates to a method for protecting a biomolecule (such as genetic material like a nucleic acid, a protein or a lipid), a cell, or a tissue, from radiation damage resulting from radiation therapy for cancer treatment in a subject in need thereof, the method comprising: administering to said subject an effective amount of flaxseed, its bioactive ingredient, degradant or a metabolite thereof.

In another aspect, the invention relates to a method for protecting a biomolecule (such as genetic material like a nucleic acid, a protein or a lipid), a cell, or a tissue from radiation damage in a subject in need thereof, the method comprising: administering to said subject an effective amount of at least one bioactive ingredient, wherein said bioactive ingredient comprises secoisolariciresinol diglucoside (SDG), secoisolariciresinol (SECO), enterodiol (ED), enterolactone (EL), analogs thereof, stereoisomers thereof, or a combination thereof. In some embodiments, the radiation damage results from accidental radiation exposure. In some embodiments, the radiation damage results from radiation therapy for cancer (e.g., lung cancer) treatment.

In another aspect, the invention relates to a method for preventing radiation induced damage to a biomolecule (such as genetic material like a nucleic acid, a protein or a lipid), a cell, or a tissue, in a subject in need thereof, the method comprising: administering to said subject an effective amount of flaxseed, its bioactive ingredient, or a metabolite thereof.

In another aspect, the invention relates to a method for preventing radiation induced damage to a biomolecule (such as genetic material like a nucleic acid, a protein or a lipid), a cell, or a tissue, in a subject in need thereof, the method comprising: administering to said subject an effective amount of at least one bioactive ingredient, wherein said bioactive ingredient comprises secoisolariciresinol diglucoside (SDG), secoisolariciresinol (SECO), enterodiol (ED), enterolactone (EL), analogs thereof, stereoisomers thereof, or a combination thereof.

In another aspect, the invention relates to a method for protecting a biomolecule (such as genetic material like a nucleic acid, a protein or a lipid), a cell, or a tissue, from radiation damage in a cell, the method comprising contacting said cell with an effective amount of at least one bioactive ingredient, wherein said bioactive ingredient comprises secoisolariciresinol diglucoside (SDG), secoisolariciresinol (SECO), enterodiol (ED), enterolactone (EL), analogs thereof, stereoisomers thereof, or a combination thereof.

In another aspect, the invention relates to a method for protecting a biomolecule (such as genetic material like a nucleic acid, a protein or a lipid), a cell, or a tissue, from carcinogen damage in a subject in need thereof, the method comprising: administering to said subject an effective amount of flaxseed, its bioactive ingredient, degradant or a metabolite thereof. Administration to said subjects encompasses administration prior to, during and after exposure to damaging exposure to chemical carcinogens and toxicants both natural and synthetic. The time prior, during and post could be seconds, minutes, hours, days, weeks, months or even years. The bioactive ingredient encompasses secoisolariciresinol diglucoside (SDG), secoisolariciresinol (SECO), enterodiol (ED), enterolactone (EL), analogs thereof, stereoisomers thereof, or a combination thereof.

In another aspect, the invention relates to a method for protecting a biomolecule, from carcinogen damage resulting from accidental exposure to chemical carcinogens and toxicants both natural and synthetic in a subject in need thereof, the method comprising: administering to said subject an effective amount of flaxseed, its bioactive ingredient, degradant or a metabolite thereof.

In another aspect, the invention relates to a method for protecting a biomolecule (such as genetic material like a nucleic acid, a protein or a lipid), a cell, or a tissue, from damage from chemical carcinogens and toxicants both natural and synthetic resulting in lung cancer or mesothelioma.

In another aspect, the invention relates to a method for protecting a biomolecule (such as genetic material like a nucleic acid, a protein or a lipid), a cell, or a tissue, from carcinogen damage, the method comprising: contacting said biomolecule, cell, or tissue with an effective amount of a bioactive ingredient. Contact with said biomolecule, cell, or tissue encompasses contact prior to, during and after exposure to damaging exposure to chemical carcinogens and toxicants both natural and synthetic. The time prior, during and post could be seconds, minutes, hours, days, weeks, months or even years. The bioactive ingredient encompasses secoisolariciresinol diglucoside (SDG), secoisolariciresinol (SECO), enterodiol (ED), enterolactone (EL), analogs thereof, stereoisomers thereof, or a combination thereof.

In another aspect, the invention relates to a method for treating or preventing carcinogen-induced damage, malignant transformation or cancer development in subject who has been or will be exposed to one or more carcinogens from carcinogen-induced cancer, the method comprising: administering to said subject an effective amount of at least one bioactive ingredient, wherein said bioactive ingredient comprises secoisolariciresinol diglucoside (SDG), secoisolariciresinol (SECO), enterodiol (ED), enterolactone (EL), analogs thereof, stereoisomers thereof, or a combination thereof.

In another aspect, the invention relates to a method for protecting a subject exposed to one or more carcinogens from a carcinogen-induced cancer, the method comprising: administering to said subject an effective amount of flaxseed, its bioactive ingredient, or a metabolite thereof.

In another aspect, the invention relates to a method for protecting a biomolecule (such as genetic material like a nucleic acid, a protein or a lipid), a cell, or a tissue, from damage by hypochlorite ions in a subject in need thereof, the method comprising: administering to said subject an effective amount of flaxseed, its bioactive ingredient, degradant or a metabolite thereof. Administration to said subjects encompasses administration prior to, during and after exposure to damaging exposure to chemical carcinogens and toxicants both natural and synthetic. The time prior, during and post could be seconds, minutes, hours, days, weeks, months or even years. The bioactive ingredient encompasses secoisolariciresinol diglucoside (SDG), secoisolariciresinol (SECO), enterodiol (ED), enterolactone (EL), analogs thereof, stereoisomers thereof, or a combination thereof.

In another aspect, the invention relates to a method for treating or preventing hypochlorite ion-induced damage in a subject who has been or will be exposed to hypochlorite ions, the method comprising: administering to said subject an effective amount of at least one bioactive ingredient, wherein said bioactive ingredient comprises secoisolariciresinol diglucoside (SDG), secoisolariciresinol (SECO), enterodiol (ED), enterolactone (EL), analogs thereof, stereoisomers thereof, or a combination thereof.

In another aspect, the invention relates to a method for protecting a biomolecule (such as genetic material like a nucleic acid, a protein or a lipid), a cell, or a tissue, from damage by hypochlorite ions, the method comprising: contacting said biomolecule, cell, or tissue exposed to or to be exposed to hypochlorite ions with an effective amount of a bioactive ingredient. Contact with said biomolecule, cell, or tissue encompasses contact prior to, during and after exposure to damaging exposure to chemical carcinogens and toxicants both natural and synthetic. The time prior, during and post could be seconds, minutes, hours, days, weeks, months or even years. The bioactive ingredient encompasses secoisolariciresinol diglucoside (SDG), secoisolariciresinol (SECO), enterodiol (ED), enterolactone (EL), analogs thereof, stereoisomers thereof, or a combination thereof.

In another aspect, the invention relates to a composition for use in one of the foregoing methods.

Unless otherwise defined, all technical and scientific terms used herein have the same meaning as commonly understood by one of ordinary skill in the art to which this invention belongs. Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description. It is also contemplated that whenever appropriate, any embodiment of the present invention can be combined with one or more other embodiments of the present invention, even though the embodiments are described under different aspects of the present invention.

BRIEF DESCRIPTION OF THE DRAWINGS

(FIG. 1A)—The super coiled (SC) form is the lower prominent band (at 3,000 bps) while the open coiled (OC) form is the upper prominent band. Lane 1—1 kb DNA standard ladder, lanes 2 and 3—untreated plasmid DNA, lanes 4 and 5—plasmid DNA exposed to 10 Gy, lanes 6 and 7—plasmid DNA exposed to 25 Gy, and lanes 8 and 9—plasmid DNA exposed to 50 Gy. (FIG. 1B)—SC and OC forms are presented as percent of total plasmid DNA. For each condition, all samples were run in duplicates. The data is presented as mean±standard deviation. $P<0.05$ was considered significant. * and ** show the significant difference as compared to untreated SC and OC forms, respectively.

(FIG. 3A) Lane 1—1 kb DNA standard ladder, lanes 2 and 3—untreated calf thymus DNA, lanes 4 and 5—DNA exposed to 25 Gy, and lanes 6 and 7—DNA exposed to 50 Gy. (FIG. 3B)—High and Low molecular wt DNA forms are presented as percent of total DNA. For each condition, all samples were run in duplicates. The data is presented as mean±standard deviation. P<0.05 was considered significant. * show the significant difference as compared to the untreated forms, respectively.

FIGS. 4A-4F: Effect of increasing concentration of synthetic SDG (S,S), SDG (R,R) and commercial SDG on γ radiation-induced calf thymus DNA fragmentation. All samples were exposed to a γ radiation dose of 50 Gray. SDGs concentrations were 25, 50, 100 and 250 µM. In FIGS. (4A), (4C), and (4E)—representative agarose gel scans of calf thymus DNA after exposure to 50 Gy in the presence of 25, 50, 100 and 250 µM SDG (S,S), SDG (R,R) and SDG (commercial) are shown. Lane 1—1 kb DNA standard ladder, lanes 2 and 3—untreated DNA, lanes 4 and 5-25 µM, lanes 6 and 7-50 µM, lanes 8 and 9-100 µM, and lanes 10 and 11-250 µM SDGs. In FIGS. (4B), (4D) and (4F)—High and Low molecular wt DNA forms are presented as percent of total DNA. For each condition, all samples were run in duplicates. The data is presented as mean±standard deviation. P<0.05 was considered significant. * shows the significant difference as compared to untreated DNA. # shows the significant difference as compared to samples exposed to 50 Gy without SDGs.

FIGS. 5A-5F: Effect of very low concentrations of synthetic SDG (S,S), SDG (R,R) and commercial SDG on γ radiation-induced calf thymus DNA fragmentation. All samples were exposed to a γ radiation dose of 50 Gy. SDGs concentrations were 0.5, 1.0, 5.0 and 10 µM. In FIGS. (5A), (5C), and (5E)—representative agarose gel scans of calf thymus DNA after exposure to 50 Gy in the presence of 0.5, 1.0, 5.0 and 10 µM SDG (S,S), SDG (R,R) and SDG (commercial) are shown. Lane 1—1 kb DNA standard ladder, lanes 2 and 3—untreated DNA, lanes 4 and 5—0.5 µM, lanes 6 and 7—1.0 µM, lanes 8 and 9-5.0 µM, and lanes 10 and 11-10 µM SDGs. In FIGS. (5B) (5D) and (5F)—High and Low molecular wt DNA forms are presented as percent of total DNA. For each condition, all samples were run in duplicates. The data is presented as mean±standard deviation. P<0.05 was considered significant. * shows the significant difference as compared to untreated DNA. # shows the significant difference as compared to samples exposed to 50 Gy without SDGs.

(FIG. 6A) representative agarose gel scans of calf thymus DNA after exposure to 50 Gy in the presence of 10 µM SDG, SECO, ED and EL are shown. Lane 1—1 kb DNA standard ladder, lanes 2 and 3—untreated DNA, lanes 4, 5 and 6—IR 50 Gy, lanes 7 and 8—SDG, lanes 9 and 10—SECO, lanes 11 and 12—ED, and lanes 13 and 14—EL. (FIG. 6B) High and Low molecular wt DNA forms are presented as percent of total DNA. For each condition, all samples were run in duplicates. The data is presented as mean±standard deviation. P<0.05 was considered significant. * shows the significant difference as compared to untreated DNA. # shows the significant difference as compared to samples exposed to 50 Gy alone.

(FIG. 7A) Epithelial Cells; (FIG. 7B) Endothelial Cells and (FIG. 7C) WT Fibroblasts. Cells were treated with different concentrations of SDG for 6 h prior to gamma irradiation (0, 2, 4, 6, 8 Gy) and incubated. All visible colonies were counted on 12-14th day and surviving fraction was normalized against control values. Data is represented as mean±SEM. ** p≤0.001 * p≤0.01, # p≤0.05 for irradiated cells VS 50 µM SDG pre-treated irradiated cells.

(FIG. 8A) Kinetics evaluation of DNA damage in 2-Gy gamma irradiated primary lung cells (epithelial, endothelial and WT Fibroblasts); At least 100-150 cells were counted for each treatment. DNA damage was assessed by calculating the "tail moment" for each cell (the product of amount of DNA in tail, times the tail length). * p≤0.001 for non-irradiated controls VS their respective irradiated cells; (FIG. 8B) Effect of SDG (50 µM) treatment (0, 2, 4, 6 hours prior to irradiation) on irradiated primary lung cells. Data is represented as mean±SEM. * p≤0.001, # p<0.01 for irradiated cells VS SDG pre-treated irradiated cells. Insert: Representative fluorescence photomicrograph of primary lung epithelial cells. Cells were pre-treated with SDG (50 µM) and exposed to the g-radiation (2 Gy), embedded in agarose, lysed, and electrophoresis was done (0.66 V/cm, 25 min), stained with SYBR green and visualized under fluorescence microscope and thereafter examined for comet tail formation. (A) Control cells, (B) SDG (50 µM), (C) IR (2 Gy) after 30 min of exposure, (D) Cells pre-treated with SDG (50 µM, 6 h) and irradiated.

(FIGS. 13D and 13E). Data is represented as mean±SEM. *p≤0.05, **p≤0.01 for IR-exposed cells compared to either SDG treated cells or SDG+IR treated cells.

(FIG. 14A) Representative images and (FIGS. 14B and 14C) densitometry analysis with normalization to β-actin. Analysis was performed in duplicate and data is represented as mean±SEM. *p≤0.05, **p≤0.01 for IR-exposed cells compared to SDG treated cells.

FIG. 15A shows the ClO⁻ dependent increase in APF and HPF fluorescence. FIG. 15B shows scavenging of ClO⁻ by SDG. FIG. 15C shows the scavenging effect of synthetic SDG diastereomers SDG(S, S) and SDG (R, R). All samples were run in duplicates. The data are presented as mean±standard error. P<0.05 was considered significant. * shows the significant difference as compared to untreated control.

FIGS. 16A and 16B show γ-radiation-induced increase APF and HPF fluorescence. FIGS. 16C and 16D show the effect of SDG on generation of hypochlorite, at increasing doses of radiation in Phosphate buffered saline (PBS) with either APF or HPF (see FIGS. 15A-15C legend). FIGS. 16E, 16F and 16G show γ-radiation-induced chlorination of Taurine. FIG. 16E shows hypochlorite-dependent chlorination of taurine. FIG. 16F shows the taurine chloramine as absorbance for all experimental conditions. FIG. 16G shows the hypochlorite concentration under various conditions as in FIG. 16F. For FIGS. 16A-16E, all samples were run in duplicates whereas for FIGS. 16F and 16G, all samples were run in quadruplets. The data are presented as mean±standard error. P<0.05 was considered significant. * shows the significant difference as compared to the untreated controls.

FIGS. 17A and 17C show representative agarose gels scans of calf thymus DNA after exposure to HOCl. FIGS. 17B and 17D show high and low molecular wt DNA fragments as percent of total DNA. FIGS. 17E and 17F show the effect of SDG on hypochlorite-induced damage to plasmid DNA. FIG. 17E shows a representative agarose gel of plasmid DNA after exposure to HOCl. FIG. 17F shows SC and OC forms presented as percent of total plasmid DNA. For FIG. 17A, Lane 1—1 kb DNA standard ladder, lanes 2 and 3—untreated DNA, lanes 4 and 5—0.1 mM, lanes 6 and 7—0.2 mM, lanes 8 and 9—0.4 mM, lanes 10 and 11—0.5 mM and lanes 12 and 13—0.6 mM ClO⁻. For FIG. 17C, Lane 1-1 kb DNA standard ladder, lanes 2 and 3—untreated DNA, lanes 4 and 0.5 mM HOCl, lanes 6 and 7—0.5 mM HOCl+SDG (com) 1 µM, lanes 8 and 9—0.5 mM HOCl+SDG (S,S) 1 µM, lanes 10-11—0.5 mM HOCl+SDG (R,R) 1 µM, lanes 12-13—0.5 mM HOCl+quercetin 1 µM and lanes 14 and 15—0.5 mM HOCl+silibinin 1 µM. For FIG. 17E, Lane 1-1 kb DNA standard ladder, lanes 2 and 3—untreated plasmid DNA, lanes 4 and 4.5 mM HOCl, lanes 6 and 7—4.5 mM HOCl+SDG 25 µM. For each condition, all samples were run in duplicates. The data are presented as mean±standard error. P<0.05 was considered significant. * and # show the significant difference as compared to untreated DNA.

FIG. 18A shows the representative spectra for all the conditions. FIG. 18B shows the fluorescence at 374 nm under different conditions as in FIG. 18A. FIG. 18C shows the % protection by SDG. For each condition, all samples were run in duplicates. The data are presented as mean±standard error. P<0.05 was considered significant. * and # show the significant difference as compared to untreated 2-AP control and treated, respectively.

FIG. 19A shows the representative spectra for all the conditions.

FIG. 19B shows the fluorescence at 374 nm. For each condition, all samples were run in duplicates. The data are presented as mean±standard error. P<0.05 was considered significant. * and # show the significant difference as compared to untreated 2-AP control and treated, respectively.

FIG. 29: Flaxseed decreases tumor burden in mice: Gross pathological profile of murine lungs exposed to carcinogen. Representative clinical images of murine lungs several months post BaP exposure and dietary flaxseed administration.

FIG. 30: Flaxseed decreases tumor burden in mice: Histopathological profile of murine lungs exposed to carcinogen. Representative H&E-strained lung sections of murine lungs several months post BaP exposure and dietary flaxseed administration. Nodules indicated by the arrows from mice fed control diet (top panels) or flaxseed (lower panels) appear smaller in the flaxseed-fed mice. Each panel represents a different animal.

FIG. 35: Mammalian lignan metabolites are detectable in blood 4 days after daily ingestion of Flaxseed (FS) and Flaxseed Lignan Component (FLC)-supplemented diets. Specifically, Enterodiol (ED) and Enterolactone (EL) can be detected using liquid chromatography, tandem mass spectrometry (LC/MS/MS). Diets were designed to deliver comparable lignan levels, reflected in the detectable lignan metabolite levels in the 2 diets.

FIG. 36: Flaxseed (FS) and Flaxseed Lignan Component (FLC) given prior to asbestos exposure, blunted abdominal inflammation induced by ip crocidolite asbestos injection as evidenced by the numbers of macrophages (MF), neutrophils (PMN) and lymphocytes (Ly). Specifically, FS and FLC significantly decreased macrophage influx in the abdomen. *$p<0.05$

FIGS. 42A-42B: Experimental Schemes for Example 7.

FIG. 43: Clinical study design for Example 7.

FIG. 44: Western Blot showing that feeding 10% FS increases HO-1 and NQO-1 in mouse nasal epithelium.

FIG. 45: Kinetics of HO-1 gene expression in human buccal epithelial cells after 40 g FS diet. (*$P<0.05$ from 0 day).

FIG. 48: SDG or flaxseed diets are hypothesized to decrease asbestos induced ROS/inflammation.

FIG. 51: Evaluation of Asbestos-Induced Oxidative Stress (ROS release) in Culture RAW Macrophages: Asbestos-induced ROS was generated shortly post asbestos exposure and continued for the duration of the observation period.

FIGS. 52A-52B: SDG given to macrophages several hours post exposure to asbestos decreases oxidative stress.

FIGS. 55A-54B: SDG given to macrophages several hours post exposure to asbestos decreases inflammatory cytokine secretion (TNF-α).

DETAILED DESCRIPTION OF THE INVENTION

Figure 1A:
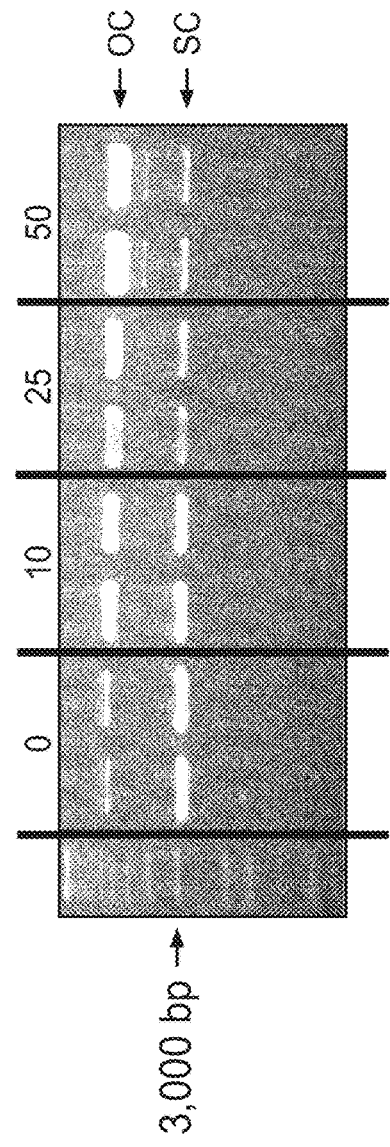
FIGS. 1A-1B: Effect of increasing doses of γ radiation on Plasmid (pBR322) DNA relaxation. Super coiled (SC) represents the compact form. The open coiled (OC) form represents the relaxed or the damaged form of the plasmid.

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Provided herein are therapeutic and prophylactics methods of using flaxseed, its bioactive ingredients, or its metabolites for radioprotection and chemoprevention. In exemplary embodiments, the bioactive ingredient comprises secoisolariciresinol diglucoside (SDG), secoisolariciresinol (SECO), enterodiol (ED), enterolactone (EL), analogs thereof, isomers (including stereoisomers) thereof, or a combination thereof.

The inventors of this application have found that flaxseed, its bioactive ingredients, and/or its degradants or metabolites are effective in protecting biomolecules, cells, and tissues from radiation damage, hypochlorite ion-induced damage, carcinogen-induced damage and malignancy. Accordingly, the inventors have found that flaxseed, its bioactive ingredients, or its metabolites can be used for protecting biomolecules, cells, and tissues from radiation damage, hypochlorite ion-induced damage, carcinogen damage and cancer development.

Subjects in need of radioprotection or radiation mitigation according to methods provided herein are subjects who will, are, or have been exposed to potentially deleterious amounts of radiation. It will be understood that such exposure may be a single exposure, periodic exposure, sporadic exposure or ongoing exposure to the radiation. It is also understood that such radiation exposure includes accidental exposure, incidental or intentional exposure.

Examples of subjects who may be in need of radioprotection or radiation mitigation according to the methods of the present invention include but are not limited to, patients who are exposed to radiation as part of therapeutic regimen (e.g., cancer patients who require radiation therapy), subjects who are exposed to radiation for to diagnose a disease or condition (e.g., subjects receiving dental or bone X-rays, patients receiving PET scans, CT scans and the like). Examples of subjects who may be in need of radioprotection or radiation mitigation according to the methods of the present invention also include those who may be exposed to radiation as a result of their profession or life style choices (e.g., airplane flight crews or other frequent air travelers, and even space travelers, who are exposed to higher than average radiation levels; laboratory technicians and other workers; or those exposed through the use of electronic devices) or those exposed to accumulations of radon (e.g., accumulations in dwellings or mines) or outdoor workers or sunbathers exposed to natural radiation from the sun. Other subjects who may be in need of radioprotection according to the methods of the present invention include those who are accidentally exposed to radiation, such as leaks or spills, (e.g., nuclear reactor leaks or accidents or laboratory spills). Also contemplated are those exposed to radiation as a result of the detonation of a nuclear warhead, as a result of war or terrorism. Additional subjects encompassed are those who are exposed to a terrorist's detonation of conventional explosives that disperse radioactive materials.

Subjects in need of chemoprevention according to methods provided herein are subjects who will, are, or have been exposed to potentially deleterious amounts of carcinogens or other toxicants. It will be understood that such exposure may be a single exposure, periodic exposure, sporadic exposure or ongoing exposure to one or combination of several synthetic or naturally occurring carcinogens or other toxicants, such as chemical warfare agents. It is also understood that such exposure includes accidental exposure, incidental or intentional exposure. It will also be understood that such exposure may be direct exposure or indirect exposure. For example, indirect exposure to hypochlorite ions may be the result of direct exposure to ionizing radiation.

Examples of subjects who may be in need of chemoprevention according to the methods of the present invention include but are not limited to those who may be exposed to carcinogens or other toxicants as a result of their profession or life style choices (e.g., workers in the oil industry; toll booth attendants exposed to automobile exhaust particles; laboratory technicians and other workers). Other subjects who may be in need of chemoprevention according to the methods of the present invention include those who are accidentally exposed to carcinogens, such as leaks or spills of carcinogens in the drinking water or the air (asbestos, polyaromatic hydrocarbons). Also contemplated are those exposed to carcinogens as a result of a habit (smokers). Additional subjects encompassed are those who are exposed to a terrorist's act to disperse carcinogen and other cancer promoting materials, such as chemical warfare agents.

In one aspect, the invention relates to a method for protecting a biomolecule (such as genetic material like a nucleic acid, a protein or a lipid), a cell, or a tissue, from radiation damage in a subject in need thereof, the method comprising: administering to said subject an effective amount of flaxseed, its bioactive ingredient, degradant or a metabolite thereof. Administration to said subjects encompasses administration prior to, during and after exposure to damaging radiation exposure. The time prior, during and post could be seconds, minutes, hours, days, weeks, months or even years. The bioactive ingredient encompasses secoisolariciresinol diglucoside (SDG), secoisolariciresinol (SECO), enterodiol (ED), enterolactone (EL), analogs thereof, stereoisomers thereof, or a combination thereof.

In another aspect, the invention relates to a method for treating or preventing radiation damage in a subject who has been or will be exposed to radiation, the method comprising: administering to said subject an effective amount of at least one bioactive ingredient, wherein said bioactive ingredient comprises secoisolariciresinol diglucoside (SDG), secoisolariciresinol (SECO), enterodiol (ED), enterolactone (EL), analogs thereof, stereoisomers thereof, or a combination thereof.

In another aspect, the invention relates to a method for protecting biomolecule (such as genetic material like a nucleic acid, a protein or a lipid), a cell, or a tissue, from radiation damage resulting from accidental radiation exposure in a subject in need thereof, the method comprising: administering to said subject an effective amount of flaxseed, its bioactive ingredient, degradant or a metabolite thereof.

In another aspect, the invention relates to a method for protecting biomolecule (such as genetic material like a nucleic acid, a protein or a lipid), a cell, or a tissue, from radiation damage resulting in aging.

In another aspect, the invention relates to a method for protecting a biomolecule (such as genetic material like a nucleic acid, a protein or a lipid), a cell, or a tissue from damage resulting from exposure to chemical carcinogens and toxicants, including chemical warfare agents, both natural and synthetic.

In another aspect, the invention relates to a method for protecting a biomolecule (such as genetic material like a nucleic acid, a protein or a lipid), a cell, or a tissue, from radiation damage resulting from radiation therapy for cancer treatment in a subject in need thereof, the method comprising: administering to said subject an effective amount of flaxseed, its bioactive ingredient, degradant or a metabolite thereof.

In another aspect, the invention relates to a method for protecting a biomolecule (such as genetic material like a nucleic acid, a protein or a lipid), a cell, or a tissue from radiation damage in a subject in need thereof, the method comprising: administering to said subject an effective amount of at least one bioactive ingredient, wherein said bioactive ingredient comprises secoisolariciresinol diglucoside (SDG), secoisolariciresinol (SECO), enterodiol (ED), enterolactone (EL), analogs thereof, stereoisomers thereof, or a combination thereof. In some embodiments, the radiation damage results from accidental radiation exposure. In some embodiments, the radiation damage results from radiation therapy for cancer (e.g., lung cancer) treatment.

In another aspect, the invention relates to a method for preventing radiation induced damage to a biomolecule (such as genetic material like a nucleic acid, a protein or a lipid), a cell, or a tissue, in a subject in need thereof, the method comprising: administering to said subject an effective amount of flaxseed, its bioactive ingredient, or a metabolite thereof.

In another aspect, the invention relates to a method for preventing radiation induced damage to a biomolecule (such as genetic material like a nucleic acid, a protein or a lipid), a cell, or a tissue, in a subject in need thereof, the method comprising: administering to said subject an effective amount of at least one bioactive ingredient, wherein said bioactive ingredient comprises secoisolariciresinol diglucoside (SDG), secoisolariciresinol (SECO), enterodiol (ED), enterolactone (EL), analogs thereof, stereoisomers thereof, or a combination thereof.

In another aspect, the invention relates to a method for protecting a biomolecule (such as genetic material like a nucleic acid, a protein or a lipid), a cell, or a tissue, from radiation damage in a cell, the method comprising contacting said cell with an effective amount of at least one bioactive ingredient, wherein said bioactive ingredient comprises secoisolariciresinol diglucoside (SDG), secoisolariciresinol (SECO), enterodiol (ED), enterolactone (EL), analogs thereof, stereoisomers thereof, or a combination thereof.

In another aspect, the invention relates to a method for protecting a biomolecule (such as genetic material like a nucleic acid, a protein or a lipid), a cell, or a tissue, from carcinogen damage in a subject in need thereof, the method comprising: administering to said subject an effective amount of flaxseed, its bioactive ingredient, degradant or a metabolite thereof. Administration to said subjects encompasses administration prior to, during and after exposure to damaging exposure to chemical carcinogens and toxicants both natural and synthetic. The time prior, during and post could be seconds, minutes, hours, days, weeks, months or even years. The bioactive ingredient encompasses secoisolariciresinol diglucoside (SDG), secoisolariciresinol (SECO), enterodiol (ED), enterolactone (EL), analogs thereof, stereoisomers thereof, or a combination thereof.

In another aspect, the invention relates to a method for protecting a biomolecule, from carcinogen damage resulting from accidental exposure to chemical carcinogens and toxicants both natural and synthetic in a subject in need thereof, the method comprising: administering to said subject an effective amount of flaxseed, its bioactive ingredient, degradant or a metabolite thereof.

In another aspect, the invention relates to a method for protecting a biomolecule (such as genetic material like a nucleic acid, a protein or a lipid), a cell, or a tissue, from damage from chemical carcinogens and toxicants both natural and synthetic resulting in lung cancer or mesothelioma.

In another aspect, the invention relates to a method for protecting a biomolecule (such as genetic material like a nucleic acid, a protein or a lipid), a cell, or a tissue, from carcinogen damage, the method comprising: contacting said biomolecule, cell, or tissue with an effective amount of a bioactive ingredient. Contact with said biomolecule, cell, or tissue encompasses contact prior to, during and after exposure to damaging exposure to chemical carcinogens and toxicants both natural and synthetic. The time prior, during and post could be seconds, minutes, hours, days, weeks, months or even years. The bioactive ingredient encompasses secoisolariciresinol diglucoside (SDG), secoisolariciresinol (SECO), enterodiol (ED), enterolactone (EL), analogs thereof, stereoisomers thereof, or a combination thereof.

In another aspect, the invention relates to a method for treating or preventing carcinogen-induced damage, malignant transformation or cancer development in subject who has been or will be exposed to one or more carcinogens from carcinogen-induced cancer, the method comprising: administering to said subject an effective amount of at least one bioactive ingredient, wherein said bioactive ingredient comprises secoisolariciresinol diglucoside (SDG), secoisolariciresinol (SECO), enterodiol (ED), enterolactone (EL), analogs thereof, stereoisomers thereof, or a combination thereof.

In another aspect, the invention relates to a method for protecting a subject exposed to one or more carcinogens from a carcinogen-induced cancer, the method comprising: administering to said subject an effective amount of flaxseed, its bioactive ingredient, or a metabolite thereof.

In another aspect, the invention relates to a method for protecting a biomolecule (such as genetic material like a nucleic acid, a protein or a lipid), a cell, or a tissue, from damage by hypochlorite ions in a subject in need thereof, the method comprising: administering to said subject an effective amount of flaxseed, its bioactive ingredient, degradant or a metabolite thereof. Administration to said subjects encompasses administration prior to, during and after exposure to damaging exposure to chemical carcinogens and toxicants both natural and synthetic. The time prior, during and post could be seconds, minutes, hours, days, weeks, months or even years. The bioactive ingredient encompasses secoisolariciresinol diglucoside (SDG), secoisolariciresinol (SECO), enterodiol (ED), enterolactone (EL), analogs thereof, stereoisomers thereof, or a combination thereof.

In another aspect, the invention relates to a method for treating or preventing hypochlorite ion-induced damage in a subject who has been or will be exposed to hypochlorite ions, the method comprising: administering to said subject an effective amount of at least one bioactive ingredient, wherein said bioactive ingredient comprises secoisolariciresinol diglucoside (SDG), secoisolariciresinol (SECO), enterodiol (ED), enterolactone (EL), analogs thereof, stereoisomers thereof, or a combination thereof.

In another aspect, the invention relates to a method for protecting a biomolecule (such as genetic material like a nucleic acid, a protein or a lipid), a cell, or a tissue, from damage by hypochlorite ions, the method comprising: contacting said biomolecule, cell, or tissue exposed to or to be exposed to hypochlorite ions with an effective amount of a bioactive ingredient. Contact with said biomolecule, cell, or tissue encompasses contact prior to, during and after exposure to damaging exposure to chemical carcinogens and toxicants both natural and synthetic. The time prior, during and post could be seconds, minutes, hours, days, weeks, months or even years. The bioactive ingredient encompasses secoisolariciresinol diglucoside (SDG), secoisolariciresinol (SECO), enterodiol (ED), enterolactone (EL), analogs thereof, stereoisomers thereof, or a combination thereof.

In another aspect, the invention relates to a composition for use in one of the foregoing methods.

Flaxseed, its bioactive ingredients, and its metabolites are known in the art and described in U.S. Patent Publication Nos. 2010/0239696; 2011/0300247; and 2014/0308379; and in International Patent Publication No. WO2014/200964, each of which is incorporated by reference herein in its entirety.

The primary lignan found in flaxseed is 2,3-bis (3-methoxy-4-hydroxybenzyl) butane-1,4-diol (secoisolariciresinol or SECO), which is stored as the conjugate secoisolariciresinol diglucoside (SDG) in its native state in the plant. SDG is metabolized in the human intestine to enterodiol (ED), and enterolactone (EL). Synthetic analogs of enterodiol and enterolactone are known (see, e.g., Eklund et al., *Org. Lett.*, 2003, 5:491).

A "degradant" is a product of the breakdown of a molecule, such as SDG, into smaller molecules.

A "metabolite" is a substance produced by metabolism or by a metabolic process. For example, a metabolite of SDG is EL or ED.

It will be appreciated by one skilled in the art that a metabolite may be a chemically synthesized equivalent of a natural metabolite.

An "analog" is a compound whose structure is related to that of another compound. The analog may be a synthetic analog.

An "ingredient" or "component" is an element or a constituent in a mixture or compound.

A "product" is a substance resulting from a chemical reaction.

An "extract" is a preparation containing an active principle or concentrated essence of a material, for example, from flaxseed.

"Pharmaceutical composition" refers to an effective amount of an active ingredient, e.g., (S,S)-SDG (R,R)-SDG, meso-SDG, SDG, SECO, EL, ED and analogs thereof, together with a pharmaceutically acceptable carrier or diluent. A "therapeutically effective amount" refers to that amount which provides a therapeutic effect for a given condition and administration regimen.

The compositions described herein may include a "therapeutically effective amount." A "therapeutically effective amount" refers to an amount effective, at dosages and for periods of time necessary, to achieve the desired therapeutic result. A therapeutically effective amount may vary according to factors such as the disease state, age, sex, and weight of the individual, and the ability of the composition to elicit a desired response in the individual. A therapeutically effective amount is also one in which toxic or detrimental effects of the molecule are outweighed by the therapeutically beneficial effects.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable excipient" as used herein includes both one and more than one such excipient.

The pharmaceutical compositions can be administered to a subject by any suitable method known to a person skilled in the art, such as orally, parenterally, transmucosally, transdermally, intramuscularly, intravenously, intra-dermally, subcutaneously, intra-peritonealy, intra-ventricularly, intracranially, intra-vaginally, intra-tumorally, or bucally. Controlled release may also be used by embedding the active ingredient in an appropriate polymer which may then be inserted subcutaneously, intratumorally, bucally, as a patch on the skin, or vaginally Coating a medical device with the active ingredient is also covered.

In some embodiments, the pharmaceutical compositions are administered orally, and are thus formulated in a form suitable for oral administration, i.e., as a solid or a liquid preparation. Suitable solid oral formulations include tablets, capsules, pills, granules, pellets and the like. Suitable liquid oral formulations include solutions, suspensions, dispersions, emulsions, oils and the like. In some embodiments, the active ingredient is formulated in a capsule. In accordance with this embodiment, the compositions of the present invention comprise, in addition to the active compound and the inert carrier or diluent, drying agent, in addition to other excipients as well as a gelatin capsule.

In some embodiments, the pharmaceutical compositions are administered by intravenous, intra-arterial, or intramuscular injection of a liquid preparation. In some embodiments, the pharmaceutical composition is a liquid preparation formulated for oral administration. In some embodiments, the pharmaceutical composition is a liquid preparation formulated for intravaginal administration. Suitable liquid formulations include solutions, suspensions, dispersions, emulsions, oils and the like. In some embodiments, the pharmaceutical compositions are administered intravenously and are thus formulated in a form suitable for intravenous administration. In another embodiment, the pharmaceutical compositions are administered intra-arterially and are thus formulated in a form suitable for intra-arterial administration. In some embodiments, the pharmaceutical compositions are administered intra-muscularly and are thus formulated in a form suitable for intra-muscular administration. In some embodiments, the pharmaceutical compositions are administered intra-bucally and are thus formulated in a form suitable for buccal administration.

In some embodiments, the pharmaceutical compositions are administered topically to body surfaces and are thus formulated in a form suitable for topical administration. Suitable topical formulations include gels, ointments, creams, lotions, drops, controlled release polymers and the like. For topical administration, the flaxseed, its bioactive ingredient, or a metabolite thereof is prepared and applied as a solution, suspension, or emulsion in a physiologically acceptable diluent with or without a pharmaceutical carrier.

In some embodiments, the pharmaceutical compositions provided herein are controlled-release compositions, i.e. compositions in which the flaxseed, its bioactive ingredient, or a metabolite thereof is released over a period of time after administration. Controlled- or sustained-release compositions include formulation in lipophilic depots (e.g. fatty acids, waxes, oils). In other embodiments, the composition is an immediate-release composition, i.e. a composition in which all the flaxseed, its bioactive ingredient, or a metabolite thereof is released immediately after administration.

In some embodiments, compositions for use in the methods provided herein are administered at a therapeutic dose once per day. In some embodiments, the compositions are administered once every two days, twice a week, once a week, or once every two weeks.

Techniques for extracting and purifying SDG are known in the art and described in U.S. Pat. No. 5,705,618, which is incorporated herein by reference. Techniques for synthesizing SDG, its stereoisomers and analogs are described in Mishra O P, et al. *Bioorganic & Medicinal Chemistry Letters* 2013, (19):5325-5328 and in International Patent Publication No. WO2014/200964, which are hereby incorporated by reference in their entireties. Bioactive components for use in the methods provided herein may also be chemically synthesized directly into the mammalian, readily metabolizable forms, Enterodiol (ED) or Enterolactone (EL), as is known in the art.

(S,S)-SDG (R,R)-SDG, (S,R)-SDG (R,S)-SDG, meso-SDG, SECO, EL, ED or an analog thereof may be administered at a dose of 0.1 ng/kg to 500 mg/kg.

The treatment with (S,S)-SDG (R,R)-SDG, (S,R)-SDG (R,S)-SDG, meso-SDG, SDG, SECO, EL, ED or an analog thereof is a single administration to several days, months, years, or indefinitely.

As used herein, "treating" may refer to either therapeutic treatment or prophylactic or preventative measures, wherein the object is to prevent or lessen the targeted pathologic condition or disorder as described herein, or both. Therefore, compositions for use in the methods provided herein may be administered to a subject before the exposure, e.g., to radiation, a carcinogen, a toxicant, or hypochlorite ions. In some cases, compositions for use in the methods provided herein may be administered to a subject after the exposure. Thus treating a condition as described herein may refer to preventing, inhibiting, or suppressing the condition in a subject.

Furthermore, as used herein, the terms "treat" and "treatment" refer to therapeutic treatment, as well prophylactic or preventative measures, wherein the object is to prevent or slow down (lessen) an undesired physiological change associated with a disease or condition. Beneficial or desired clinical results include, but are not limited to, alleviation of symptoms, diminishment of the extent of a disease or condition, stabilization of a disease or condition (i.e., where the disease or condition does not worsen), delay or slowing of the progression of a disease or condition, amelioration or palliation of the disease or condition, and remission (whether partial or total) of the disease or condition, whether detectable or undetectable. "Treatment" can also mean prolonging survival as compared to expected survival if not receiving treatment. Those in need of treatment include those already having been exposed, e.g., to radiation, a carcinogen, a toxicant, or hypochlorite ions, as well as those prone to being exposed or those expecting to be exposed.

In some embodiments, subjects in need of treatment and the methods and compositions described herein may include, but are not limited to, subjects with lung diseases and disorders, such as asthma, cancer, COPD, and mesothelioma. In some embodiments, suitable subjects may include subjects with disorders and conditions associated with aging, such as cardiovascular disorders and conditions, sagging skin and central nervous system (CNS) diseases (e.g., Alzheimer's dementia). In some embodiments, suitable subjects may include skin disorders and conditions (e.g., psoriasis), as well as subjects with cosmetic skin conditions (e.g., wrinkles and age spots). In some embodiments, suitable subjects may include subjects with gastrointestinal disorders and conditions, such as IBD and chron's disease. In some embodiments, suitable subjects may include subjects with cardiovascular disorders and conditions. In some embodiments, suitable subjects may include subjects with melanoma. In some embodiments, suitable subjects may include subjects with ocular diseases, such as macular degeneration. In some embodiments, suitable subjects may include subjects with cancer, such as breast cancer, prostate cancer and uterine cancer. In some embodiments, suitable subjects include subjects with cognitive impairment and other cognitive disorders.

The term "subject" includes mammals, e.g., humans, companion animals (e.g., dogs, cats, birds, and the like), farm animals (e.g., cows, sheep, pigs, horses, fowl, and the like) and laboratory animals (e.g., rats, mice, guinea pigs, birds, and the like). In addition to humans, the subject may include dogs, cats, pigs, cows, sheep, goats, horses, buffalo, ostriches, guinea pigs, rats, mice, birds (e.g., parakeets) and other wild, domesticated or commercially useful animals (e.g., chicken, geese, turkeys, fish). The term "subject" does not exclude an individual that is normal in all respects. The term "subject" includes, but is not limited to, a human in need of therapy for, or susceptible to, a condition or its sequelae.

The term "about" or "approximately" means within an acceptable error range for the particular value as determined by one of ordinary skill in the art, which will depend in part on how the value is measured or determined, i.e., the limitations of the measurement system.

The following examples are presented in order to more fully illustrate the preferred embodiments of the invention. They should in no way be construed, however, as limiting the broad scope of the invention.

EXAMPLES

Example 1

Synthetic (S,S) and (R,R)-Secoisolariciresinol Diglucosides (SDGs) Protect Naked Plasmid and Genomic DNA From Gamma Radiation Damage As a consequence of nuclear disintegration, three types of radiations are produced namely, the alpha (α) with a positive charge, the beta (β) with a negative charge and the gamma (γ) with no charge. In case of γ-radiation, the electromagnetic wave has a very small wavelength (<0.005 nm) and thus has high energy which is capable of ionizing molecules and atoms. In biological systems or in solution, ionizing radiation generates hydroxyl radicals (⁻OH) by water radiolysis. These hydroxyl radicals (⁻OH) are the predominant source of ionizing radiation-induced damage to cellular components including lipids, proteins and genomic DNA. The hydroxyl radicals (⁻OH) produced by γ-radiation result in single-strand and double-strand breaks in DNA. The (⁻OH) radicals damage DNA by abstracting H-atoms from the deoxyribose and purine as well as pyrimidine bases or add to the double bonds of the bases. These reactions result in DNA strand breaks.

Compounds with antioxidant and free radical scavenging properties can function as radioprotectors and prevent radiation-induced DNA damage. Due to complex extraction, purification and enrichment methods to isolate secoisolariciresinol diglucoside (SDG) from natural resources associated with high costs, variability and difficulty to produce large quantities of SDG to make preclinical and clinical testing feasible, SDG was chemically synthesized. Using the natural compounds vanillin and glucose, two enantiomers (their structures are depicted below) of SDG:SDG (S,S) and SDG (R,R), were successfully synthesized (Mishra et al., *Bioorganic & Medicinal Chemistry Letters* 2013, (19): 5325).

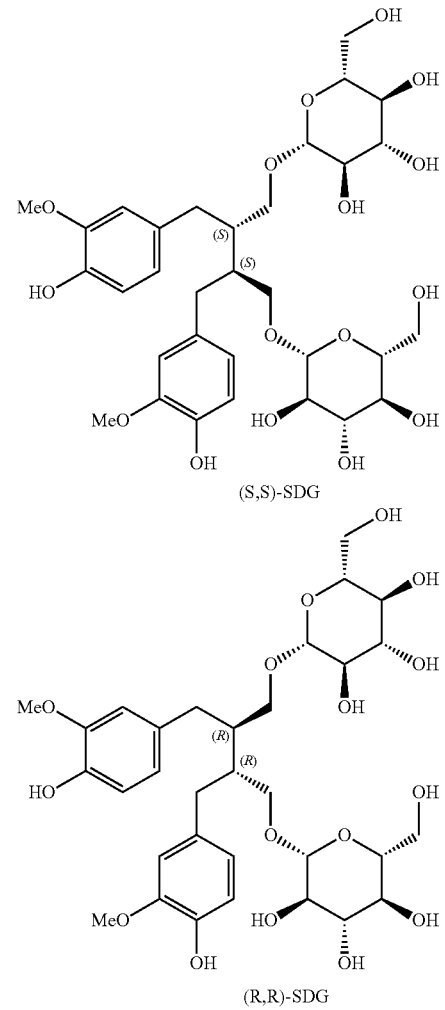

SDG has been shown in many studies by Christofidou-Solomidou et al., in addition to others, to be a potent antioxidant agent and a potent free radical scavenger. Importantly, in a recent study, the synthetic SDG enantiomers have been shown to possess strong antioxidant and free radical, scavenging characteristics (Mishra et al., *Bioorganic & Medicinal Chemistry Letters* 2013, (19):5325-5328). In the present example, the radioprotective properties of the synthesized SDG enantiomers (S,S)-SDG and (R,R)-SDG as they compare to the commercial SDG were investigated and evaluated. The radioprotective characteristics of the three compounds were assessed using the plasmid DNA relaxation assay by determining the ability of the SDGs to prevent the super coil to open coil plasmid DNA (pBR322) conversion following the exposure of the plasmid to γ-irradiation as well as by evaluating inhibition of genomic DNA fragmentation following the exposure of the DNA to γ-irradiation. SDG is metabolized by intestinal bacteria to produce secoisolariciresinol (SECO), enterodiol (ED) and enterolactone (EL). Therefore, the effect of these metabolites of SDG on γ-irradiation-induced fragmentation of genomic DNA was also evaluated.

Material and Methods

Chemicals

Plasmid DNA (pBR322), ethidium bromide, ultrapure 10×TAE buffer and 1 kb plus DNA ladder were purchased from Invitrogen (Life Technologies, Carlsbad, Calif.). Agarose (ultrapure) and calf thymus DNA were purchased from Sigma-Aldrich (St. Louis, Mo.). Secoisolariciresinol Diglucoside (SDG) (commercial), Secoisolariciresinol (SECO), enterodiol (ED) and enterolactone (EL) were purchased from Chromadex (Irvine, Calif.).

Synthesis of Secoisolariciresinol Diglucoside (SDG)

Synthetic SDG (R,R) and SDG (S,S) stereoisomers were synthesized as describe in Mishra et al., *Bioorganic & Medicinal Chemistry Letters* 2013, (19):5325-5328.

Exposure of Plasmid DNA and Calf Thymus DNA to γ-Radiation

Plasmid DNA (pBR322) or calf thymus DNA samples with or without varying concentrations of SDG (R,R), SDG (S,S) and SDG (commercial) were exposed to γ-radiation with a Mark 1 cesium (Cs-137) irradiator (J. L. Shepherd, San Fernando, Calif.) at a dose rate of 1.7 Gy/min in phosphate buffered saline, pH 7.4 (PBS).

Determination of Radiation-Induced Plasmid DNA Relaxation

The effect of test compounds on radiation-induced strand breaks and supercoil (SC) to open coil (OC) conversion was determined using plasmid DNA (pBR322) (Life Technologies, Carlsbad, Calif.). Plasmid DNA (500 ng) in PBS (pH 7.4) was mixed with various concentrations (25-250 µM) of SDG (R,R), SDG (S,S) and SDG (commercial) and irradiated at 25 Gy in PBS. At 30 min post radiation exposure, samples were mixed with loading dye and subjected to agarose (1%) gel electrophoresis in TAE buffer (pH, 8.3) at 100 V. The gel was stained with ethidium bromide (0.5 µg/ml) for 40 min, washed for 20 min and then visualized on a UV trans-illuminator (Bio-Rad, Hercules, Calif.). The captured gel images were scanned and the density of the open coiled (OC) and super coiled (SC) plasmid DNA bands determined by Gel-doc image analyzer program. The density of the SC and OC plasmid DNA was expressed as % of the total density (OC+SC).

Determination of Radiation-Induced DNA Fragmentation

The effect of test compounds on radiation-induced strand breaks in DNA was determined using calf thymus DNA (Sigma, St. Louis, Mo.). DNA (500 ng) in PBS (pH 7.4) was mixed with varying concentrations (25-250 µM) of SDG (R,R), SDG (S,S) and SDG (commercial) and irradiated at 50 Gy for 30 min. A second series of experiments were performed at varying concentrations ranging from 0.5-10 µM. Samples were mixed with loading dye and subjected to agarose (1%) gel electrophoresis in TAE buffer (pH, 8.3) at 100 V. The gel was stained with ethidium bromide (0.5 µg/ml) for 40 min, washed for 20 min and then visualized on a UV trans-illuminator (Bio-Rad, Hercules, Calif.). The captured gel images were scanned and the density of the calf thymus DNA fragments was determined by Gel-Pro image analyzer program (Media Cybernetics, Silver Spring, Md.). The density of the low mol. wt (<6,000 bps) and the high mol. wt (>6,000 bps) fragments of calf thymus DNA was expressed as % of the total density (low mol wt.+high mol. wt.).

Data Analysis

Data obtained are presented as mean values ±standard deviation. The data were subjected to one-way analysis of variance (ANOVA) with post-hoc comparison using Bonferroni correction using Statview Program. P value ≤0.05 was considered as significant.

Results

The radioprotective potential of synthetic SDG (R,R), SDG (S,S) and SDG (commercial) was determined using plasmid DNA (pBR322). The radioprotection assay used in this study is based on the principle that plasmid DNA following exposure to γ-radiation moves slower than the unexposed plasmid DNA. This is simply due to the fact that the super coiled plasmid DNA moves faster in the agarose gel due to its compact size. By comparison, the radiation-induced nicks in the plasmid DNA unravel super coil resulting in a relatively lager size plasmid which moves with a slower rate in the gel. Therefore, determining the density of the open coiled as compared to super coiled plasmid DNA reflects the extent of radiation-induced damage.

Radiation Causes a Dose-Dependent SC to OC DNA Plasmid Conversion

To select a radiation dose that causes significant DNA damage yet allows for a therapeutic window to test a radiation mitigating agent, plasmid DNA was exposed to 10, 25 and 50 Gy gamma radiation. The results presented in FIG. 1A show that there is a radiation dose-dependent increase in OC form as well as a radiation dose-dependent decrease in SC form of the plasmid DNA. The distribution of SC and OC (FIG. 1B) shows that the % of SC decreased from 68.73±2.54% to 50.91±2.31, 38.37±3.73 and 35.66±4.24% (p<0.05), in 0, 10, 25 and 50 Gy, respectively. At the same time, the % of OC increased from 31.26±2.50% to 49.08±2.31% 61.62±3.73% and 67.33±4.24% (p<0.05), in 0, 10, 25 and 50 Gy, respectively. Based on these initial experiments, a radiation dose of 25 Gy (at which a considerable and clearly demonstrable damage was achieved) was selected for the subsequent experiments to determine the radioprotective characteristics of the different SDGs.

Radioprotective Activity of Synthetic SDG Using Plasmid DNA Relaxation Assay

Plasmid DNA was exposed to the selected dose of 25 Gy gamma radiation (see FIG. 1) and the % inhibition of DNA damage (SC to OC formation) was determined for each of the SDG agents (synthetic and commercial) at various concentrations (25-250 µM).

Figure 2A:
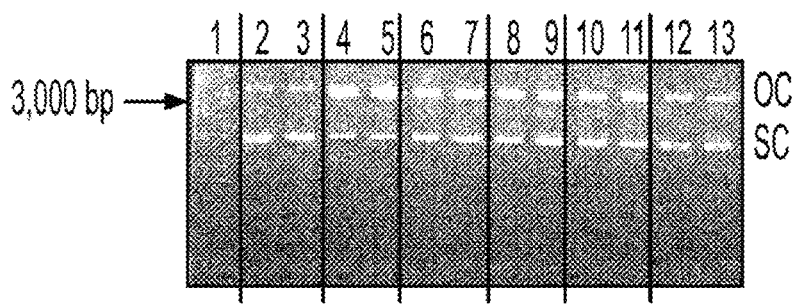
FIGS. 2A-2I: Effect of increasing concentration of synthetic SDG (S,S), SDG (R,R) and commercial SDG on γ radiation-induced Plasmid (pBR322) DNA relaxation. All samples were exposed to a γ radiation dose of 25 Gray. SDGs concentrations were 25, 50, 100 and 250 µM. In FIGS. (2A), (2D), and (2G)—representative agarose gel scans of plasmid DNA after exposure to 25 Gy in the presence of 25, 50, 100 and 250 µM SDG (S,S), SDG (R,R) and SDG (commercial) are shown. Lane 1—1 kb DNA standard ladder, lanes 2 and 3—untreated plasmid DNA, lanes 4 and 5-25 µM, lanes 6 and 7-50 µM, lanes 8 and 9-100 µM, and lanes 10 and 11-250 µM SDGs. In FIGS. (2B), (2E) and (2H)—SC and OC forms are presented as percent of total plasmid DNA. For each condition, all samples were run in duplicates. The data is presented as mean±standard deviation. $P<0.05$ was considered significant. * and # show the significant difference as compared to untreated SC and OC forms, respectively. ** and ## show significant differences as compared to samples exposed to 25 Gy without SDGs. In FIGS. (2C), (2F) and (2I), SDGs-dependent inhibition of plasmid DNA relaxation is shown. EC50 values were determined from the quadratic equations presented under the curves.
Figure 2B:
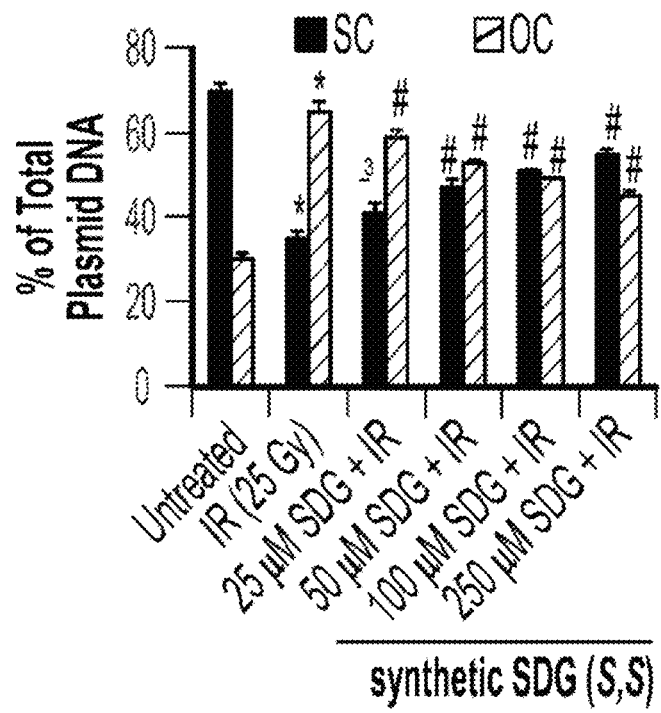
Figure 2C:
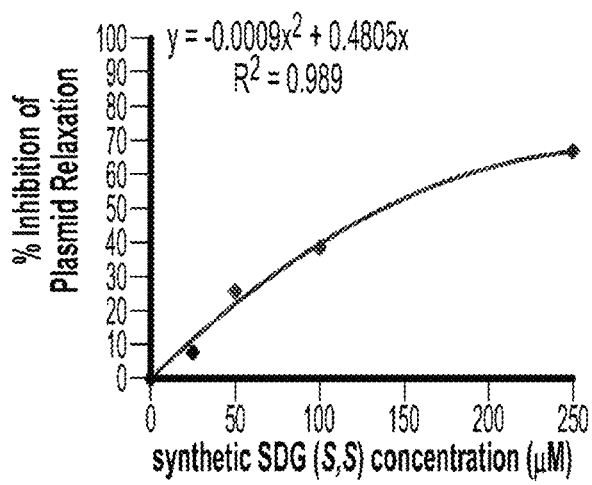
Figure 2D:
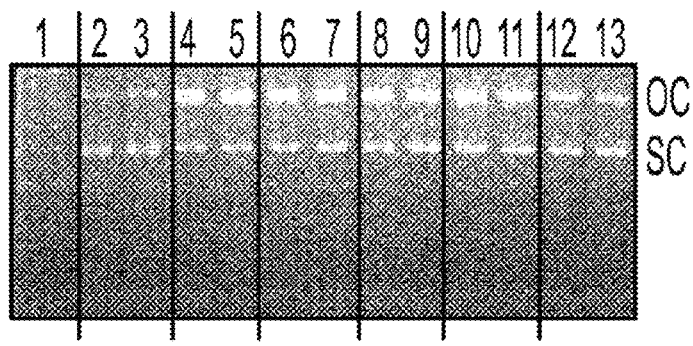
Figure 2E:
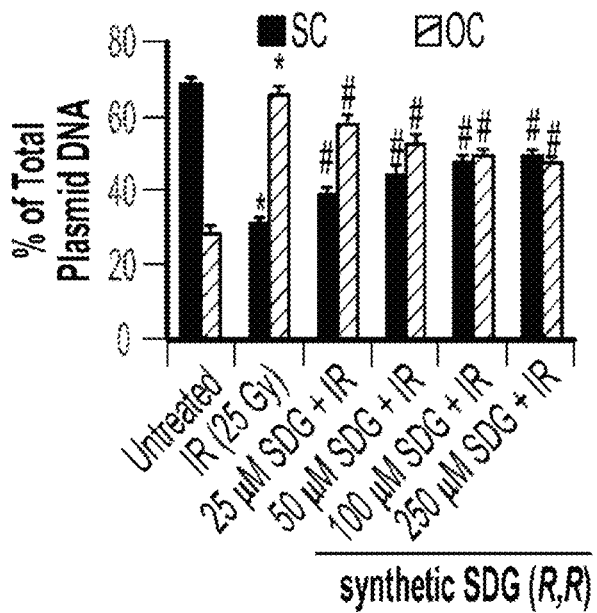
Figure 2F:
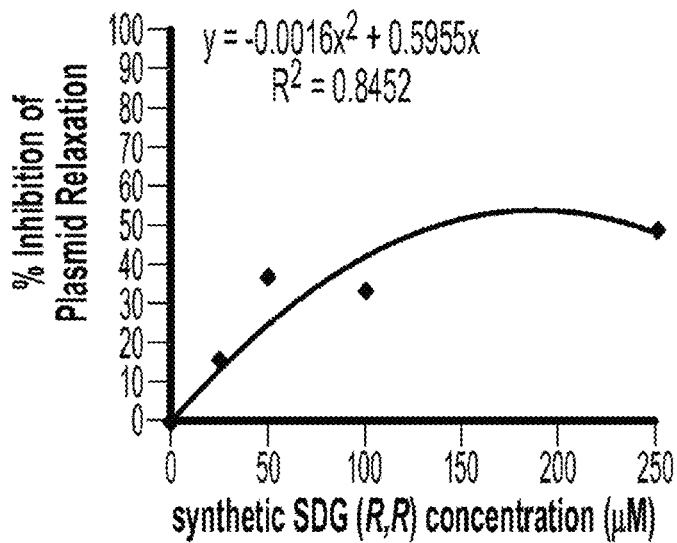
Figure 2G:
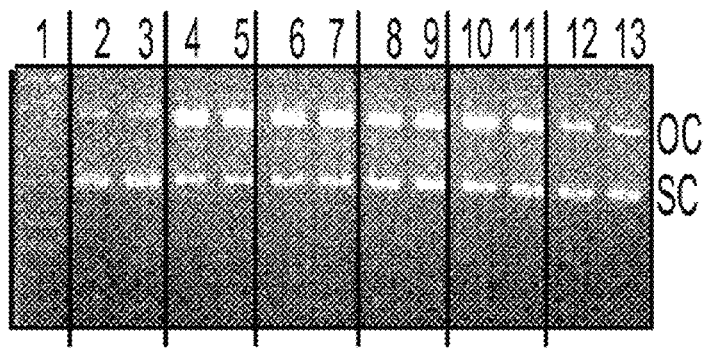
Figure 2H:
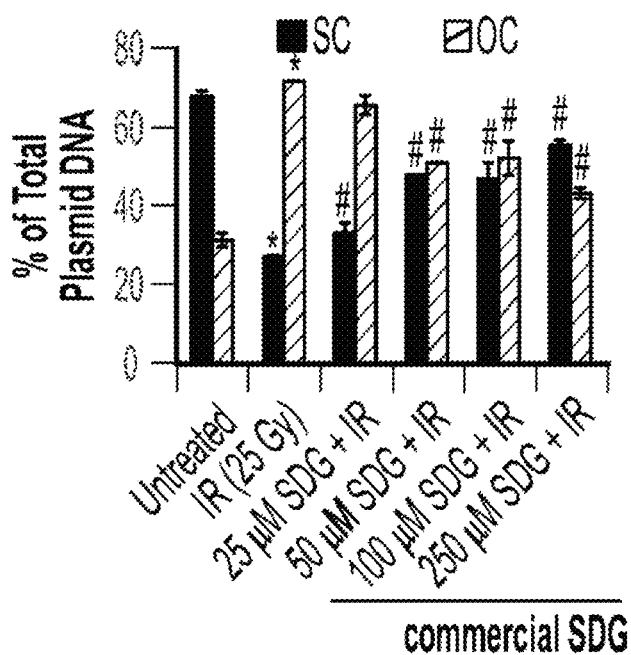
Figure 2I:
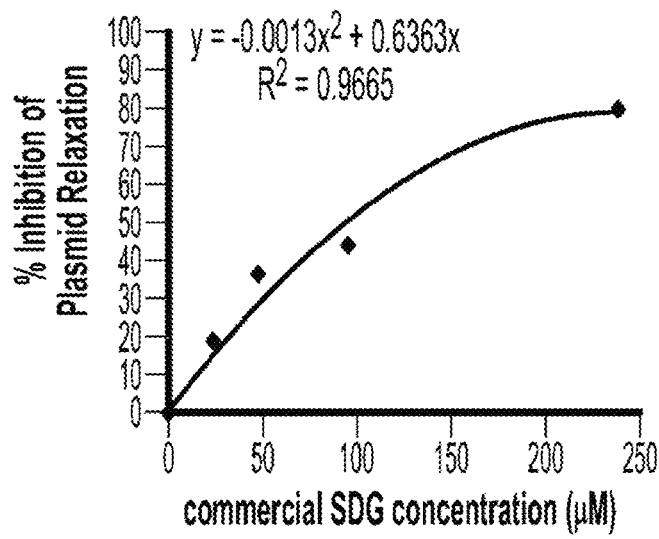

A representative gel blot of plasmid DNA after exposure to 25 Gy in the presence of 25, 50, 100 and 250 µM SDG (S,S) is shown in FIG. 2A and semiquantitative densitometric analysis is shown in FIG. 2B while % inhibition as compared to control is shown in FIG. 2C. Interestingly, in the presence of increasing concentrations of SDG (S,S) (25, 50, 100 and 250 µM), the proportion of the SC form increased and the density of OC form decreased significantly (p<0.05) and dose-dependently. Using the % inhibition plot (FIG. 2C), the $EC_{50}$ value can be determined for each agent (i.e., the effective concentration (EC) needed to prevent 50% of plasmid relaxation at 25 Gy) which for SDG (S,S) is 141.77 µM. This value for preventing plasmid DNA relaxation is comparable to the $EC_{50}$ value for scavenging DPPH free radicals. These results demonstrate the radioprotective characteristics of the synthetic SDG (S, S) enantiomer Similar results were shown for the SDG (R,R) enantiomer (FIG. 2D-F) and SDG (commercial) (FIG. 2, G-I) with an $EC_{50}$ of 127.96 µM and 98.38 µM, respectively. These values for preventing plasmid DNA relaxation are comparable to the respective EC50 value for scavenging DPPH free radicals. These results demonstrate the radioprotective characteristics of both synthetic and commercially available, natural SDG.

Figure 3B:
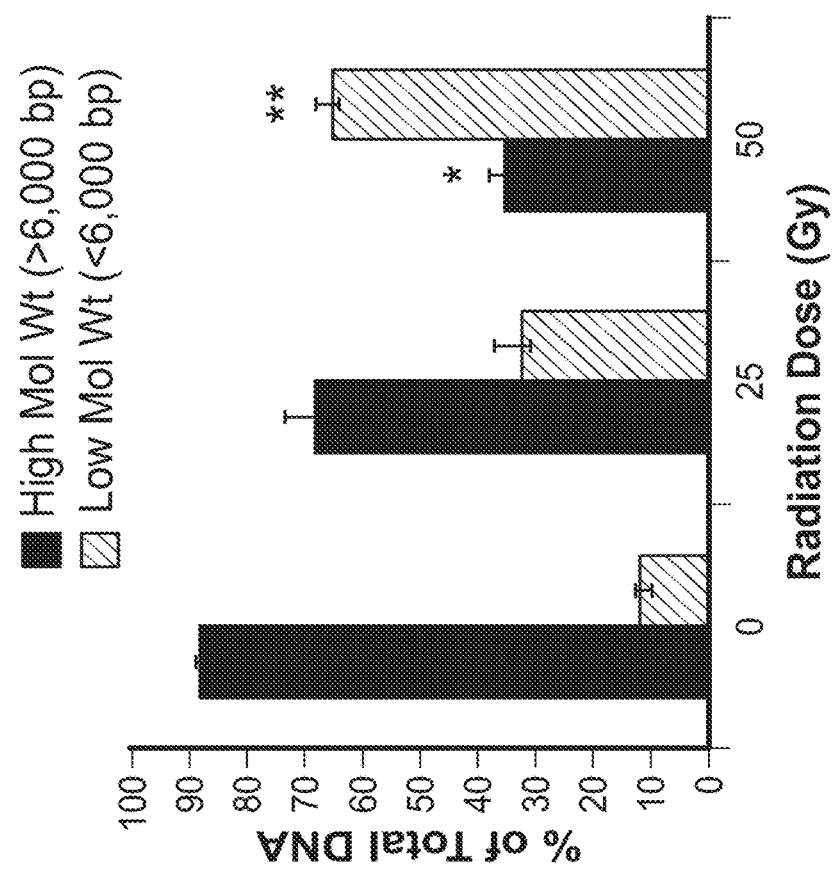
FIGS. 3A-3B: Effect of increasing doses of γ radiation on calf thymus DNA fragmentation. DNA exposed to γ-radiation generates fragments of small molecular weights which move faster than the higher molecular wt. DNA. Determining the density of the low molecular wt DNA fragments (<6,000 bps) as compared to the high molecular wt. DNA (>6,000 bps) reflects the extent of radiation-induced damage.
Figure 3A:
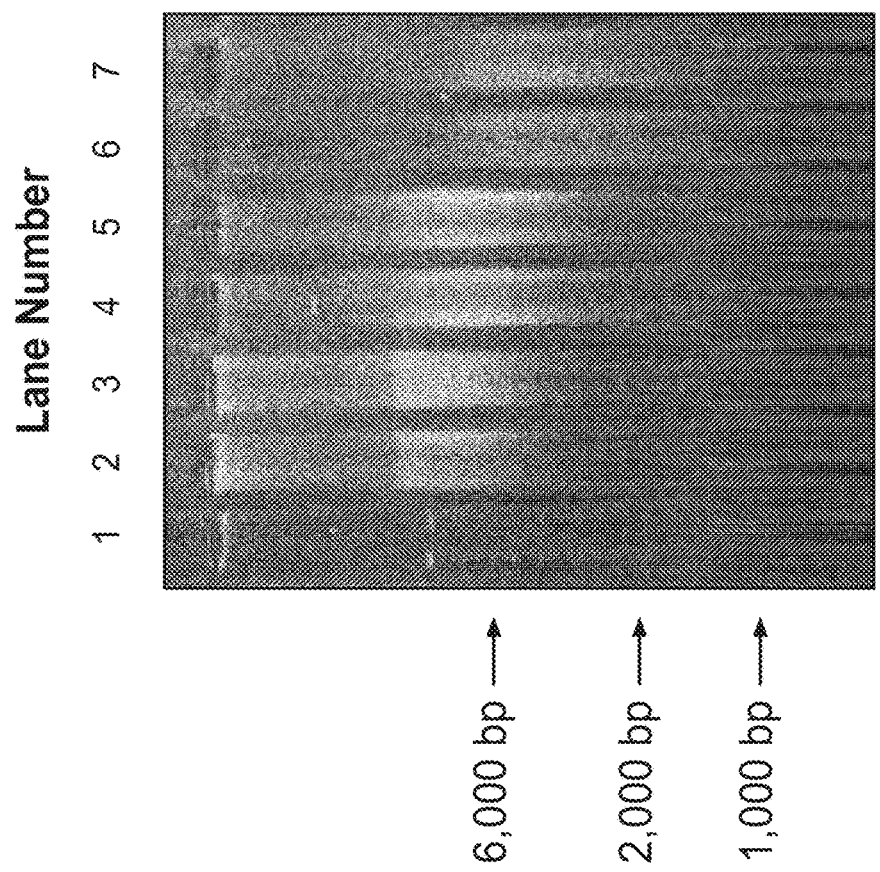

Radiation Causes Dose-Dependent DNA Fragmentation from High to Low Molecular Weight Fragments Radiation induces an increase in DNA fragmentation as shown in the DNA gel in FIG. 3A. Based on size, the calf thymus DNA fragments were divided into two groups: high mol. wt. (>6,000 bps) size and low mol. wt. (<6,000 bps) size. The distribution (FIG. 3B) of high and the low mol. wt. fragments show that the % of the high mol. wt. DNA decreased from 88.16±0.50% to 67.82±7.89 and 34.94±4.45% (p<0.05) at 25 and 50 Gy, respectively. At the same time, the proportion of low mol. wt. fragments increased from 11.83±0.50 to 32.17±7.89% and 65.05±4.45% (p<0.05) at 25 and 50 Gy, respectively. Results (FIG. 3B) show a significant decrease in high mol. wt. DNA and a significant increase in low mol. wt. DNA fragments indicating damage to DNA at 50 Gy. Based on these initial experiments, a radiation dose of 50 Gy (at which a clear demonstrable calf thymus DNA fragmentation was observed), was selected for the following experiments determining the radioprotection characteristic of different SDGs.

Radioprotective Activity of Synthetic SDG Using Calf Thymus DNA Fragmentation Assay The radioprotective potential of synthetic SDG (R,R), SDG (S,S) and SDG (commercial) was determined using radiation-induced fragmentation of calf thymus DNA as described above.

High SDG Concentration (25-250 µM):

FIG. 4A shows a representative DNA gel of calf thymus DNA after exposure to 50 Gy in the presence of 25, 50, 100 and 250 µM SDG (S,S). In the presence of increasing concentrations of SDG (S,S) (25, 50, 100 and 250 µM), the proportion of the high mol. wt. DNA form increased significantly (p<0.05) following radiation exposure while the low mol. wt. fragments decreased. The distribution of high and low mol. wt size DNA forms in presence of various concentrations of SDG (S,S) is presented in FIG. 4B. These results demonstrate the radioprotective characteristic of our synthetic SDG (S, S) enantiomer using calf thymus genomic DNA. Similarly, results presented in FIGS. 4C-4D and 4E-4F show the radioprotective properties of synthetic SDG (R,R) and SDG (commercial), respectively. These results demonstrate the radioprotective characteristic of synthetic SDG (R,R) and (S,S) enantiomers using calf thymus genomic DNA.

To further determine the lower limits of SDG in DNA protection, a series of DNA fragmentation experiments testing lower concentrations of all 3 SDGs were performed, ranging from 0.5-10 µM.

Low SDG Concentration (0.5-10 µM):

The results of experiments performed at low concentrations of SDG (S,S), SDG (R,R) and SDG (commercial) as compared to their $EC_{50}$ values for antioxidant and free radical scavenging activity are presented in FIGS. 5A-F. Similarly to the higher SDG concentrations, these results presented in this section using calf thymus DNA fragmentation assay demonstrate that the synthetic SDG (S,S), and SDG (R,R) enantiomers possess strong radioprotection characteristics even at low concentrations.

Figure 6B:
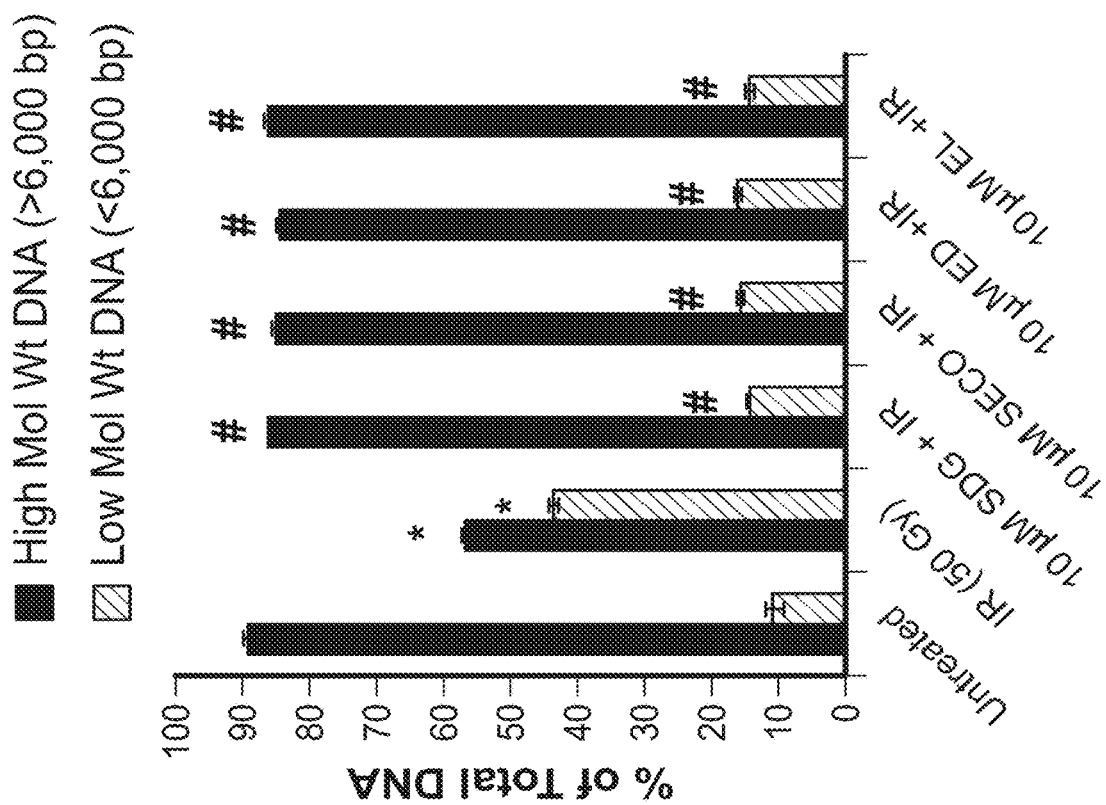
FIGS. 6A-6B: Effect of SDG, SECO, ED and EL on γ radiation-induced calf thymus DNA fragmentation. All samples were exposed to a γ radiation dose of 50 Gy. SDG, SECO, ED and EL were used at 10 µM concentration.
Figure 6A:
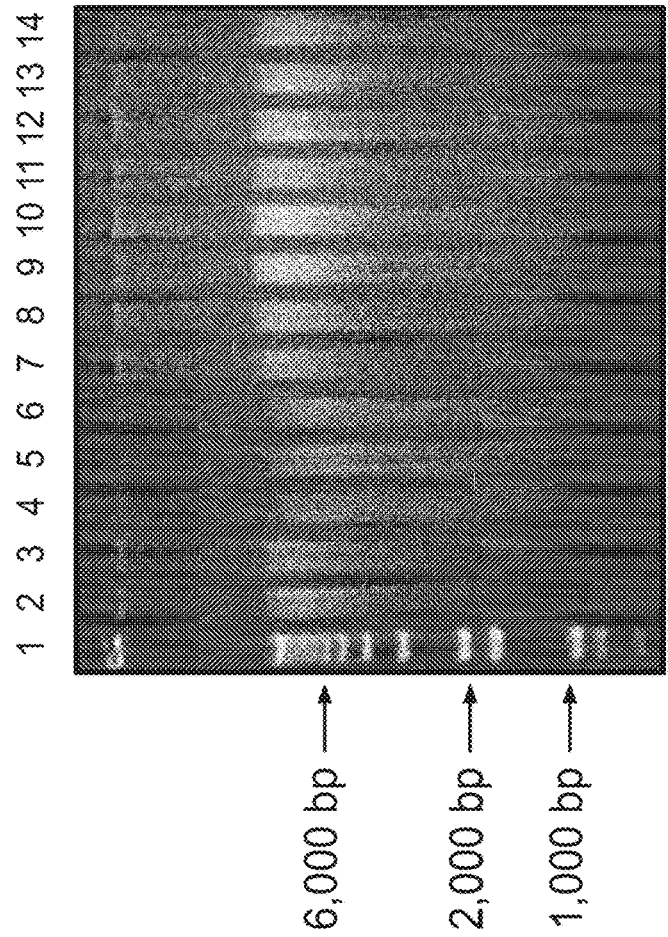

Radioprotective Activity of SDG Metabolites Using Calf Thymus DNA Fragmentation Assay The radioprotective potential of SDG metabolites SECO, ED and EL was determined and compared with SDG using radiation-induced fragmentation of calf thymus DNA as described above. The concentration of 10 µM of each the test agent was selected based on previous findings shown above as a median effective dose. The results are shown in FIGS. 6A-6B. The data demonstrate that SDG and its metabolites SECO, ED, EL are equipotent with respect to their radioprotective properties.

Discussion

The results of the present example show that synthetic SDG (S, S) and SDG (R,R) enantiomers possess strong radioprotective properties. The radioprotection potential of these enantiomers, as determined using plasmid DNA (pBR322), increased with increases in their concentration. These synthetic SDG (S,S) and SDG (R,R) enantiomers prevented the radiation-induced damage to plasmid DNA in a concentration-dependent manner. The radioprotection potential of the synthetic isomers of SDG was comparable to commercial SDG. Synthetic enantiomers SDG (S,S) and SDG (R,R) also prevented the radiation-induced DNA fragmentation of calf thymus genomic DNA. At the lowest concentration tested, SDG (S, S) and SDG (R,R) completely prevented the radiation induced generation of low mol. wt. fragments of calf thymus DNA demonstrating strong radioprotective characteristics of synthetic SDG (S,S) and SDG (R,R) enantiomers. Results using low concentrations of SDG (S,S), SDG (R,R) and SDG (commercial) indicated that the concentration required for protecting calf thymus DNA from γ radiation damage is much lower as compared to the $EC_{50}$ values for their antioxidant and free radical scavenging activity. Importantly, the mammalian lignan metabolites of SDG, SECO, ED and EL showed equally potent DNA-protective properties.

Flavonoids possess strong antioxidant activity; specifically, such polyphenols possess free radical-scavenging activities, and are known to be more effective antioxidants in vitro than vitamins E and C. Dietary and medicinal plants possessing antioxidant properties are also known to prevent many human diseases associated with oxidative stress and are useful radioprotectors. Antioxidants, including vitamins and minerals, suppressed the levels of clastogenic factors in Chernobyl workers many years after radiation exposure. We have been investigating the role of whole grain dietary flaxseed, a grain rich in lignan polyphenols, as well as of flaxseed lignan formulations enriched in SDG, in radiation-induced damage using a mouse model of thoracic radiation damage. We have shown that flaxseed ameliorated the radiation-induced inflammation and oxidative stress in mice when administered both prior to and after radiation exposure. We also demonstrated that irradiated mice fed diets containing only the lignan component of flaxseed, enriched in the lignan biphenol SDG, also showed significantly improved hemodynamic measurements and survival while also improving lung inflammation and oxidative tissue damage. These studies indicated that flaxseed through the actions of the lignan SDG is protective against radiation-induced tissue damage in-vivo.

Increased generation of reactive oxygen species (ROS) such as superoxide anion ($O_2^-$), hydroxyl radical ($^-OH$), and hydrogen peroxide leads to tissue damage under various experimental and pathological conditions. Reactive oxygen species result in cellular damage by oxidative modification of cellular membrane lipids, proteins and the genomic DNA. A number of studies have shown that extracted, purified or synthetic flaxseed SDG is a potent anti-oxidant in vitro as well as in vivo. Therefore, SDG as an antioxidant has therapeutic potential under various experimental and disease conditions including radiation-induced tissue damage in patients undergoing radiation therapy.

Polyphenols commonly occur as glycosides in plants and possess antioxidant properties. Flavonoids, as antioxidants, interfere with the activities of enzymes involved in generation of reactive oxygen species, quenching of free radicals, chelating transition metals and rendering them redox inactive in the Fenton reaction. Secoisolariciresinol (SDG) is the major lignan in flaxseed and has been shown to be a potent anti-oxidant in vitro as well as in vivo. In order to explore the therapeutic potential of flaxseed lignan secoisolariciresinol (SDG), SDG was synthesized by a chemical reaction using vanillin as a precursor molecule and antioxidant properties of the synthetic SDG (R,R) and SDG (S,S) was determined by assessing their reducing power, metal chelating potential, and free radical scavenging activity for hydroxyl, peroxyl and DPPH radicals. In the present example, we have investigated the radioprotective characteristics of synthetic SDG (R,R), SDG (S,S) enantiomers and a commercially available SDG (as control) by assessing their potential for preventing γ-irradiation-induced damage to plasmid DNA (pBR322) and calf thymus DNA. Radiation-induced damage to plasmid DNA was assessed by the increase in open coiled form of plasmid DNA and decrease in super coiled form of the plasmid DNA. Radiation-induced damage to genomic DNA was assessed by determining the level of DNA fragmentation. In this example, we have examined the efficacy of synthetic SDG (R,R), SDG (S,S) and commercial SDG against radiation-induced DNA damage in a cell-free system.

The antioxidant properties of the SDG molecule have been previously demonstrated. We have shown that natural, commercially available SDG has potent free-radical scavenging properties in cells exposed to gamma radiation. The antioxidant and free radical scavenging characteristics of these synthetic SDG (R,R) and SDG (S,S) enantiomers were investigated and have been demonstrated to possess strong reducing power, high metal-ion chelating potential, and high free radical scavenging activity for hydroxyl, peroxyl and DPPH radicals. These characteristics of the synthetic SDG (R,R) and SDG (S,S) indicate that these molecules show strong potential for modulating cellular redox state, decreasing metal-ion concentration, and scavenging oxygen free radicals. These characteristics of the synthetic SDG enantiomers suggest their ability to function by acting at and preventing all the three steps of initiation, propagation as well as termination of the free radical reaction, suggesting that these underlying mechanisms are potentially responsible for the radioprotective characteristics of the SDG (S,S) and SDG (R,R) enantiomers in vivo.

One observation that was made is that the maximum radioprotection of genomic DNA by SDG is already achieved at approximately 5.0 μM concentration which is well below the $EC_{50}$ values for their free radical scavenging and antioxidant effects. Therefore, SDG as an antioxidant and free radical scavenger can also function as a DNA radioprotector and radiation mitigator.

In summary, in the present example, synthetic SDG (S,S) and SDG (R,R) enantiomers were demonstrated to possess strong radioprotection characteristics. The radioprotection potential of these enantiomers was determined using plasmid DNA (pBR322) and calf thymus DNA. The synthetic SDG (S,S) and SDG (R,R) enantiomers prevented the radiation-induced damage to plasmid DNA in a concentration-dependent manner Synthetic enantiomers SDG (S,S) and SDG (R,R) also prevented the radiation-induced fragmentation of calf thymus genomic DNA. At the concentration of 5 SDG (S,S) and SDG (R,R) completely prevented the radiation-induced generation of low mol. wt. fragments of calf thymus DNA demonstrating strong radioprotective characteristics possessed by these enantiomers.

Example 2

Radioprotective Properties of the Lignan Secoisolariciresinol Diglucoside (SDG) in Lung Cells Radiation injury to cells is initiated by the generation of reactive oxygen species (ROS). The spectrum of the damage inflicted by ROS to the cellular machinery includes lipid peroxidation, DNA-protein crosslinks, base modifications, adduct formation and single- and double-strand breaks (DNA SSBs and DSBs). These modifications have been implicated in radiation-induced apoptosis and cell death. Since cellular DNA damage is a known determining factor in radiation-induced cell death, significant efforts have been made to identify and exploit agents which can protect DNA against radiation damage through interfering with free radical reactions or by modulating radiation-induced apoptosis.

Prevention from radiation-induced genotoxicity can be achieved by the presence of antioxidants in the system at the time of exposure. Since antioxidants can be ROS scavengers that interfere with free radical chain reactions, it is possible to protect cellular DNA from radiation-induced oxidative stress by supplementation with antioxidants. A number of synthetic and natural antioxidant compounds have been studied for their radioprotective efficacy. However most of them exhibit inherent toxicity and side effects at their effective concentrations, or have short shelf life and low bioavailability. Hence the search for effective and non-toxic radioprotectors has led to investigations into dietary antioxidants and nutraceuticals.

We have evaluated the protective effects of dietary flaxseed (FS) supplementation in preclinical murine models of oxidative lung damage such as hyperoxia, acid aspiration injury, and ischemia/reperfusion injury. We determined that the protective effects of FS may be due in part to its ability to enhance antioxidant enzyme expression in lung tissues. Importantly, dietary FS ameliorated the adverse effects of thoracic radiation when given both prior to exposure as well as post-exposure. In these studies, dietary flaxseed decreased radiation-induced oxidative lung tissue damage, decreased lung inflammation and prevented pulmonary fibrosis.

Earlier reports suggested that the diversified action of flaxseed might be attributed to its lignans which have been shown to possess antioxidant, anti-inflammatory and anti-carcinogenic effects. Secoisolariciresinol diglucoside (SDG) is the prominent FS lignan (about 1% of dry weight), which possibly contributes to the beneficial health effects of FS grain. SDG is metabolized in the intestine to mammalian lignans, i.e. enterodiol (ED) and enterolactone (EL) by intestinal bacteria. SDG was shown to be beneficial in the treatment of number of pre-clinical models of diseases such as atherosclerosis and diabetes. SDG has also been reported to exert cardioprotective effects in animal models. FS lignans are protective against diverse cancer types as summarized in a recent review on the health effects of SDG by Adolphe et al (*Br J Nutr* 2010, 103:929) and reported to reduce melanoma metastasis in animals.

In addition, the antioxidant and free radical scavenging properties of SDG are well documented, which is of paramount importance as the free radical scavenging ability of a compound can be directly related to its radioprotective efficacy. In our studies on lung endothelial cells, SDG exhibited free radical scavenging properties when cells were exposed to gamma-irradiation while the entire flaxseed lignan component (FLC) enriched in SDG, mediated radioprotection and radiation mitigation in mice. However, characterization of the radioprotective properties of SDG has not been established.

This study was performed to determine the radioprotective ability of FS lignan SDG and to explore the possible mechanisms responsible for its action. The first aim of this study was to evaluate role of SDG on radiation-induced clonogenic death in primary murine lung cells, specifically in epithelial, endothelial cells and fibroblasts. Since radiation-induced reproductive death of cells is directly related to cellular DNA damage, we assessed whether SDG can protect cells from radiation-induced DNA strand breaks by using alkaline comet assay (SSBs) and formation of γ-H2AX foci (DSBs). Furthermore, we examined the effect of SDG pre-treatment in preventing murine primary lung cells from IR-induced cell death. A number of studies have demonstrated the role of the pro-apoptotic protein Bax (Bcl-2-associated X protein) in IR-induced cell death. We also analyzed direct effect of SDG on Bax and its antagonist Bcl-2 (B cell leukemia/lymphoma 2) mRNA expression to determine whether the mechanism of SDG protection involves a shift in the ratio of these key regulators of apoptosis. Our findings identify the lignan SDG, a potent bioactive ingredient in FS, mediates radioprotection in lung cells thus providing novel insight into the radioprotective effects of FS.

Material and Methods

Reagents

Secoisolariciresinol Diglucoside (SDG) is commercially available (ChromaDex, Inc., CA). Comet assay kit was purchased from Trevigen, Inc., (Gaithersburg, Md.). P-Histone H2AX (rabbit mAb) was purchased from Cell Signaling Technology, Inc., (Danvers, Mass.). Phosphate buffered saline (PBS), Bovine serum albumin (BSA), Dulbecco's modified Eagle's medium (DMEM) with L-glutamine, glucose 1 g/l, without sodium bicarbonate), HEPES buffer, trypsin, bovine serum albumin (BSA), ethylenediamine tetra acetic acid (EDTA), 4,6diamidino 2-phenyl indole (DAPI), Fetal bovine serum (FBS), Collagenase, Triton-X 100 and Dispase were purchased from Sigma-Aldrich, St. Louis, Mo., USA.

Cell Lines

Fibroblasts and endothelial cells were isolated from C57/bl6 mouse. For fibroblast isolation, mouse lungs were harvested, minced, and incubated with dispase (2 mg/ml) for 45 minutes. Pieces were plated out and fibroblasts were cultured as described previously and used between passages 3 and 10. Pulmonary microvascular endothelial cells (PMVEC) were isolated from murine lungs as described previously. Briefly, freshly harvested mouse lungs were treated with collagenase followed by isolation of cells by adherence to magnetic beads coated with mAb to platelet endothelial cell adhesion molecule (PECAM). Epithelial cells (C10) cells were originally derived from a normal BALB/c mouse lung explant and are non-tumorigenic, contact-inhibited, and have alveolar type 2 cell features at early passage.

Clonogenic Survival

Exponentially growing cells were plated as single cells and incubated overnight. Cells were treated with various doses of the lignan SDG (10-50 µM) 6 h prior to irradiation (2, 4, 6 and 8 Gy). Lignan dose was selected based on animal studies to be within the physiological levels reached in the blood circulation when 10% Flaxseed is ingested. Cells were irradiated with a Mark 1 cesium (Cs-137) irradiator (J. L. Shepherd, San Fernando, Calif.) at a dose rate of 1.7 Gy/min Colonies were stained and counted 10 to 15 days after irradiation and surviving fraction was calculated.

COMET Analysis

Exponentially growing cells were cultured and treated with SDG (50 µM) at different time intervals prior to irradiation (2 Gy). Cells were processed for comet assay as per manufacturer's instructions (Trevigen, Gaithersburg, Md.). Briefly, cells ($1 \times 10^5$ cells/ml in PBS) were mixed with LMAgarose® (1:10, v/v) and immediately pipetted onto CometSlide™. Cells were then lysed (4° C., 30 min) and kept in dark for unwinding (RT). Electrophoresis was done in a horizontal electrophoresis unit at 18 volts (200 Amp) for 25 minutes. Slides were washed twice with DW, fixed in 70% ethanol and dried at 45° C. DNA was stained by SYBR green (Trevigen). At least 150 cells were scored per group. Visual analysis of cells and comet tail length was measured using Comet Image Analysis software (Comet Assay IV, Perceptive Instruments Ltd, Haverhill, UK) Images were captured on an Olympus IX51 fluorescence microscope using a monochrome CCD FireWire camera.

Immunostaining and Flow Cytometry for γ-H2AX.

For immunostaining of γ-H2AX, cells were plated on glass coverslips (5,000 cells/coverslip), pre-treated (6 h) with 50 µM SDG and irradiated (2 Gy). At desired time interval, cells were fixed (4% para-formaldehyde), washed and blocked with PBST (PBS+0.1% TritonX-100 containing 5% goat serum, 1% BSA). Cells were incubated with γ-H2AX primary antibody (1:200) overnight at 4° C. followed by washing with PBST (3×5 min) and incubation with secondary antibody (Alexa Fluor® 488, Invitrogen, Calif., USA) for 1 hr at RT. Nuclei were counterstained with DAPI and visualized under fluorescence microscope.

For FACS analysis, cells were trypsinized and washed with PBS. Cells were then fixed (Fix/Perm buffer, eBioscience), for 45 minutes and washed thereafter using permeabilization wash buffer (BioLegend, USA). Cells were resuspended in 200 µl rabbit monoclonal phospho-histone γ-H2AX (Ser 139) antibody conjugated to Alexa Fluor® 488 (1:100 v/v, Cell Signaling Technology, US) and incubated for 30 min at 4° C. Cells were washed again with wash buffer and analyzed. The CyAn ADP (Advanced Digital Processing) flow cytometer (Dako, Denmark) Coulter, Fullerton, Calif.) was used to measure γ-H2AX and positive cells were quantified using Summit Software (Dako, Denmark).

Morphological Detection of Apoptotic Cells

Apoptotic cells are morphologically characterized by condensation of nucleus and cytoplasm, membrane blebbing, cell shrinkage, and breakdown of nuclear DNA, first in large segments and subsequently in nucleosomal fragments and finally formation of well-enclosed apoptotic bodies. Percentage of cells undergoing apoptosis was determined microscopically from the slides used for micronuclei detection (cytogenetic damage). At least, 500 cells were counted for each experiment (experiment done twice) and percent apoptotic cells were determined as follows:

% Cell Death=$N_a/N_t \times 100$, where $N_a$ is the number of cells with apoptotic bodies and $N_t$ is the total number of cells analyzed.

Gene Expression Analysis by Quantitative Real Time PCR (qPCR)

qPCR was performed using TaqMan® Probe-Based Gene Expression Assays supplied by Applied Biosystems, Life Technologies (Carlsbad, Calif.). To evaluate the effect of SDG treatment on the mRNA expression of apoptotic genes, individual TaqMan® gene expression assays were performed for Bax (Mm00432051_m1) and Bcl-2 (Mm00477631_m1).

Briefly, cells were pre-treated with SDG (50 μM, 6 hrs) and irradiated (2 Gy). Total RNA was isolated from using RNeasy Plus Mini Kit (Qiagen, Valencia, Calif.) and quantified using a NanoDrop 2000 (ThermoFisher Scientific, Waltham, Mass.). Reverse transcription of RNA to cDNA was then performed on a Veriti® Thermal Cycler using the High Capacity RNA to cDNA kit supplied by Applied Biosystems, Life Technologies (Carlsbad, Calif.). qPCR was performed using 25 ng of cDNA per reaction well on a StepOnePlus™ Real-Time PCR System (Applied Biosystems, Life Technologies, Carlsbad, Calif.). Gene expression data was normalized to 18S ribosomal RNA and calibrated to untreated control samples according to the $\Delta\Delta C_T$ method.

Apoptosis Detection by Western Blotting

Apoptosis was determined in mouse lung epithelial cells by levels of Bax (an apoptosis promoter), Bcl-2 (an apoptosis inhibitor), cleaved caspase-3, and cleaved poly (adenosine diphosphate-ribose) polymerase (PARP) seen using immunoblotting. Briefly, cells were lysed in PBS containing protease inhibitors. Immunoblot analysis of cell lysates was then performed using 10 well SDS 12% NuPAGE gel (Invitrogen, Carlsbad Calif.). Electrophoresis was performed at 200V for 1 hour. Transfer to PolyScreen PV transfer membrane (PerkinElmer Life Sciences, Boston, Mass.) was performed for 1 hour at 25 volts. Membrane was blocked overnight in 5% non-fat dry milk in phosphate buffered saline. The non-fat dry milk was then discarded and the membrane was incubated with primary antibody. Protein levels of Bax, Bcl-2, cleaved caspase-3, and cleaved PARP were detected using manufacturer recommended dilutions (Cell Signaling Technology, Danvers, Mass.) using rabbit anti-mouse monoclonal antibody against BAX and Bcl-2, and rabbit anti-mouse cleaved caspase-3 (Asp175), monoclonal antibody and a rabbit polyclonal anti-cleaved PARP (214/215) cleavage site specific antibody. The membrane was washed five times and then incubated in secondary antibody conjugated to horseradish peroxidase for 45 minutes at room temperature. Membranes were developed using Western Lighting Chemiluminescence Reagent Plus (PerkinElmer Life Sciences, Boston, Mass.) and quantified by densitometry scanning of specific bands (20 kDa for Bax, 26 kDa for Bcl-2, 17/19 kDa for cleaved caspase-3, and 89 kDa for cleaved PARP) that were adjusted for loading using β-actin expression level detected by specific secondary antibody (Sigma, St. Louis, Mo.).

Statistics

Results are expressed as mean±SEM. Survival curve for clonogenic assay was prepared using KaleidaGraph software (4.0). Statistical differences among groups were determined using one-way analysis of variance (ANOVA). When statistically significant differences were found ($p<0.05$) individual comparisons were made using the Bonferoni/Dunn test (Statview 4.0).

Results

SDG Treatment Increases Colony Forming Ability of Irradiated Primary Lung Cells

Figure 1B:
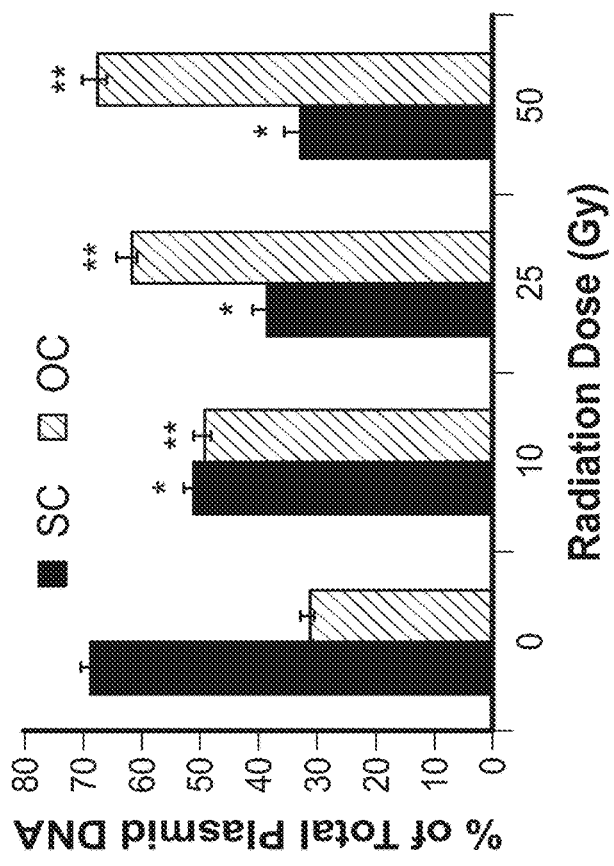

The clonogenic survival assay has been used widely to determine cellular reproductive death after a cell undergoes any genotoxic stress after exposure to environmental and pharmaceutical carcinogens, ionizing radiation etc. In this example, the effect of SDG (10-50 μM) pre-treatment on radiation-induced reduction in clonogenicity of primary lung cells (epithelial cells, endothelial cells and fibroblasts, respectively) was evaluated. Results show that SDG (10-50 μM) alone did not elicit any adverse effect on the colony forming ability of all the three cell types as compared to their respective untreated control cells (100%) (FIGS. 1A-1B).

Figure 7A:
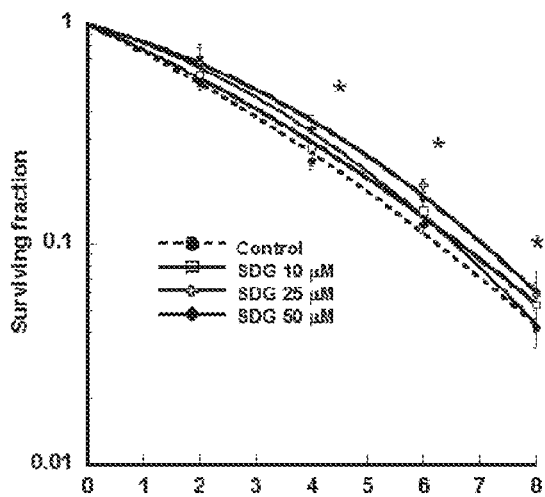
FIGS. 7A-7C: Effect of SDG treatment on radiation dose response of murine primary lung cells.
Figure 7B:
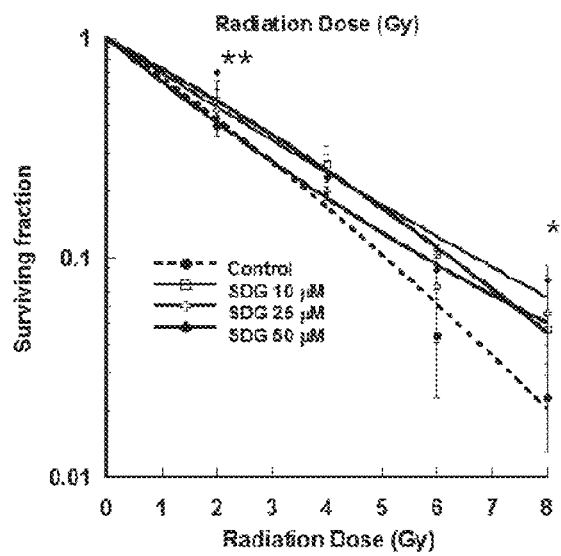
Figure 7C:
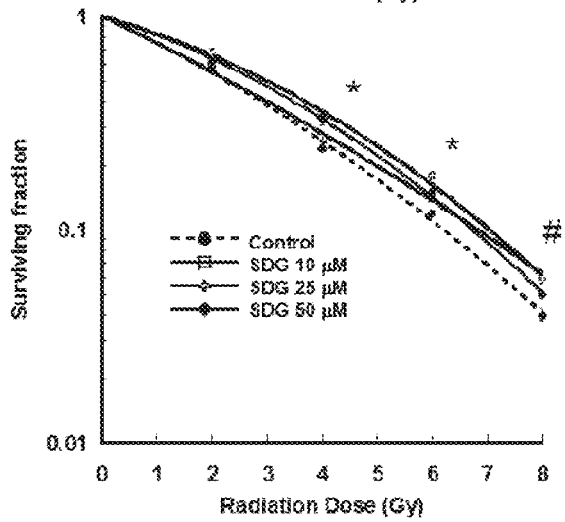

Radiation treatment significantly ($p \leq 0.01$) reduced the colony forming ability of epithelial and endothelial cells in a dose-dependent manner. When cells were treated with SDG prior to irradiation, the surviving fraction was enhanced significantly in all the treatment groups (FIGS. 7A, 7B). Maximum protection against radiation-induced loss in clonogenicity in fibroblasts was observed in 50 μM SDG pre-treated irradiated group (FIG. 7C). Therefore, we selected this particular concentration of SDG for our further studies.

SDG Prevents Formation of DNA SSBs in Irradiated Primary Lung Cells

Figure 8A:
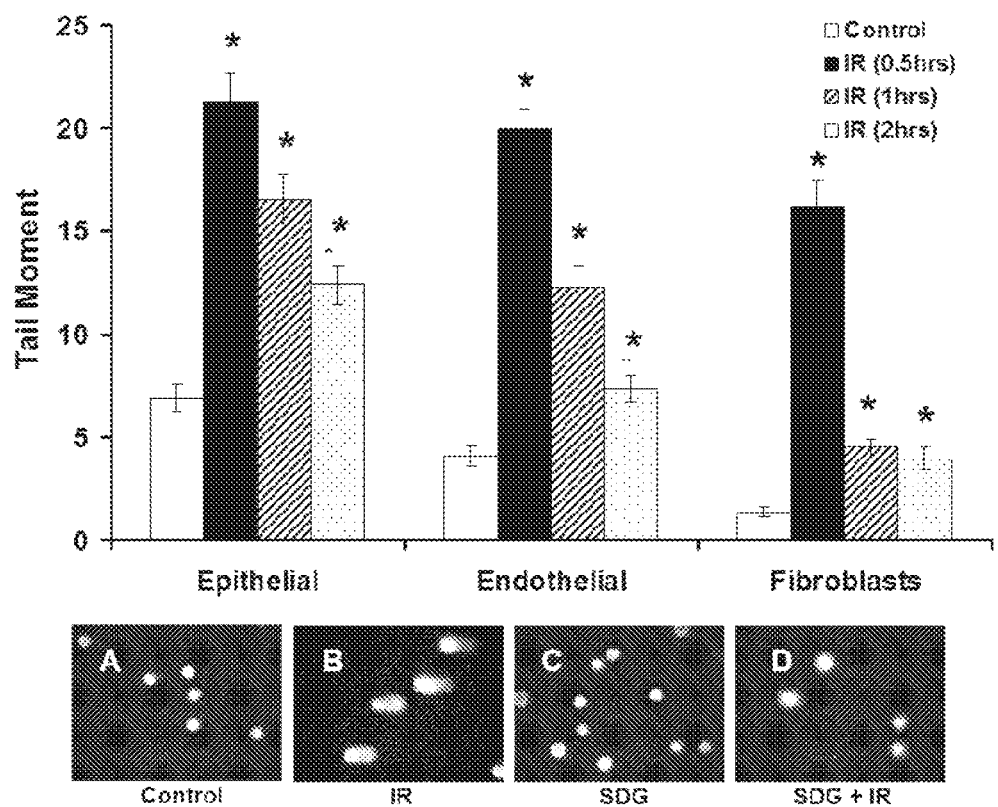
FIGS. 8A-8B: Evaluation of the radiation-induced DNA single strand breaks (SSB) in lung cells using the alkaline comet assay.

We first performed a study to determine the kinetics of DNA damage in all cell types (endothelial, epithelial, fibroblasts) following a radiobiologically relevant dose of 2 Gy. As expected, radiation exposure induced significant DNA damage, as evidenced by the increased tail moment, in all cell types compared to their respective non-irradiated control cells. The extent of DNA damage was maximum at 30 minutes post-irradiation. The extent of DNA damage was decreased as time post-irradiation reached up to 60 minutes and further steeply declined by 2 h post irradiation. Hence, we opted for 30 minutes time interval for further studies related to radiation induced DNA damage (FIG. 8A).

Figure 8B:
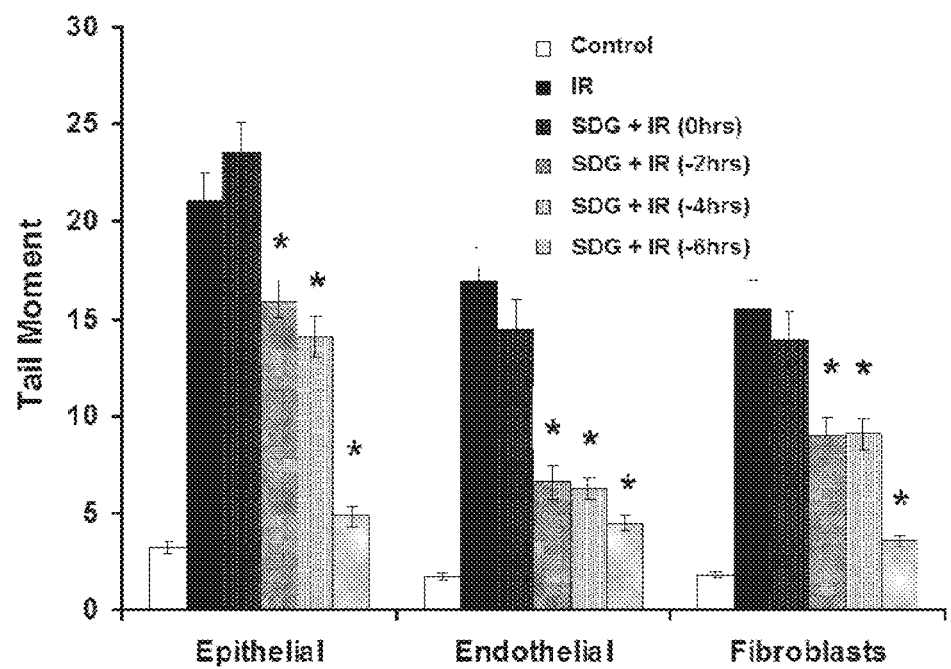

Radiation exposure (2 Gy) led to a significant increase in comet tail length in comparison to their non-irradiated control cells. Cells were treated at various time intervals (0 h, 2 h, 4 h, 6 h and 24 h) prior to irradiation. Pre-treatment of cells with SDG (50 μM), at all time intervals, significantly inhibited radiation-induced comet tail length in all three types of lung cells. However, maximum protection against radiation-induced tail moment of DNA in all cell types was observed at 6 h SDG treatment prior to irradiation (FIG. 8B). A representative fluorescence photomicrograph depicting the formation of comet tails, in irradiated (in presence and/or absence of SDG) lung epithelial cells, has been shown in the Insert, FIG. 8B.

Figure 9A:
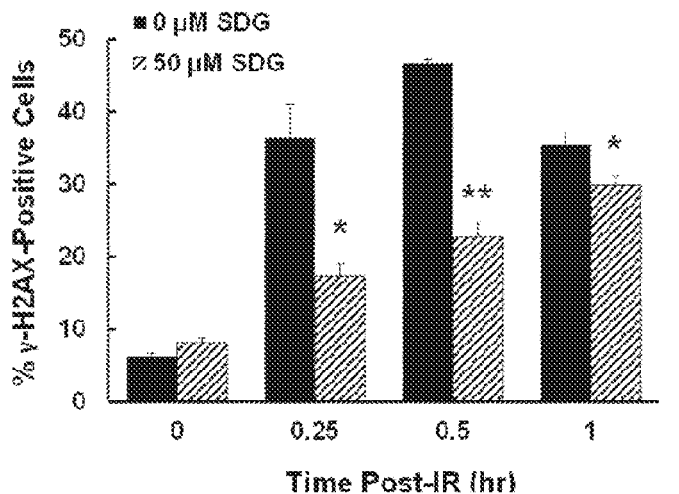
FIGS. 9A-C: Fluorescent evaluation of the induction of γ-H2AX foci in irradiated murine primary lung cells viz. epithelial cells, endothelial cells and WT fibroblasts. Cells were treated with SDG (50 µM) for 6 h and gamma-irradiated (2 Gy). At desired time interval, cells were fixed in 4% paraformaldehyde, washed, probed with γ-H2AX antibody and nuclei was counterstained using DAPI. Cells were visualized under a fluorescence microscope. Total cells (blue) γ-H2AX positive cells (green) were counted per field and percentage of γ-H2AX positive cells was calculated. At least 500 cells were counted for each treatment and experiment done twice. Data is represented as mean±SEM. *p≤0.05, ** p≤0.005 for irradiated cells VS. SDG pre-treated irradiated cells.
Figure 9B:
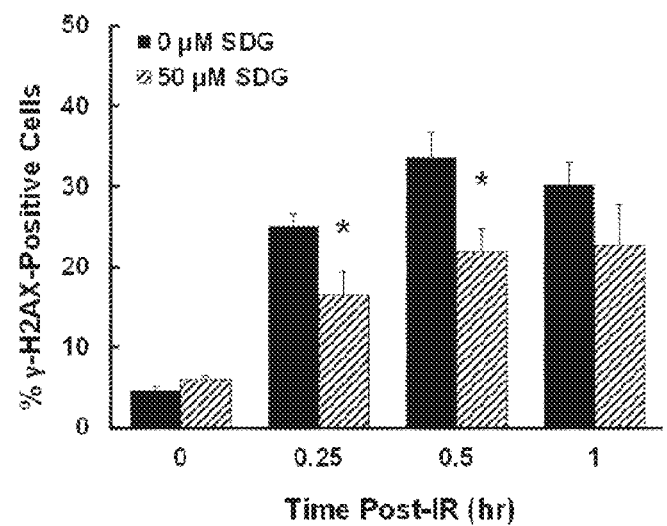
Figure 9C:
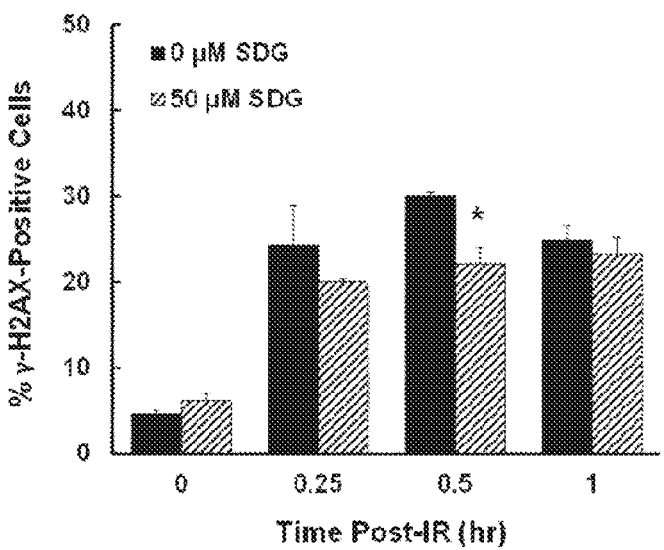

SDG Treatment Abrogates the Formation of γ-H2AX Foci in Murine Primary Lung Cells To further test our hypothesis whether SDG can protect against oxidative DNA damage, we also evaluated the action of SDG on induction of γ-H2AX foci. The effect of SDG pre-treatment on oxidative DNA damage, evidenced by γ-H2AX formation in murine primary lung cells after irradiation was evaluated using both standard microscopy-generated image analysis (FIGS. 9, 10) and flow cytometry (FIG. 11) methodologies. Results of fluorescence microscopic analysis show that radiation (2 Gy) exposure led to a significant increase in the formation of γ-H2AX foci in all three cell types (FIG. 9). The number of foci/cell increased substantially by 15 minutes, peaked at 30 min post irradiation (46.7%±0.5, 33.6%±3.2 and 30.0%±1.4 of γ-H2AX-positive cells, for epithelial, endothelial and fibroblasts, respectively) while numbers decreased notably within 1 h of exposure albeit still significantly higher than non-irradiated control cells. All values were significantly higher (FIG. 9) compared to their respective non-irradiated control cells ($p<0.005$ for all cell types).

Figure 10:
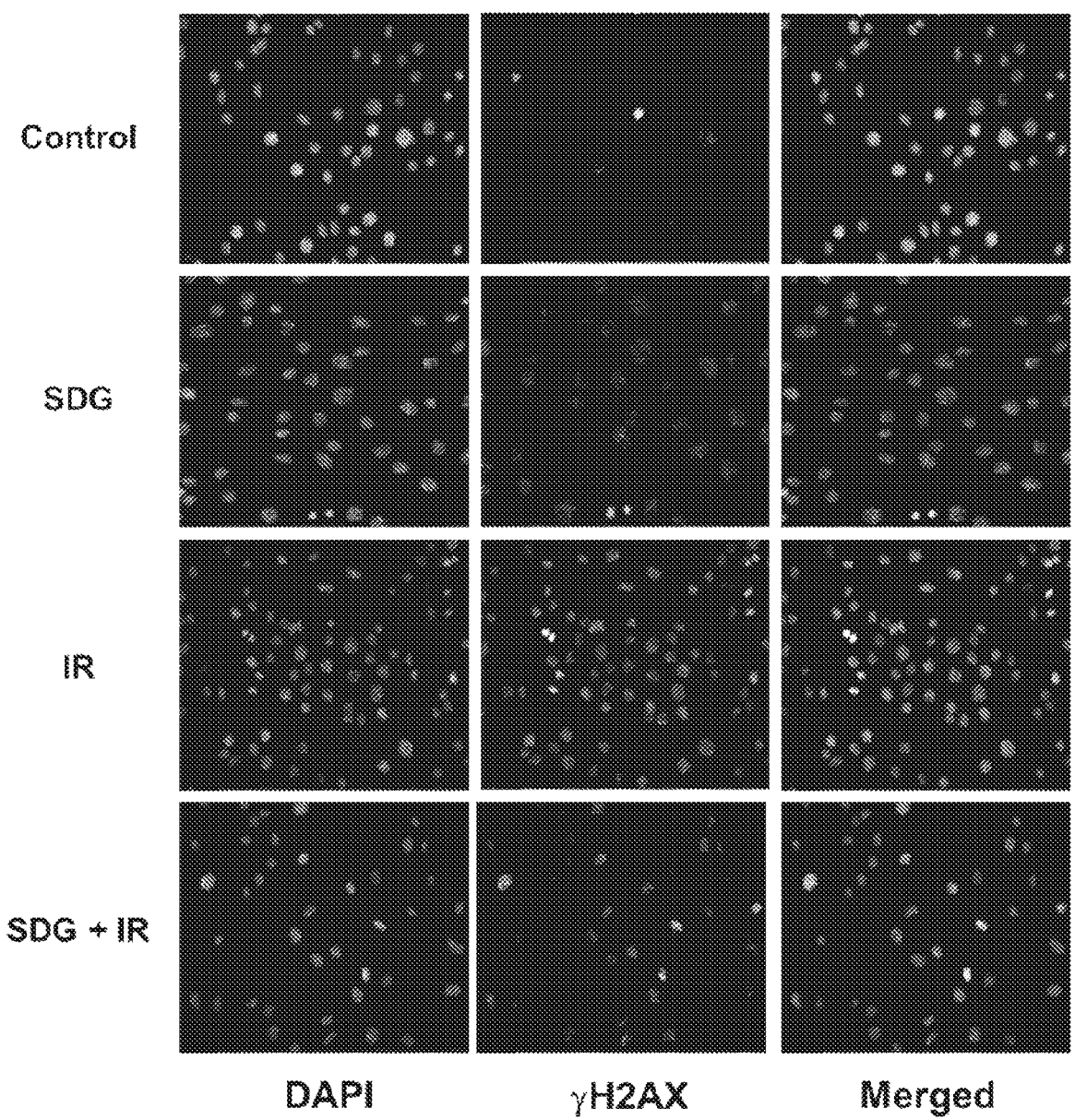
FIG. 10: Representative panels of immunofluorescence visualization of γ-H2AX foci (green) in murine lung epithelial cells. Cells were pre-treated with SDG for 6 h, gamma-irradiated (2 Gy) and incubated further for 30 min Cells were fixed in 4% paraformaldehyde and probed with γ-H2AX antibody. DNA was counterstained with DAPI (blue) Images were acquired using a fluorescence microscope.

SDG pre-treatment (6 hours prior IR) significantly decreased the induction of γ-H2AX, as the number of γ-H2AX positive cells decreased to 22.7%±2.17, 21.92%±2.88 and 22.1%±1.9 in irradiated epithelial cells, endothelial cells and fibroblasts, respectively ($p<0.005$ for epithelial, and $p<0.05$ for endothelial and fibroblasts). The ability of SDG to protect cells from the formation of γ-H2AX foci appeared to be independent of cell type as pre-treatment of SDG protected all three types of lung cells from radiation-induced DNA strand breaks. FIG. 10 depicts a representative fluorescence photomicrograph of microscopic analysis of γ-H2AX positive cells in primary lung epithelial cells.

Figure 11A:
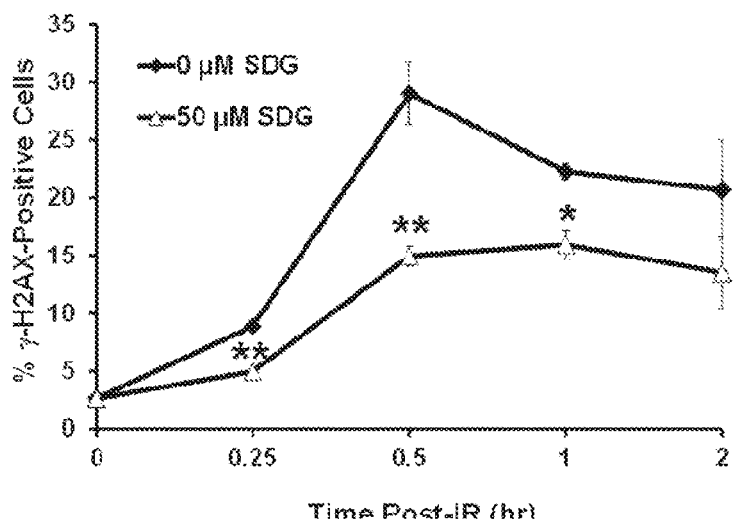
FIGS. 11A-11C: Flow cytometric (FACS) confirmation of the induction of γ-H2AX foci in irradiated murine primary lung cells. Primary lung cells viz. epithelial cells (FIG. 11A), endothelial cells (FIG. 11B) and WT Fibroblasts (FIG. 11C) were treated with SDG (50 µM) for 6 h and gamma-irradiated (2 Gy). At desired time interval, cells were processed for FACS analysis. Data was quantified using Summit software and is represented as mean±SEM. *p≤0.05, ** p≤0.01 for irradiated cells VS SDG pre-treated irradiated cells.
Figure 11B:
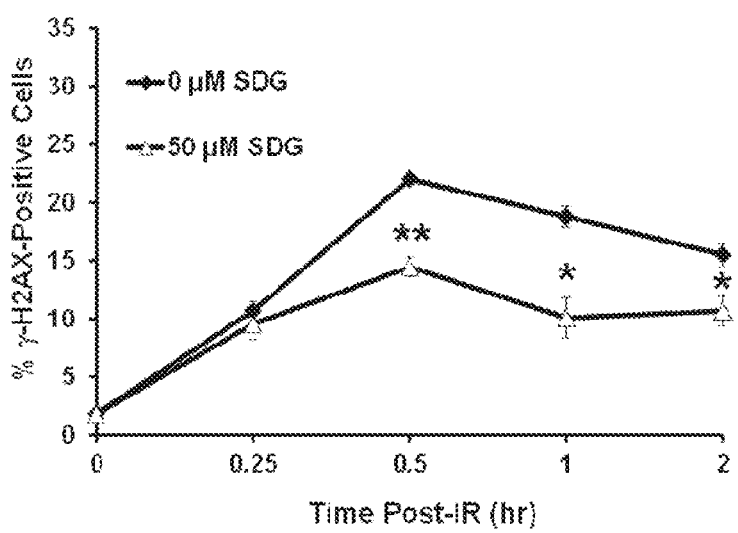
Figure 11C:
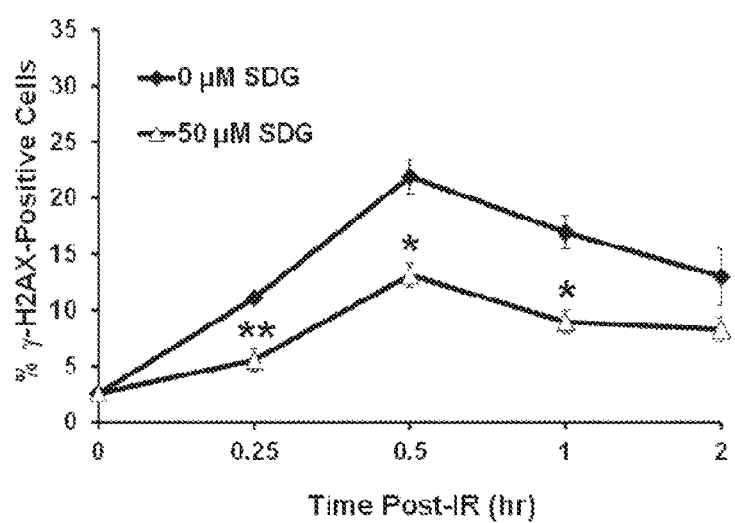

The protective effect of SDG on blunting the induction of γ-H2AX positive cells after radiation exposure was further confirmed using flow cytometry. As expected, a similar pattern in the induction of γ-H2AX positive cells was observed post-irradiation; however, number of γ-H2AX positive cells was significantly abrogated by SDG pre-treatment in all cell types (FIG. 11).

SDG Treatment Prevents Primary Lung Cells from IR-Induced Apoptotic Death

Figure 12A:
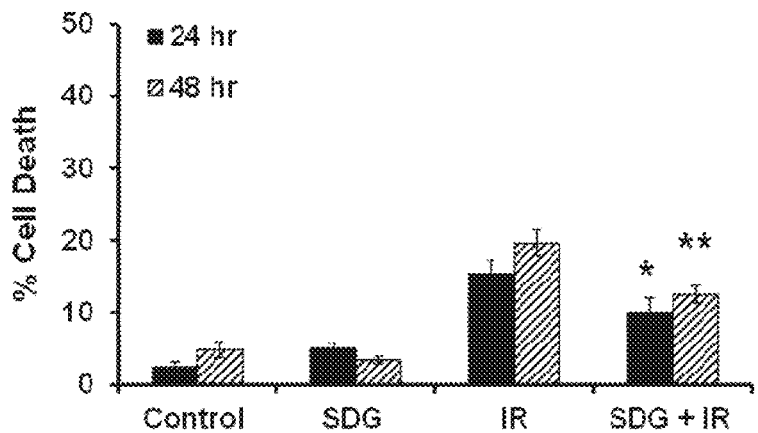
FIGS. 12A-12C: Evaluation of the radiation-induced apoptotic death in primary lung cells. Quantitative evaluation of the effect of SDG (50 mM) pre-treatment (6 h) on irradiated primary lung cells viz. epithelial cells (FIG. 12A), endothelial cells (FIG. 12B) and WT Fibroblasts (FIG. 12C). Cells were fixed, stained with DAPI and visualized for morphological analysis under fluorescence microscope. For each treatment, at least 500 cells were counted from 5 different fields and percentage of apoptotic cells was calculated. Experiment was done twice. Data is represented as mean±SEM. *p≤0.05, ** p≤0.005 for irradiated cells VS. SDG pre-treated irradiated cells.
Figure 12B:
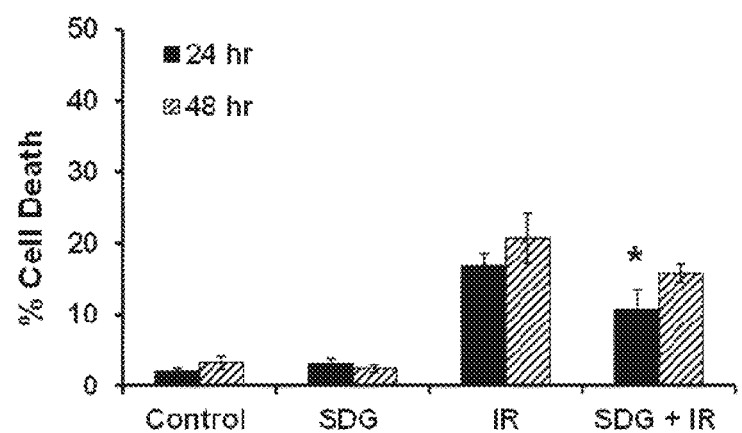
Figure 12C:
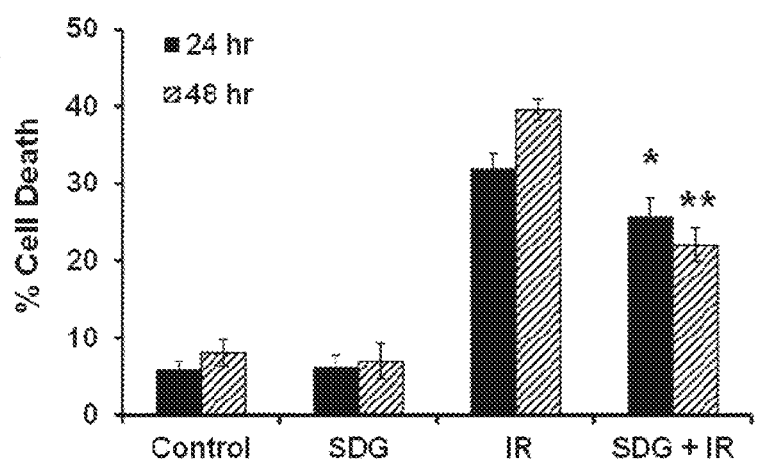

To study the cytoprotective effect of SDG in terms of apoptosis, nuclei were stained with DAPI for visualization by microscopy and counted. The microscopic analysis demonstrated that the control cells had intact chromatin (apoptotic cells ~4-5%), whereas radiation exposure significantly ($p≤0.05$) increased the percentage of apoptotic cells in a time and dose dependent manner. At 24 h, percentage of apoptotic cells was observed as 13.9%±1.08 and 15.1%±1.95 in epithelial and endothelial cells, respectively. SDG pre-treatment (50 μM) significantly ($p≤0.05$) countered the IR-induced increment in the percentage of apoptotic cells (9.9%±1.08 and 10.71%±1.45 apoptotic cells in epithelial and endothelial cells, respectively) as evident in FIGS. 12A and 12B). Fibroblasts were found to be most sensitive as radiation exposure led to notable 36.4% and 41.8% enhancement in apoptotic cells at 24 and 48 hr, respectively. Importantly, as shown with epithelial and endothelial cells, pre-treatment with SDG significantly reduced the extent of apoptosis in lung fibroblasts also (FIG. 12C).

Figure 13A:
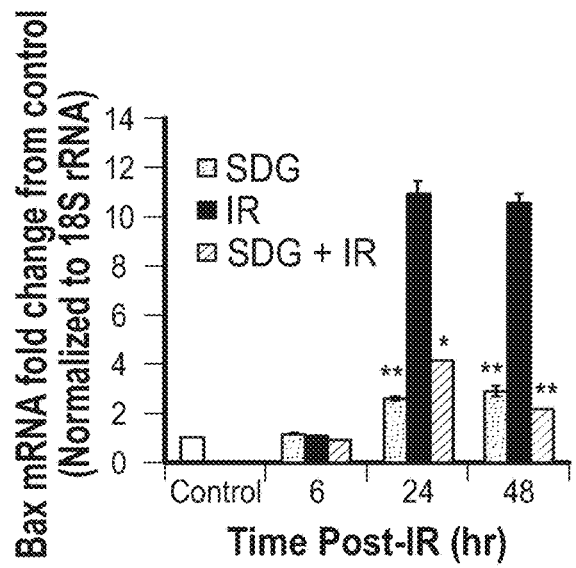
FIGS. 13A-13E: Evaluation of the effect SDG treatment on regulators of apoptosis in lung epithelial cells. Murine primary lung cells (epithelial cells) were treated with SDG (50 µM) for 6 hours prior to 2 Gy exposure. Cells were harvested at 6, 24, and 48 hours post-irradiation. Total RNA was isolated from epithelial cells at desired time interval and evaluated by quantitative real time RT-PCR analysis for Bax and Bcl-2 gene expression (FIGS. 13A and 13B). Analysis was performed in triplicate and gene expression was normalized to 18S ribosomal RNA. Bax and Bcl-2 protein levels were assessed by western blot analysis; representative images (FIG. 13C) and densitometry analysis with normalization to β-actin.
Figure 13B:
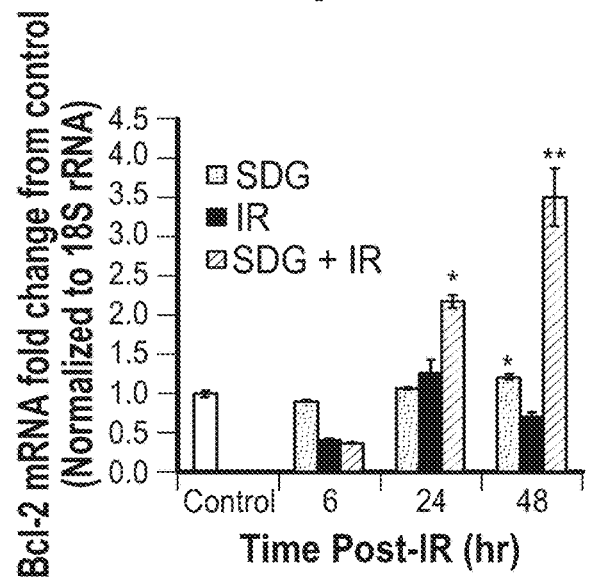
Figure 13C:
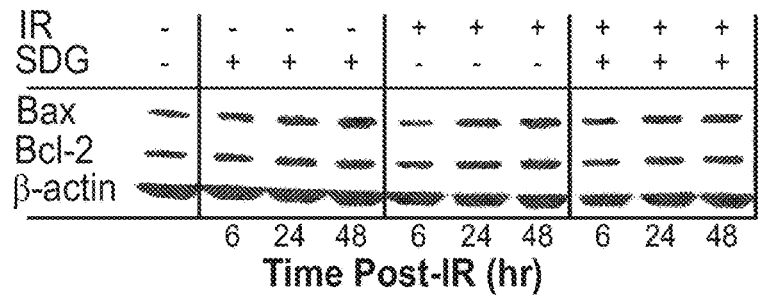
Figure 13D:
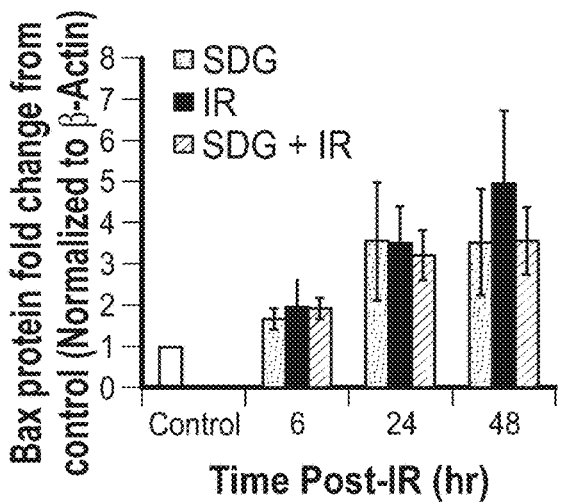
Figure 13E:
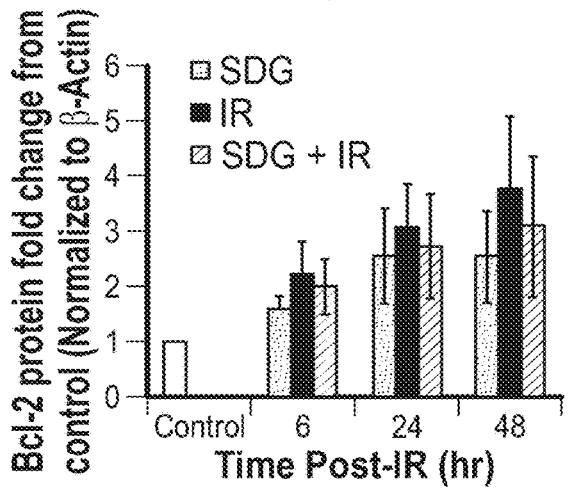
Figure 14A:
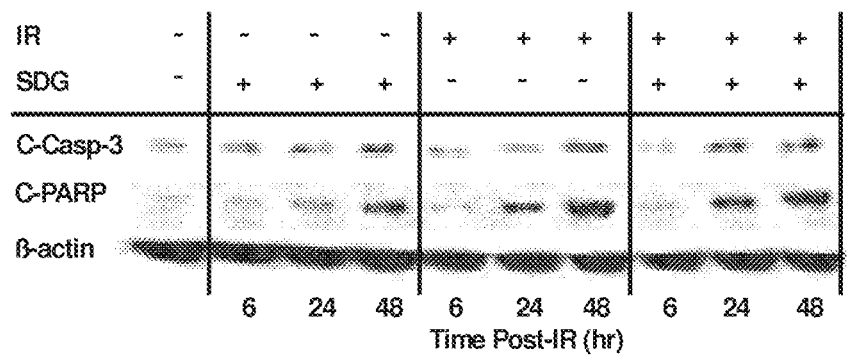
FIGS. 14A-14C: Effect of SDG on radiation induced increases in levels of active caspase-3 and cleaved PARP. Murine primary lung cells (epithelial cells) were treated with SDG (50 µM) for 6 hours prior to 2 Gy exposure. Cells were harvested at 6, 24, and 48 hours post-radiation. Cleaved caspase-3 and cleaved PARP protein levels were assessed by western blot analysis.
Figure 14B:
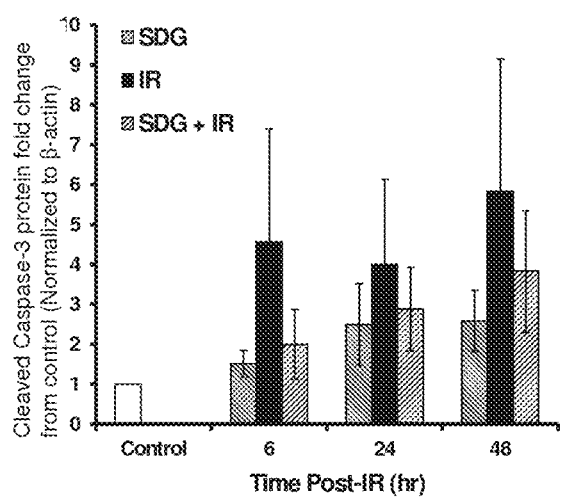
Figure 14C:
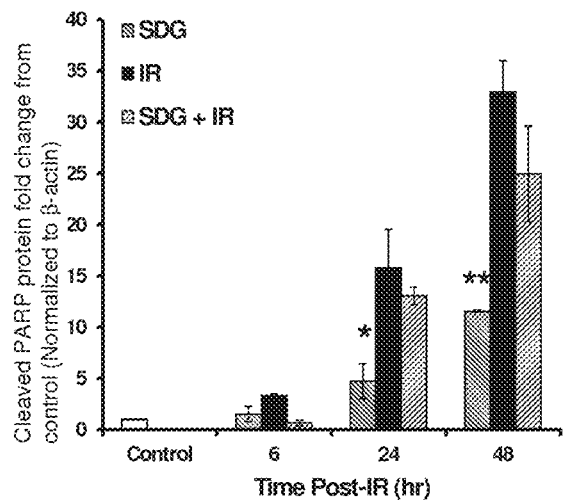

SDG Treatment Modifies the Expression of Regulators of Apoptosis in Murine Primary Lung Epithelial Cells In order to further elucidate the radioprotective effects of SDG in blunting DNA damage and cell death, we hypothesized that SDG may shift the ratio of pro-apoptotic and anti-apoptotic regulator proteins. We therefore tested whether SDG treatment of lung cells in the presence or absence of radiation would modify the gene expression of Bax and Bcl-2 and whether these changes would translate to changes in protein levels. For this, lung epithelial, endothelial and fibroblast cells were treated with SDG (50 μM) and enzyme mRNA levels evaluated at 6, 24, and 48 hours post-IR (FIGS. 13A and 13B) by qPCR. We observed that 2 Gy led to an approximate 11 fold increase in pro-apoptotic Bax mRNA levels at 24 and 48 hours post-IR, which was significantly ($p<0.05$) inhibited by SDG pre-treatment. Alternatively, anti-apoptotic Bcl-2 mRNA levels were not altered due to radiation exposure, yet increased 6.6 and 3.5 fold in SDG pre-treated cells at 24 and 48 hours post-IR treatment, respectively. Upon protein validation by western blot analysis of changes in Bax and Bcl-2 mRNA levels, we found subsequent increases in both Bax and Bcl-2 protein levels that trended towards decreased levels in SDG pre-treated cells (FIG. 13C depicts representative blots and 13D and 13E show band density quantification). To further investigate the underlying mechanism behind the observed radioprotection by SDG, we evaluated the effects of SDG in modifying levels of key protein implicated in the apoptotic signaling cascade: executioner cleaved caspase-3 and cleaved PARP. Overall, levels of cleaved caspase-3 and cleaved PARP were significantly increased in irradiated cells at 6, 24, and 48 hours post-IR and trended towards decreased levels in SDG pre-treated cells (FIG. 14A depicts representative blots and 14B and 14C show band density quantification).

Discussion

In this example, we demonstrated that FS lignan SDG can protect murine primary lung cells against radiation-induced oxidative DNA damage and apoptotic death. We observed that SDG pre-treatment not only improved IR-induced cytotoxicity as measured by clonogenic survival, but also decreased the induction of DNA strand breaks (DSBS and SSBS) and cell death in lung cells. Importantly, expression of genes implicated in the regulation of apoptosis was also altered by SDG treatment. These findings suggest that SDG may be useful as a non-toxic radioprotective agent in radiation scenario and in improving the therapeutic indices of radiotherapy.

IR-induced cell death is a classical marker of cellular radiosensitivity, which is characterized by loss in clonogenic survival. Similarly, we also noticed a radiation dose dependent loss in clonogenicity in all three murine lung cells which was attenuated significantly by SDG pre-treatment (FIG. 7). Cellular DNA is the primary target of IR-induced damage in the cell. ROS generated during exposure induces an array of changes in cellular DNA ranging from mutations, base lesions, cross-linking, SSBs and DSBs. Damage in DNA cannot be replaced and thus must be repaired and if it remains unrepaired, the cell may resort to induction of apoptosis or necrosis. Therefore, the protection of target cellular DNA confers the first line of defense against genotoxic insults. ROS generation occurs within seconds of exposure and persists for few minutes post-irradiation. Thus early radiation responses such as immediate DNA damage occur within minutes after radiation exposure. Similarly, in time dependent kinetic studies of irradiated cells, we also observed that extent of DNA strand breaks, as evidenced by comet tail length, reached to their maximum level within 30 minutes of exposure and lessen down thereafter (FIG. 8A).

The comet assay is a sensitive technique for the detection of DNA damage/repair at the cellular level and has been used widely to investigate DNA strand breaks. Polyphenols have the ability to protect normal tissue or cells from damaging effects of radiation by reducing ROS mediated oxidative DNA damage. In the present study, by employing standard alkaline comet assay, we also evaluated the role of SDG against IR-induced SSBs in murine primary lung cells. Our results are concordant with other reports that show a similar protective effect from radiation-induced DNA SSB for other phenolics such as, chrysin and epicatechin.

While SSBs are easily repaired by the cell, DSBs are more difficult for cells to repair and are more likely to result in mutagenesis, hence DSBs represent mostly the lethal cellular event. H2AX molecules become phosphorylated (γ-H2AX) along megabase-long chromatin domains for each DNA double-strand break introduced by irradiation and γ-H2AX loss or de-phosphorylation correlates time-wise with DNA repair. We report here that SDG protected cellular DNA from IR-induced DSBs in all three types of cells tested. Our results are in agreement with some other studies which also show that polyphenols like Resveratrol and green tea catechin protect cells from IR-induced DNA strand breaks. However, in the absence of radiation, SDG did not exert any toxic effect in either of these cells. As oxidative DNA damage is considered to be a precursor to many cancers, a reduction in such damage by SDG acting as antioxidant may lead to reduced risk of cancer.

It is well known that IR-induced apoptosis in cells and tissues is due in part to the induction of DNA damage in cells. Though several mechanisms (O6-methylguanine, base N-alkylations, bulky DNA adducts, DNA cross-links) are involved in DNA damage-dependent apoptosis, DNA double-strand breaks play a major role in inducing apoptotic cell death. In this study pre-treatment of cells with SDG protected against radiation-induced apoptosis in lung cells and inhibited comet tail length and γ-H2AX foci formation. Thus, the protective effects of SDG against radiation-induced apoptotic cell death could be attributed to its ability to reduce cellular oxidative stress, restoration of ionic homeostasis and its ability to prevent DNA damage. These findings are in agreement with the anti-apoptotic properties of dietary wholegrain flaxseed in our murine studies of ischemia-reperfusion and radiation-induced tissue damage and point to the SDG as the likely bioactive component in flaxseed mediating the protective, anti-apoptotic effects in tissues.

Because IR reduces the level of antioxidant enzymes in cellular milieu, the pre-treatment of cells by an antioxidant might further interfere with ROS and thereby decreasing the risk of interaction of ROS with bio-molecules. In the previous example, we have reported earlier that pre-feeding of animals with a diet containing flaxseed lignan complex increased the levels of protective phase II antioxidant enzymes in mouse lungs. The postulated mechanism for these actions involves the activation of antioxidant response element (ARE) mediated transcriptional induction. Further, Nrf2 also initiates the de novo synthesis of various antioxidant enzymes responsible for protection against oxidative stress mediated cytotoxicity. Some other reports also suggest that polyphenols like curcumin and EGCG exert protective effects against oxidative stress which is implicated by their ability to induce phase II antioxidant enzymes.

It is evident from the results that SDG reduces cell death in murine primary lung cells owing to its antioxidant properties and protective effects on DNA. Our findings corroborate with the results of Hseu et al (*Food Chem Toxicol* 2012, 50:1245) who reported that ellagic acid, a polyphenol found in pomegranate, protects human keratinocytes against UVA-induced oxidative stress and apoptosis through the upregulation of the HO-1 and Nrf-2 genes. Our study provides novel evidence that the radioprotective action of SDG in combating the IR-induced oxidative damage and apoptotic cell death may be by direct induction of the antioxidant defense system.

Taken together these results demonstrate that the flaxseed lignan SDG in flaxseed has potent radioprotective properties that likely contribute to the observed protective effects of the wholegrain in animal studies.

Example 3

Secoisolariciresinol Diglucoside (SDG) Scavenges Hypochlorite Ions: A Novel Mechanism of SDG Protection of Genomic DNA from Radiation Hypochlorous acid (HOCl), a potent oxidant, is produced by neutrophils by activated myeloperoxidase which catalyzes the reaction between physiologically present chloride ions and hydrogen peroxide ($H_2O_2$). Activated neutrophils produce $H_2O_2$ and superoxide anion $O_2^{\bullet-}$. At physiological pH, a mixture of both HOCl and hypochlorite ion ($ClO^-$) exists. HOCl kills microorganisms by oxidative damage. However, excessive production is known to cause damage to tissues. Hypochlorite modifies adenine nucleotides resulting in formation of chloramines that appears to be a major mechanism of neutrophil-mediated toxicity.

HOCl and its conjugated base $ClO^-$ have been shown to oxidize amino acids, peptides, proteins and lipids and to chlorinate bases in cellular DNA and RNA. The reaction of $HOCl/ClO^-$ results in modification of both purine and pyrimidine nucleotides at the endocyclic —NH groups of guanine and thymine as well as the exocyclic NH2 groups of guanine, adenine and cytosine derivatives resulting in the formation of chloramines such as (RNHCl) and RR'NCl. The primary modified bases were found to be 5-chlorocytosine, 8-chloroadenine and 8-chloroguanine in DNA and RNA of SKM-1 cells.

It is well known that γ-radiation is capable of ionizing atoms and molecules. In biological systems or in solution, ionizing radiation generates hydroxyl radicals (•OH) which are believed to be the source of ionizing radiation-induced damage to cellular components including lipids, proteins and DNA. However, these highly unstable radicals can be scavenged by $Cl^-$ ions which are present in the physiological medium at very high concentrations. This leads to generation of reactive chlorine-containing intermediates, among which relatively stable $ClO^-$ is the radiation-derived toxicant. In chloride-containing solutions, the $ClO^-$ and other active chlorine derivatives of oxidative nature are formed as products of radiolysis; they can contribute to suppression of physiological functions of organisms. Therefore, we propose that radiation-induced DNA or protein damage is mediated, in part, by radiation-generated $ClO^-$.

Chemically synthesized two diastereomers of SDG have recently been shown to be equipotent in their antioxidant, free radical scavenging and DNA protective properties. The present study evaluates SDG in DNA radioprotection from γ-radiation induced generation of $ClO^-$ in physiological saline solutions using highly novel and specific fluorescent probes. Hypochlorite-specific 3'-(p-aminophenyl) fluorescein (APF) and hydroxyl radical-sensitive 3'-(p-hydroxyphenyl) fluorescein (HPF) provide greater specificity and reproducibility for determination of the above reactive oxygen species (ROS).

Materials and Methods

Chemicals

ROS indicator probes APF and HPF, plasmid DNA (pBR322), and 1 kb plus DNA ladder were from Invitrogen (Life Technologies, Carlsbad, Calif.).

Determination of Hypochlorite

The fluorescence of ROS probes APF and HPF in PBS was measured at excitation/emission at 490 nm/515 nm in presence of hypochlorite or after γ-radiation exposure. Data is expressed as relative fluorescence units (RFU).

γ-Radiation-Induced Generation of Hypochlorite By Determining Taurine Chloramine Chlorination of taurine was determined using TMB assay. The data is expressed as taurine chloramine (absorbance) as well as $ClO^-$ concentration (μM).

Hypochlorite-Induced Damage to Calf Thymus and Plasmid DNA

Calf thymus or plasmid DNA was incubated with hypochlorite for 2 hrs at 37° C. DNA samples were subjected to agarose (1%) gel electrophoresis and analyzed.

Determination of Hypochlorite-Induced Chlorination of 2-Aminopurine (2-AP)

2-AP in PBS was exposed to hypochlorite and fluorescence spectra recorded between 360-390 nm with the emission maximum at 374 nm. The % change in 2-AP calculated.

Statistical Analysis of the Data

The data obtained are presented as mean values ±standard deviation. The data were subjected to one-way analysis of variance (ANOVA) with post-hoc comparison using Bonferroni correction using Statview Program. P value ≤0.05 was considered as significant.

Results

In this study we investigated the ability of SDG to scavenge radiation-induced $ClO^-$, as a potential mechanism of DNA protection from radiation exposure in physiological solutions.

SDG Scavenges Hypochlorite Ions

Figure 15A:
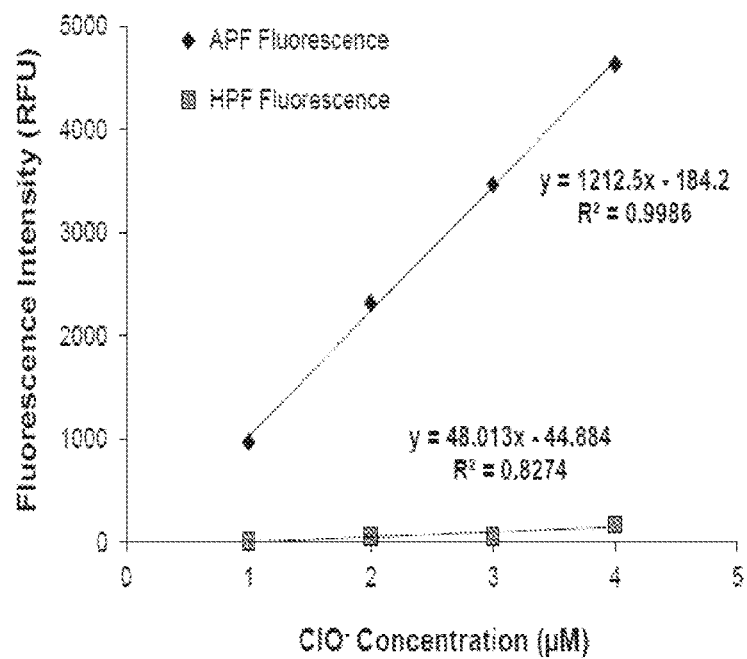
FIGS. 15A-15C: SDG Scavenges Hypochlorite Ions.
Figure 15B:
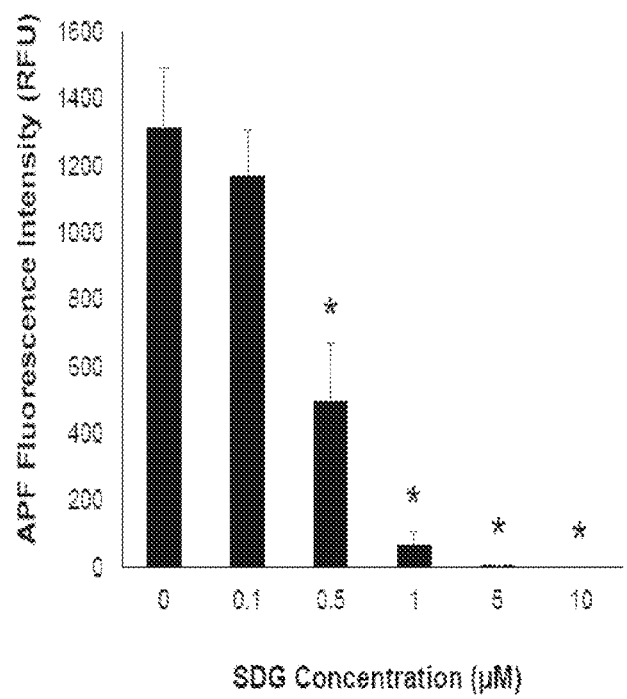
Figure 15C:
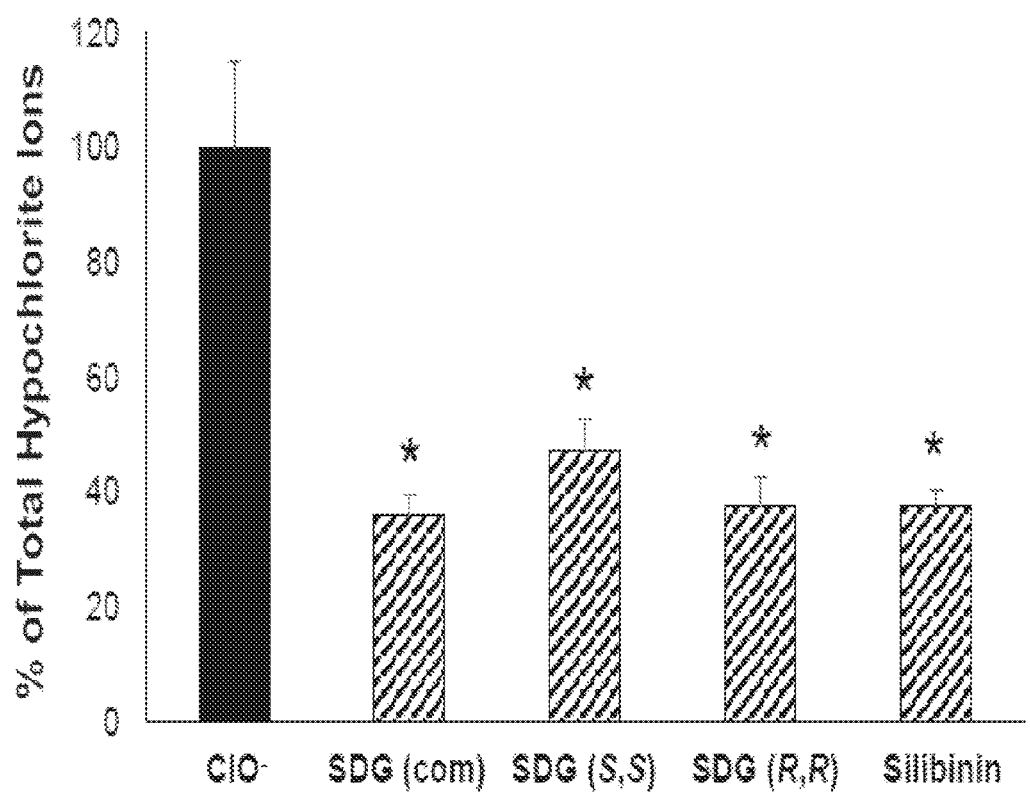

The specificity of the selected fluoroprobes was evaluated using sodium hypochlorite. FIG. 15A shows a linear increase in APF fluorescence intensity with an increase in $ClO^-$ concentration (1-4 µM). Importantly, HPF fluorescence intensity increased only marginally, indicating that APF fluorescence is mainly $ClO^-$-dependent. $ClO^-$ doses were selected to be within this range for subsequent experiments. The ability of SDG to scavenge $ClO^-$ by SDG (commercially available) was then evaluated. Indeed, SDG decreased $ClO^-$ dose-dependently (FIG. 15B). Lastly, we evaluated the $ClO^-$ scavenging effect of synthetic SDG diastereomers SDG(S, S) and SDG (R, R). At 0.5 µM, SDG (R,R) and SDG (S,S), and SDG (com) scavenged $ClO^-$ (FIG. 15C) with a comparable potency that was similar to silibinin, an established $ClO^-$ scavenger.

SDG Scavenges γ-Radiation-Induced Hypochlorite

Figure 16A:
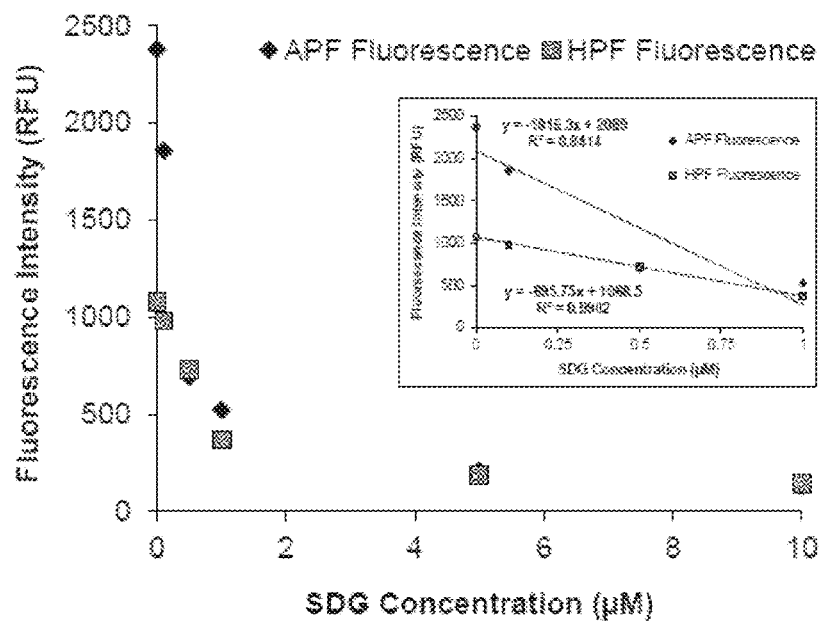
FIGS. 16A-16G: SDG Scavenges γ-Radiation-induced Generation of Hypochlorite.
Figure 16B:
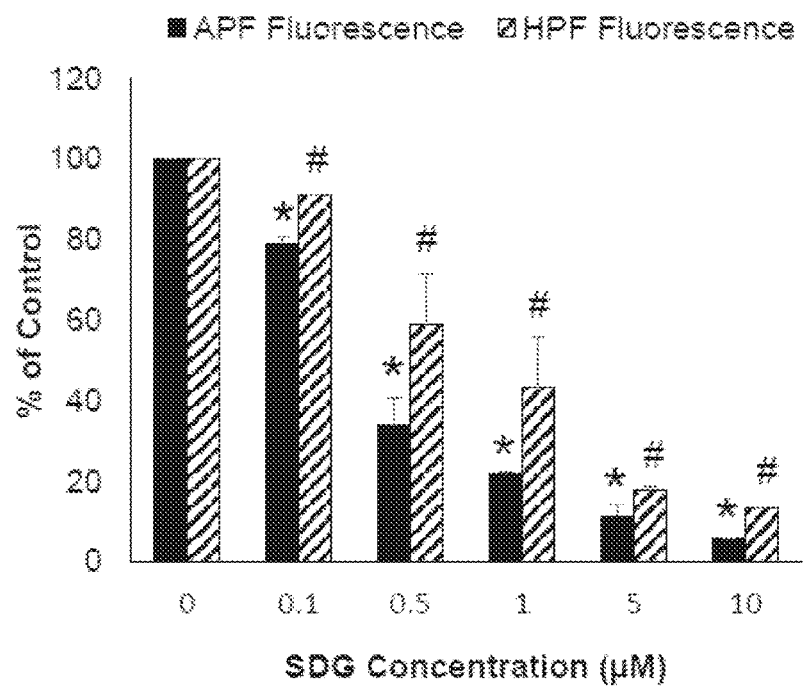
Figure 16C:
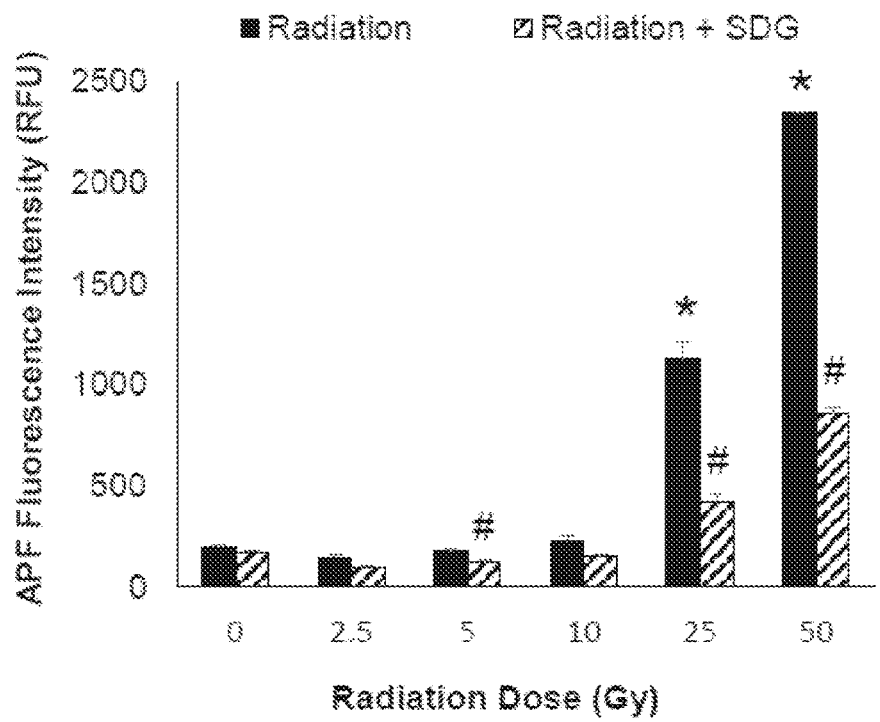
Figure 16D:
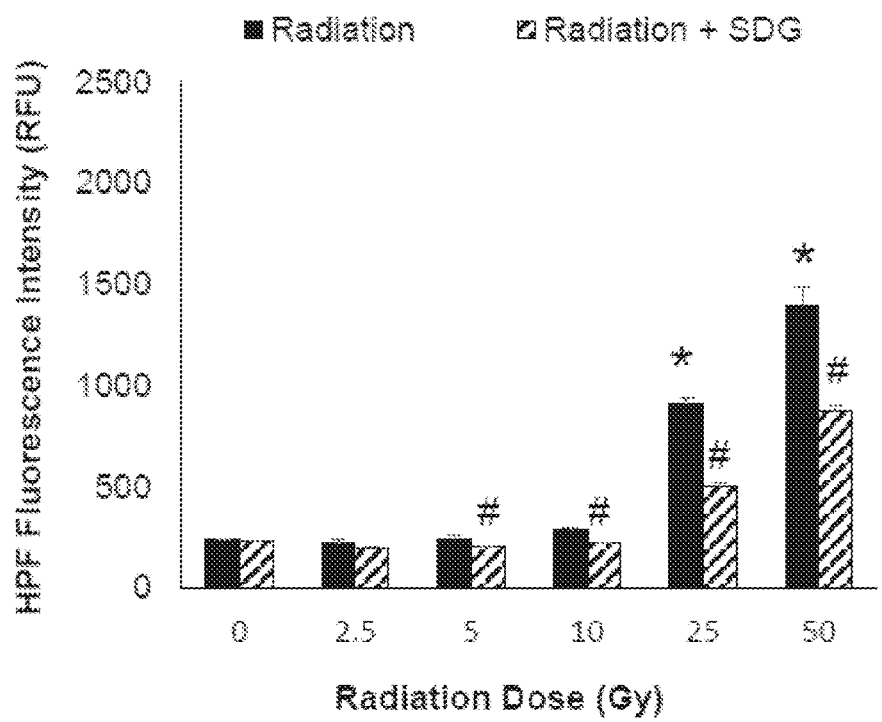

Radiation generates $ClO^-$ dose-dependently, as evidenced by an increase in fluorescence intensity of APF. Specifically, 50 Gy γ-radiation-induced APF and HPF (FIG. 16A) which was dose-dependently decreased by SDG (FIGS. 16A and B). The initial slope for decrease for APF fluorescence (1,816.30) was higher compared to HPF (695.75) indicating a selective scavenging effect of SDG on $ClO^-$ (insert, FIG. 16A). The effect of SDG on APF was significantly more pronounced as compared to HPF (FIG. 16B). SDG blunted $ClO^-$ generation from radiation exposure (25 and 50 Gy) shown by increased APF (FIG. 16C) and HPF (FIG. 16D) fluorescence (p<0.05). The ratio APF/HPF decreased by SDG indicating selective scavenging of $ClO^-$.

Radiation Dose-Dependent Increase in Hypochlorite as Chlorination of Taurine

Figure 16E:
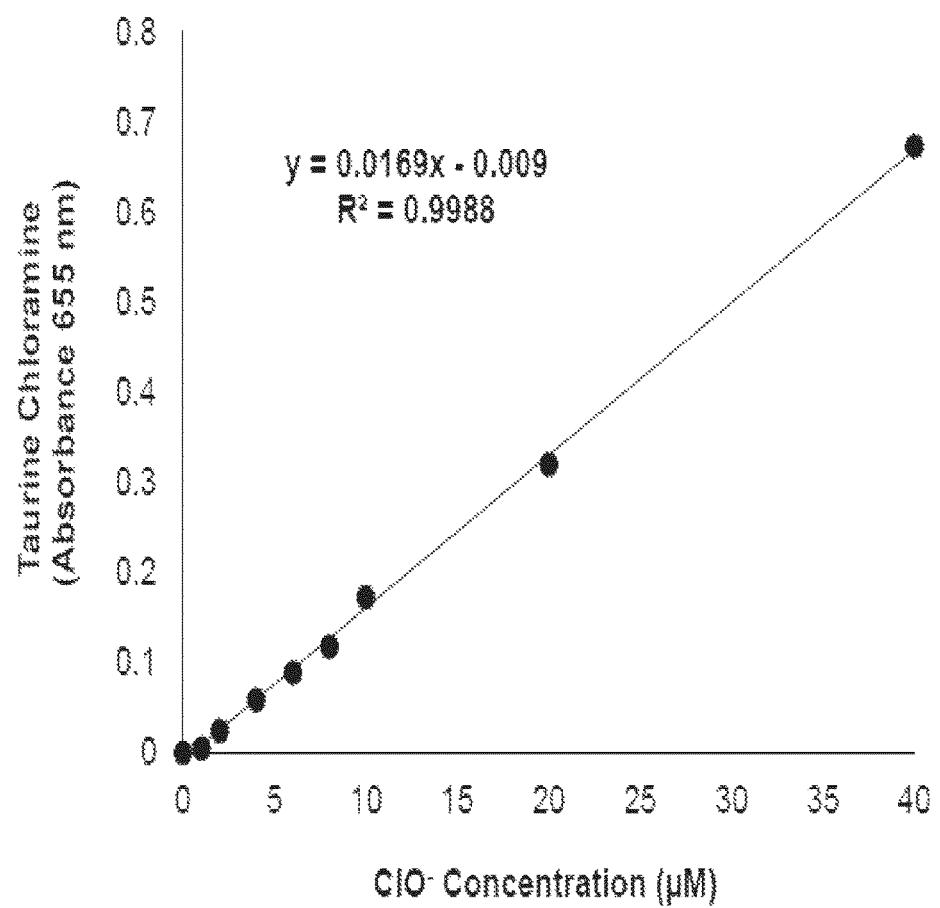
Figure 16F:
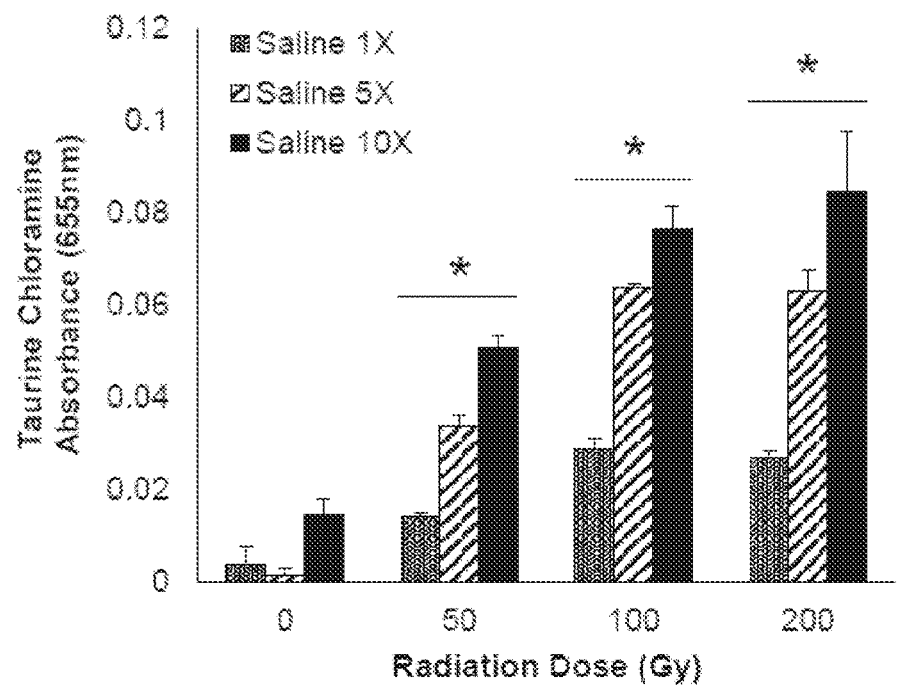
Figure 16G:
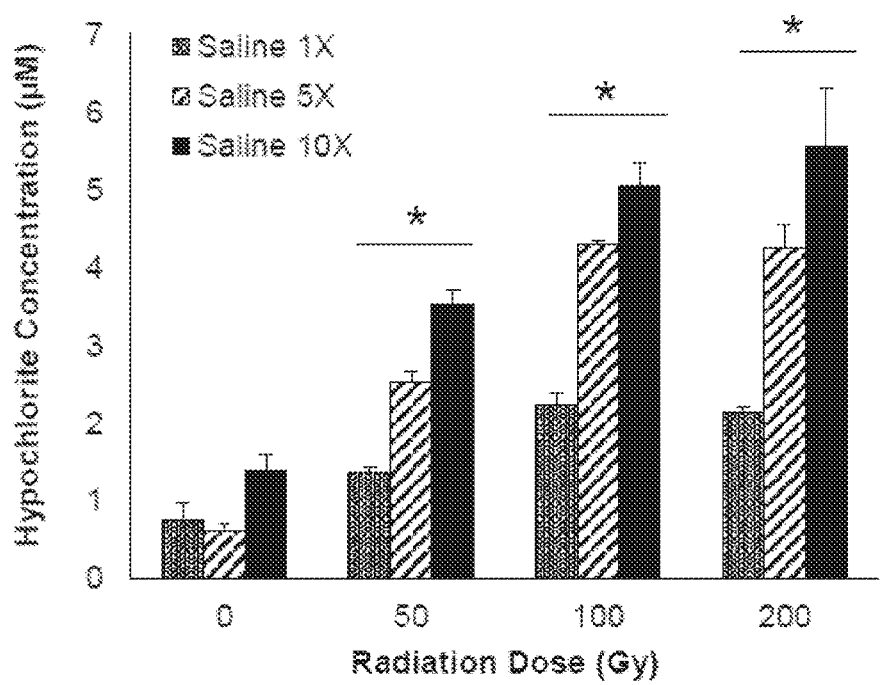

To establish that radiation-induced $ClO^-$ chlorinates—NH groups in biological molecules, we evaluated radiation-induced chlorination of taurine. The results (FIG. 16E) show that in normal saline, γ-radiation significantly increased taurine chloramine formation at 50, 100, and 200 Gy indicating that γ-radiation induces $ClO^-$ generation which was dependent in chloride concentration (FIG. 16F). The results provide strong evidence that radiation induces $ClO^-$ in a physiological solution, capable of damaging biomolecules.

SDG Protects Hypochlorite-Induced Damage to Calf Thymus and Plasmid DNA

Figure 17A:
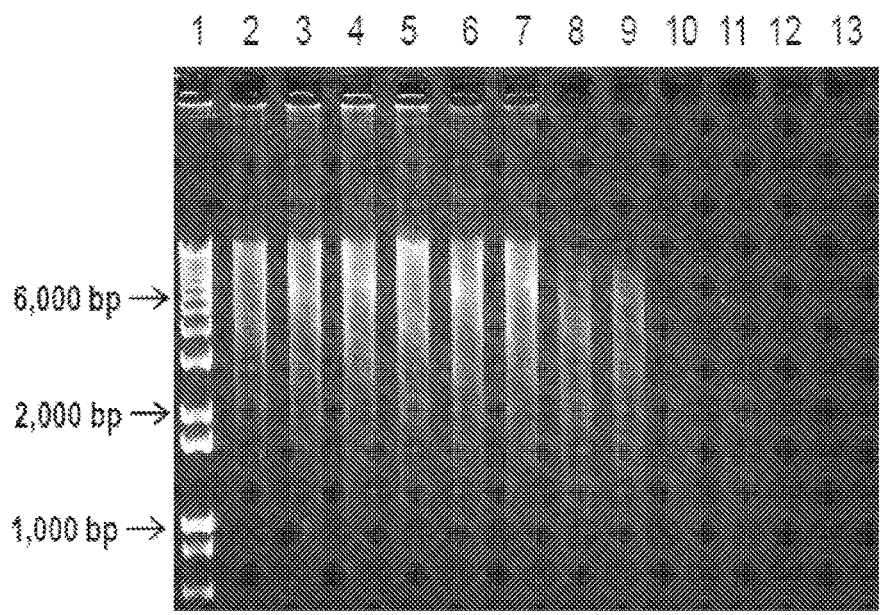
FIGS. 17A-17F: Hypochlorite-induced Calf thymus DNA Damage.
Figure 17B:
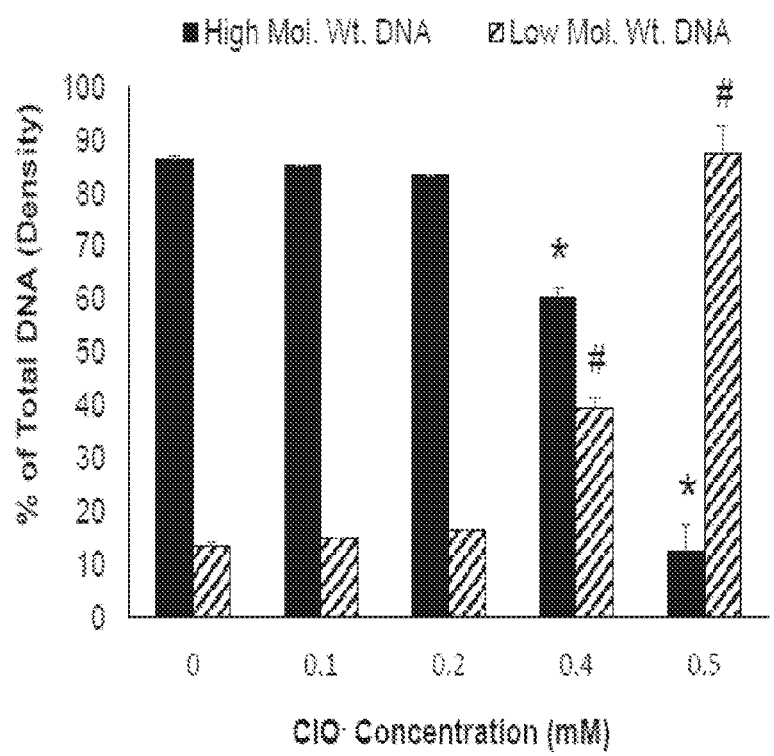
Figure 17C:
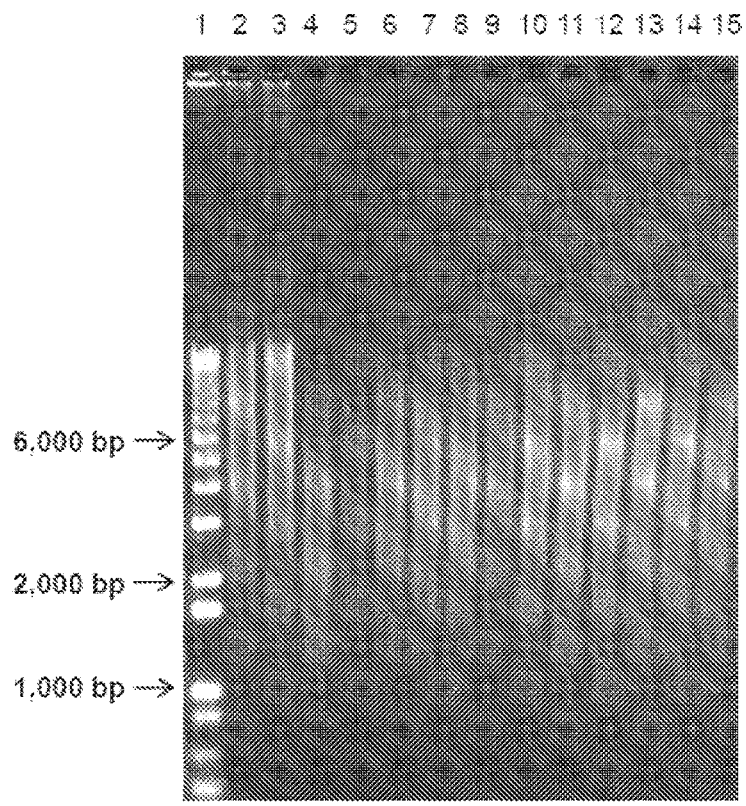
Figure 17D:
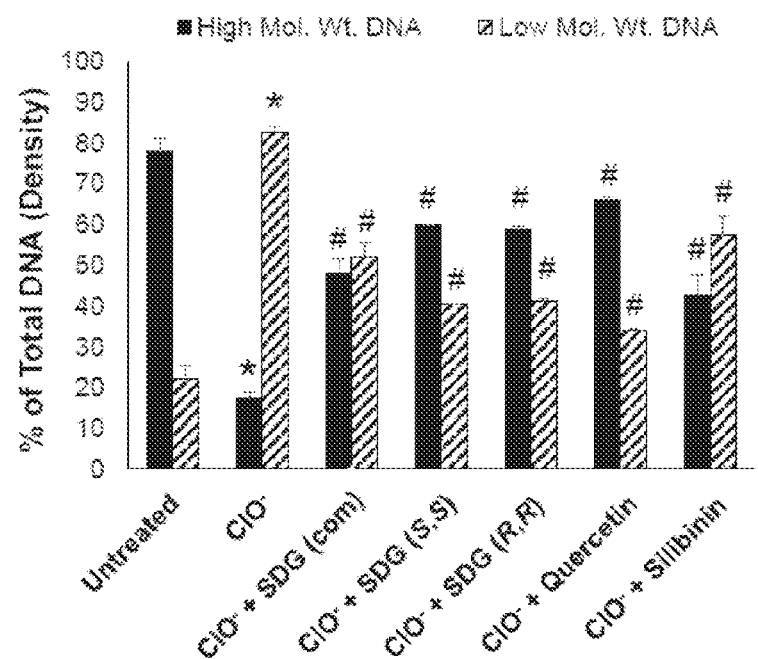
Figure 17E:
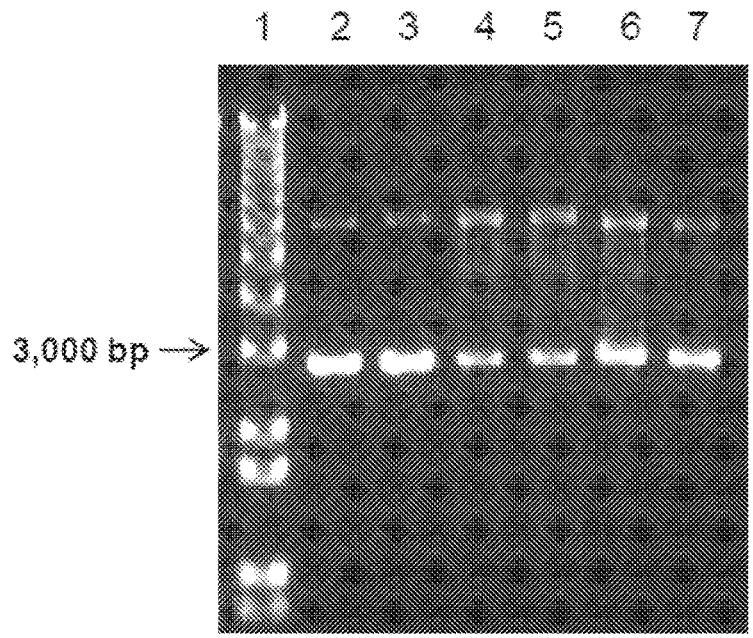
Figure 17F:
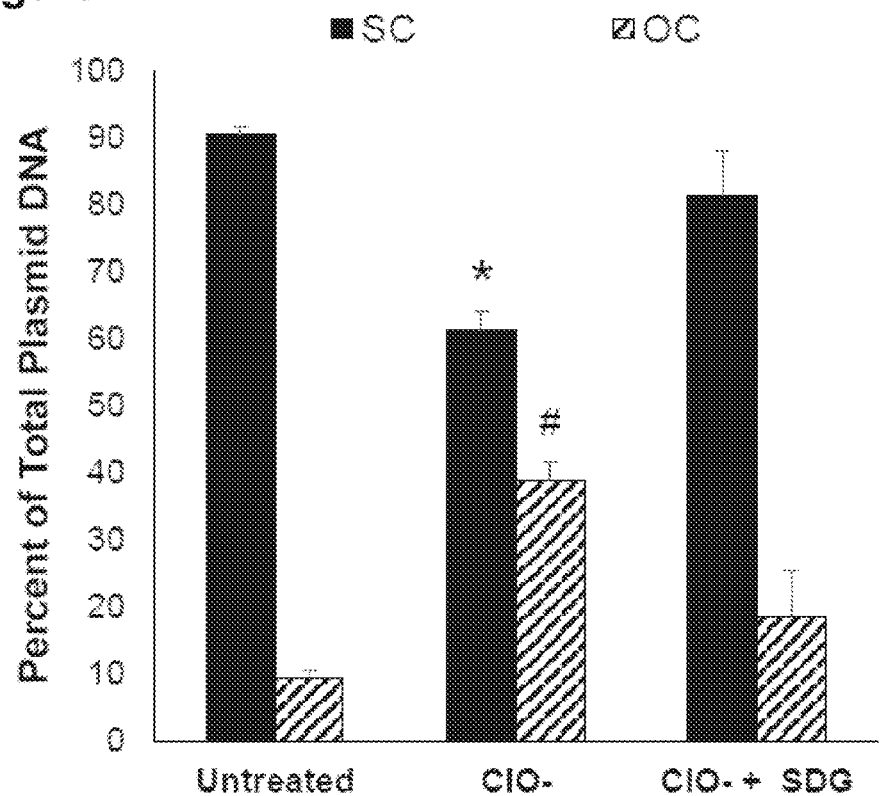

We determined whether $ClO^-$ induces damage to genomic (FIGS. 17A-17D) and plasmid (FIGS. 17E-17F) DNA. Indeed $ClO^-$ induces dose-dependent DNA fragmentation (FIGS. 17A, 17B) with an increase in low molecular weight fragments. Damage to genomics DNA exposed to 0.5 mM hypochlorite 1.0 µM was blunted by all SDGs (commercially available or synthetic), to levels comparable to quercetin, a known antioxidant and silibinin, a $ClO^-$ scavenger (FIG. 17C, 17D). Similarly, damage by $ClO^-$ to plasmid DNA was blunted by SDG (FIG. 17E, 17F). Specifically, we evaluated amounts of super coiled (SC) plasmid DNA as compared to damaged, open coiled-DNA which have a different mobility pattern in agarose gel electrophoresis. The presence of SDG at (25 µM) decreased the $ClO^-$-induced damage to plasmid DNA and preserved the DNA in mostly (81.3%±9.4%) super coiled form as compared to OC (18.6%±9.4%).

Protective Effect of SDG on Hypochlorite-Induced Chlorination of 2-AP

Figure 18A:
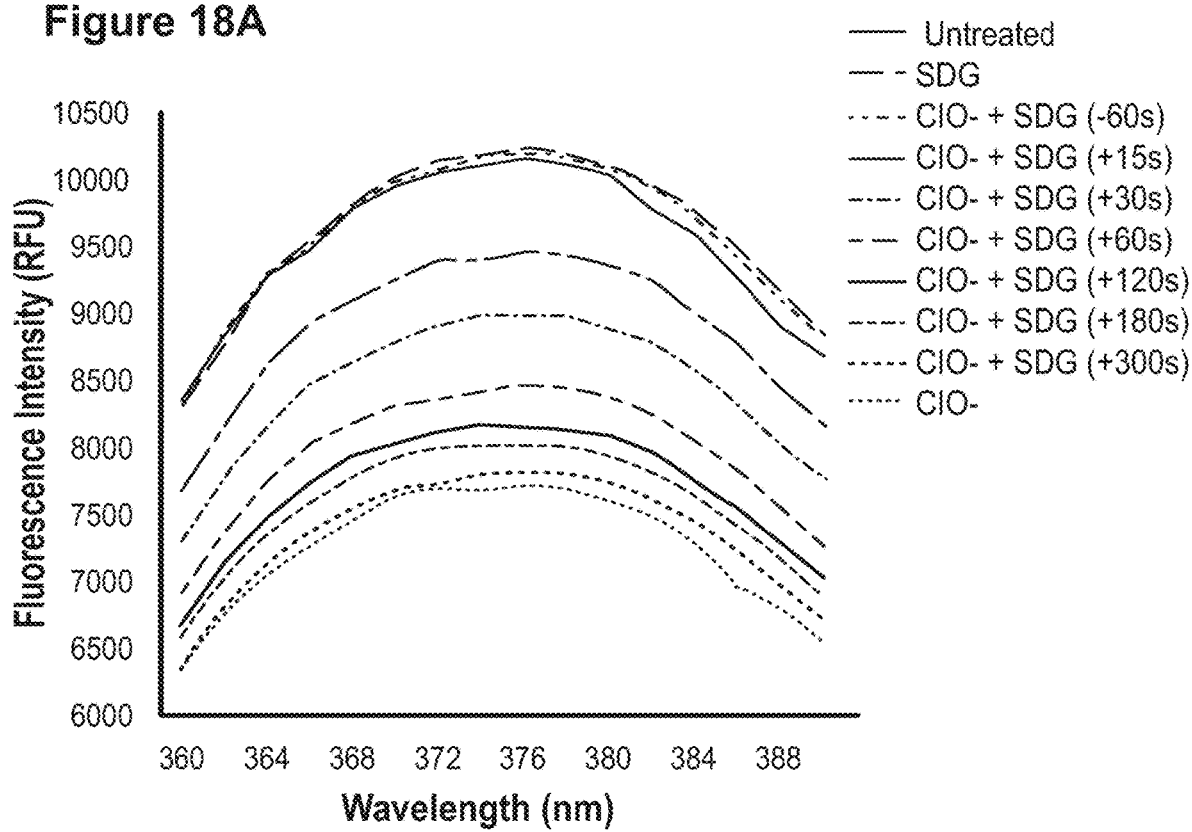
FIGS. 18A-18C: Effect of SDG (Pre- and Post-treatment) on Hypochlorite-induced Modification of 2-Aminopurine (2-AP).
Figure 18B:
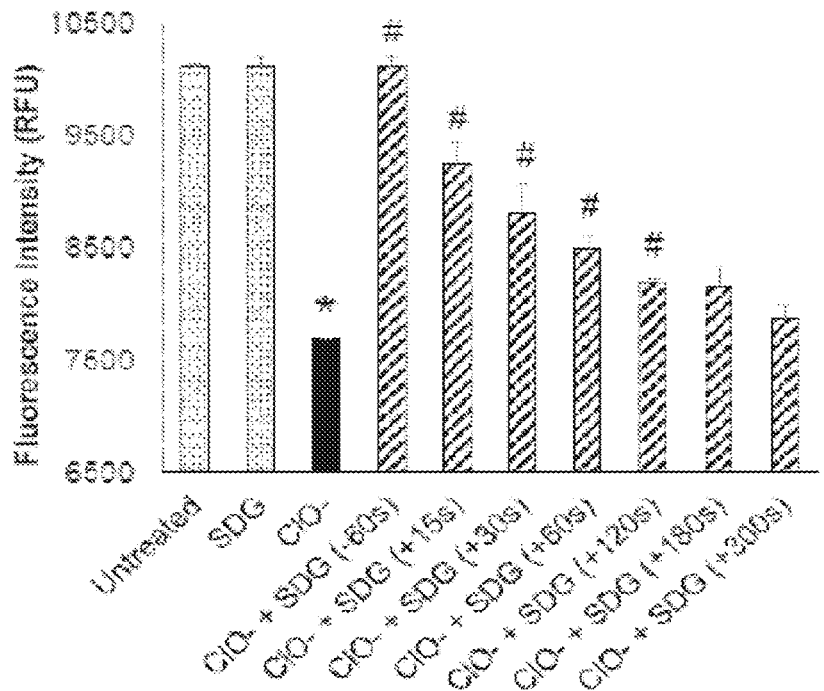
Figure 18C:
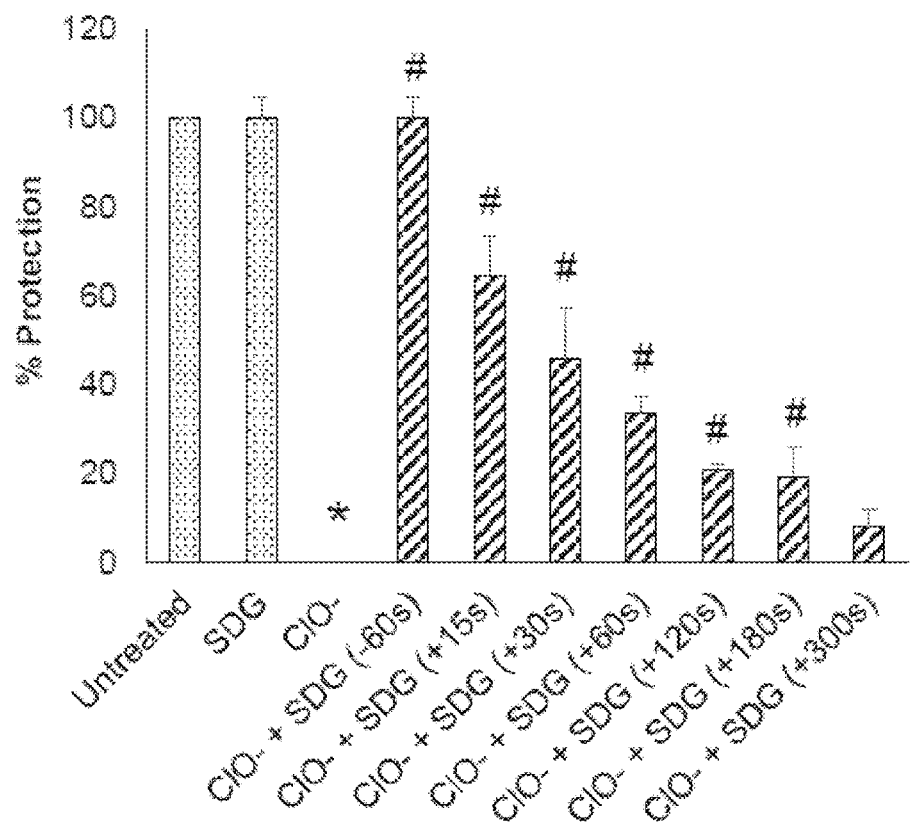

To determine whether the $ClO^-$ damage to DNA occurs by nucleobase modification, we evaluated $ClO^-$-induced chlorination of 2-AP, a fluorescent analog of purine. Hypochlorite, given at comparable concentrations (10 µM) to those generated by radiation exposure (FIGS. 15A, 16A, 17C) decreased 2-AP fluorescence which was prevented by pretreatment (60 seconds) with SDG (FIGS. 18A and 18B). Most importantly (FIGS. 18B and 18C), post-treatment with SDG resulted in significant recovery from hypochlorite-induced 2-AP modification if added at +15, +30, +60, +120, +180 or +300, seconds following the exposure to $ClO^-$. These results demonstrate the nucleobase protective characteristic of SDG against hypochlorite-induced modification of purine bases.

Protective Effect of SDG on γ-Radiation-induced Chlorination of 2-AP

Figure 19A:
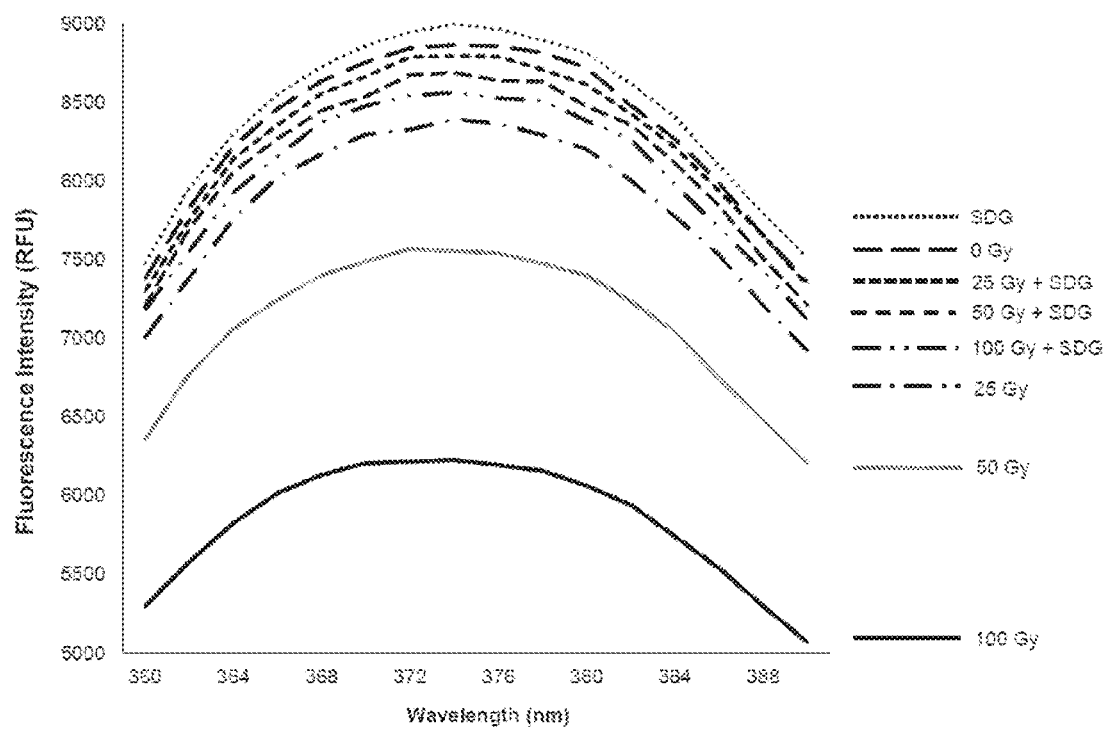
FIGS. 19A-19B: SDG prevents γ-radiation-induced modification of 2-aminopurine (2-AP).
Figure 19B:
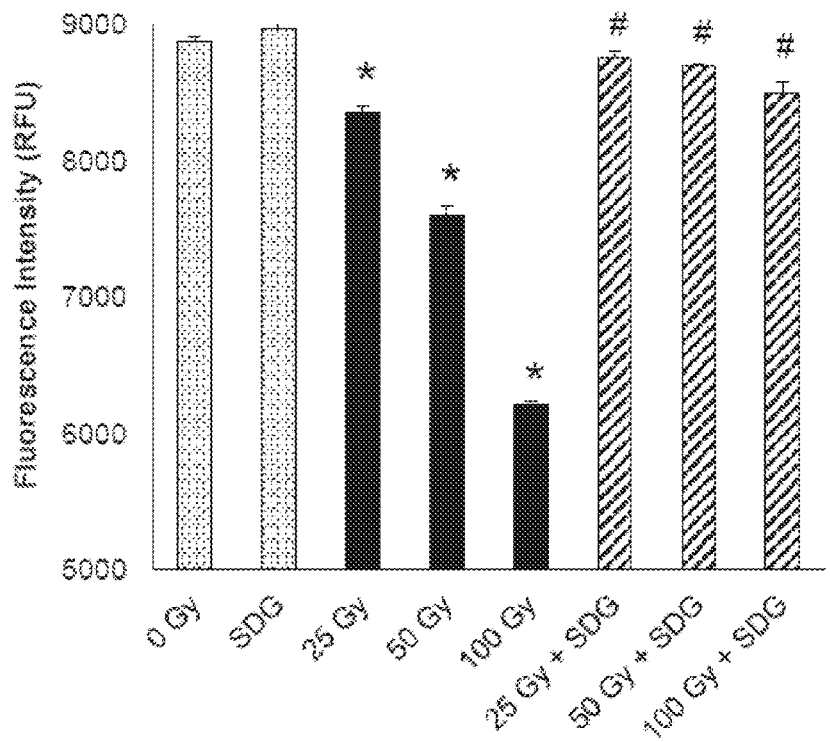

To determine whether radiation induces nucleobase chlorination, we used the same system as above, namely 2-AP fluorescence (FIG. 19A). Indeed, exposure to γ-radiation resulted in dose-dependent decrease in fluorescence intensity (an observation similar to that in presence of $ClO^-$, (FIG. 18A) which was prevented by SDG (FIGS. 19A and 19B). These results demonstrate that γ-radiation induces chlorination of a nucleobase and established protective properties of SDG against such radiation-induced modifications of purine bases.

Figure 20:
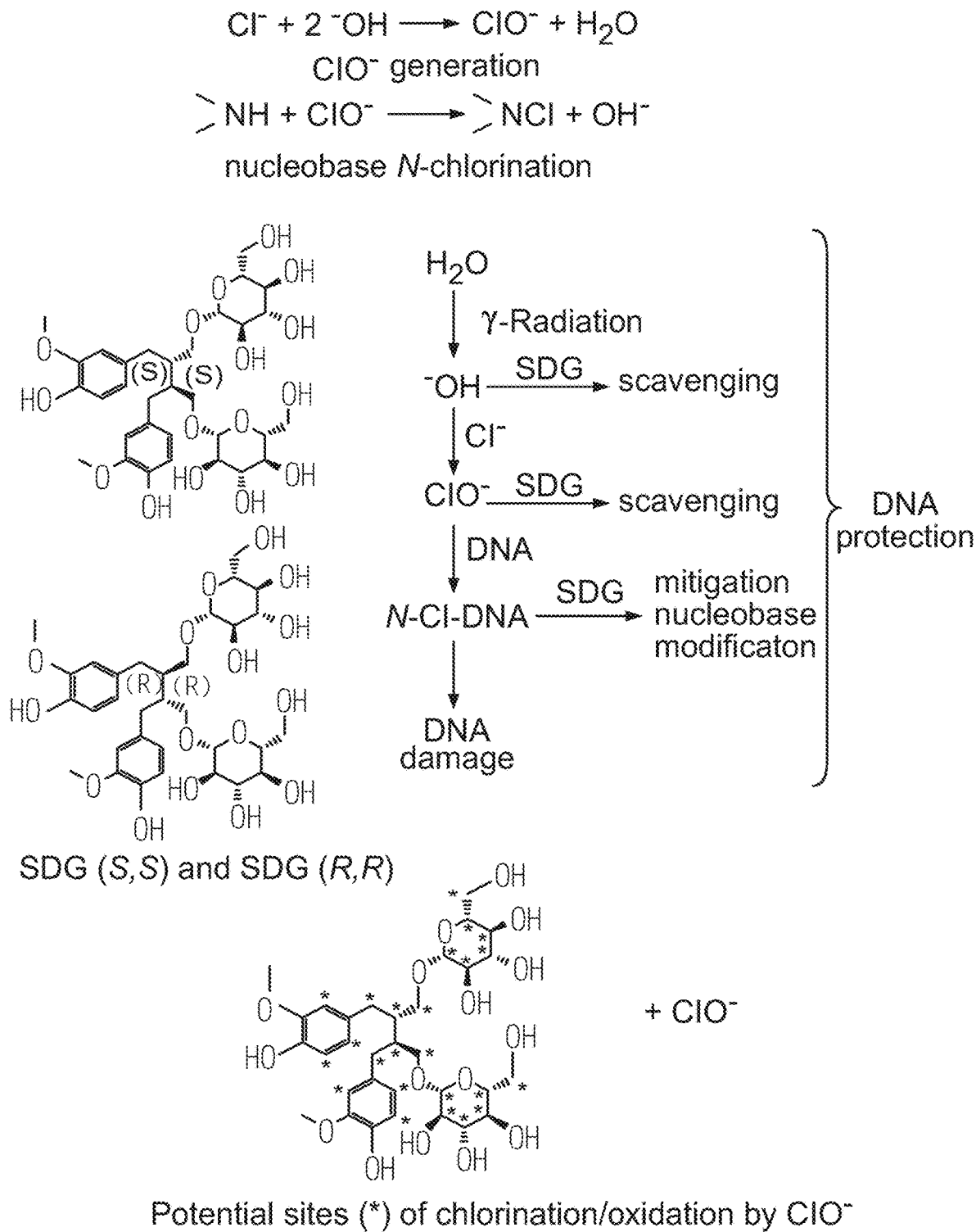
FIG. 20: Proposed mechanism of SDG action in DNA protection from nucleobase chlorination.

Proposed Mechanism of SDG Action in Preventing or Mitigating Nucleobase Chlorination by Radiation Regarding the mechanism of recovery or prevention of N-chlorinated nucleobases, we suggest either a two-electron reduction of N—Cl-molecules by electron-rich aromatic ring or a one-electron reduction, leading to formation of a free N-radical, which, in turn, captures hydrogen atom from —OH group in phenolic SDG moieties. Scheme 1 (FIG. 20) indicates the proposed mechanism of SDG protection. The results of our present study provide the evidence, for the new mechanism of radioprotective action of SDG by scavenging hypochlorite ions and protecting from radiation-induced DNA damage.

Discussion

The results of this study provide evidence for the following: i) SDG, a known lignan antioxidant and free radical scavenger, detoxified hypochlorite ions generated in physiological solutions by chemical means as well as by radiation; ii) SDG protected genomic DNA as well as plasmid DNA from hypochlorite-induced damage; iii) The mechanism of SDG defense (protection or recovery from hypochlorite-induced DNA damage), involves scavenging hypochlorite and regeneration of amino (—NH) groups on nucleobases from chloramines (—NCl); iv) Exposure to γ-radiation resulted in increased taurine chloramine formation; v) Exposure to γ-radiation resulted in increased chlorination of a purine base that was prevented by SDG; vi) SDG action is equally effective in protecting DNA from hypochlorite-induced damage when added prior to or post-exposure, i.e., it can act as a protector and/or mitigator of nucleobase chlorination; vii) Synthetic SDG (S,S) and SDG (R,R) diastereomers were equally potent in scavenging hypochlorite ions and preventing hypochlorite-induced DNA damage as compared to commercially available SDG, silibinin, and quercetin (a natural antioxidant flavonoid). These results demonstrate the protective and mitigating property of SDG for hypochlorite-induced modification of nucleobases.

Using a mouse model of thoracic radiation damage, we have established the tissue radioprotective role of whole grain dietary flaxseed, a grain rich in lignan polyphenols, as well as of flaxseed lignan formulations enriched in SDG. These studies emphasized the radioprotective and radiation mitigating properties of the lignan SDG against radiation-induced tissue damage in vivo. Extracted, purified or synthetic flaxseed SDG is a potent antioxidant in vitro as well as in vivo. In order to explore the therapeutic potential of SDG we have synthesized SDG by a novel chemical reaction and determined the antioxidant properties of the synthetic SDG (R,R) and SDG (S,S) by assessing their reducing power, metal chelating potential, and free radical scavenging activity for •OH, peroxyl and DPPH radicals. We also demonstrated the radioprotective characteristics of synthetic SDG (R,R), SDG (S,S) diastereomers by assessing their potential for preventing γ-irradiation-induced damage to plasmid DNA (pBR322) and calf thymus DNA.

We have also showed that the maximum radioprotection of genomic DNA by SDG is already achieved at approximately 5.0 µM concentration which is below the EC50 values for their free radical scavenging and antioxidant effects, typically in the range of 130-200 µM. It is interesting to note that the maximum effectiveness of SDG in scavenging radiation-induced hypochlorite as determined in this study, falls within 0.5 to 5 µM. This suggests that the DNA-protective effects of SDG are due in part to scavenging of damaging ClO$^-$. The results showing the protective effect of SDG on hypochlorite-induced modification of 2-AP indicate that SDG protects DNA by preventing hypochlorite-induced damage to the nucleobases.

HOCl is produced by myeloperoxidase of activated neutrophils using hydrogen peroxide generated by NADPH oxidase and chloride ions as substrates. HOCl can chlorinate and oxidize nucleobases. Since HOCl can chlorinate nucleobases, this might cause genotoxicity. Chlorinated nucleosides have been identified and linked to inflammation and cancer.

There could be several potential mechanisms by which SDG may protect DNA from radiation-induced damage: 1) by scavenging hypochlorite ions that cause chlorination and oxidation of nucleobases; 2) by scavenging •OH free radicals that produce hypochlorite by reacting with chloride ions. We observed that the production of •OH was drastically decreased in the presence of chloride ion in phosphate buffered saline (PBS) as well as in saline alone (preliminary experiments). Considering the high concentration of chloride ions in physiological medium in the body, the significance of production of hypochlorite and hypochlorite-induced damage to cellular components including DNA would be a predominant mechanism of radiation damage; 3) by associating with DNA base pairs as several flavonoids such as lutiolin, kempferol and quercetin; 4) by blocking abstraction of protons or addition of •OH on the purine and pyrimidine bases especially at C5, C6 and C8, and at the deoxyribose sites. These mechanisms have been proposed for protection from free radical-induced DNA damage; 5) lastly, by reduction of chloroamines formed, thus, regenerating internal and external amino groups in nucleic acids. Therefore, SDG as a scavenger of hypochlorite ions as well as being an antioxidant and free radical scavenger and protector of nucleobases from hypochlorite-induced chlorination can function as a DNA radioprotector and as a radiation mitigator.

Hypochlorite exists in solution as a mixture of hypochlorite anion (ClO$^-$), hypochlorous acid (HClO) and free chlorine (Cl$_2$) in pH-dependent amounts. At physiological pH, ClO$^-$ and HClO are the predominant molecules. Unlike strong, single-electron oxidants such as •OH, hypochlorite is a two-electron oxidant, less reactive and more selective than •OH. Hypochlorite can chlorinate electron-rich aromatic rings and NH-compounds. It oxidizes primary and secondary alcohols as well as benzyl methylene groups and tertiary methine groups, and phenols. The first step of the above reactions is chlorination followed by hydrolysis/HCl elimination. SDG contains all the above reaction sites except amino groups that make the SDG molecule a potent hypochlorite scavenger. In Scheme 1 (FIG. 20) we proposed a novel mechanism of DNA protection by SDG using either a 1-electron or a 2-electron reduction of a nucleobase.

In summary, we have demonstrated that SDG scavenges hypochlorite (ClO$^-$) ions and prevents radiation-induced hypochlorite and DNA damage. Since hypochlorite ions are known to modify DNA bases by chlorination/oxidation and then subsequently resulting in DNA damage, our findings show SDG may be useful as a radioprotector of normal tissue damage associated with radiotherapy for cancer treatment or accidental exposure to radiation.

Example 4

Flaxseed and its Lignans Protects Against the Effects of the Benzo-Alpha-Pyrene

Figure 21:
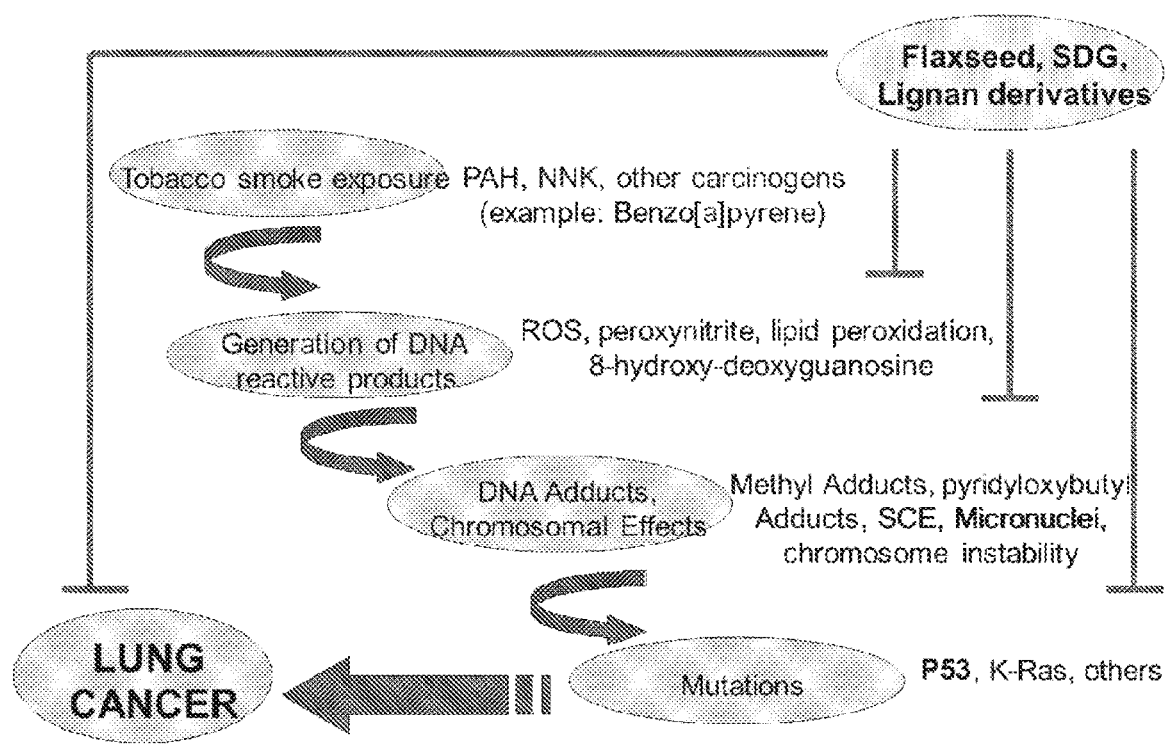
FIG. 21: Mechanism of chemoprevention by flaxseed and its lignans. SDG mitigates lung tumorigenesis by tobacco and other environmental carcinogens by inhibiting the multi-step carcinogenesis process. We provide evidence indicating that the lignan SDG has chemopreventive activity through modulation of the Nrf2-regulated Phase II detoxification pathway, and perhaps other mechanisms, in both animal models. We further provide data to support that the protective effects of SDG are mediated by the direct ROS scavenging and/or indirect antioxidant/anti-inflammatory properties, and decrease of carcinogen toxicity and DNA damage.

Flaxseed, SDG and lignan derivatives mitigate lung tumorigenesis by tobacco and other environmental carcinogens by inhibiting the multi-step carcinogenesis process (FIG. 21). In this example, experiments are provided indicating that the lignan SDG has chemopreventive activity through modulation of the Nrf2-regulated Phase II detoxification pathway, and perhaps other mechanisms, in animal models. The protective effects of SDG are mediated by the direct ROS scavenging and/or indirect antioxidant/anti-inflammatory properties, and decrease of carcinogen toxicity and DNA damage.

Figure 23:
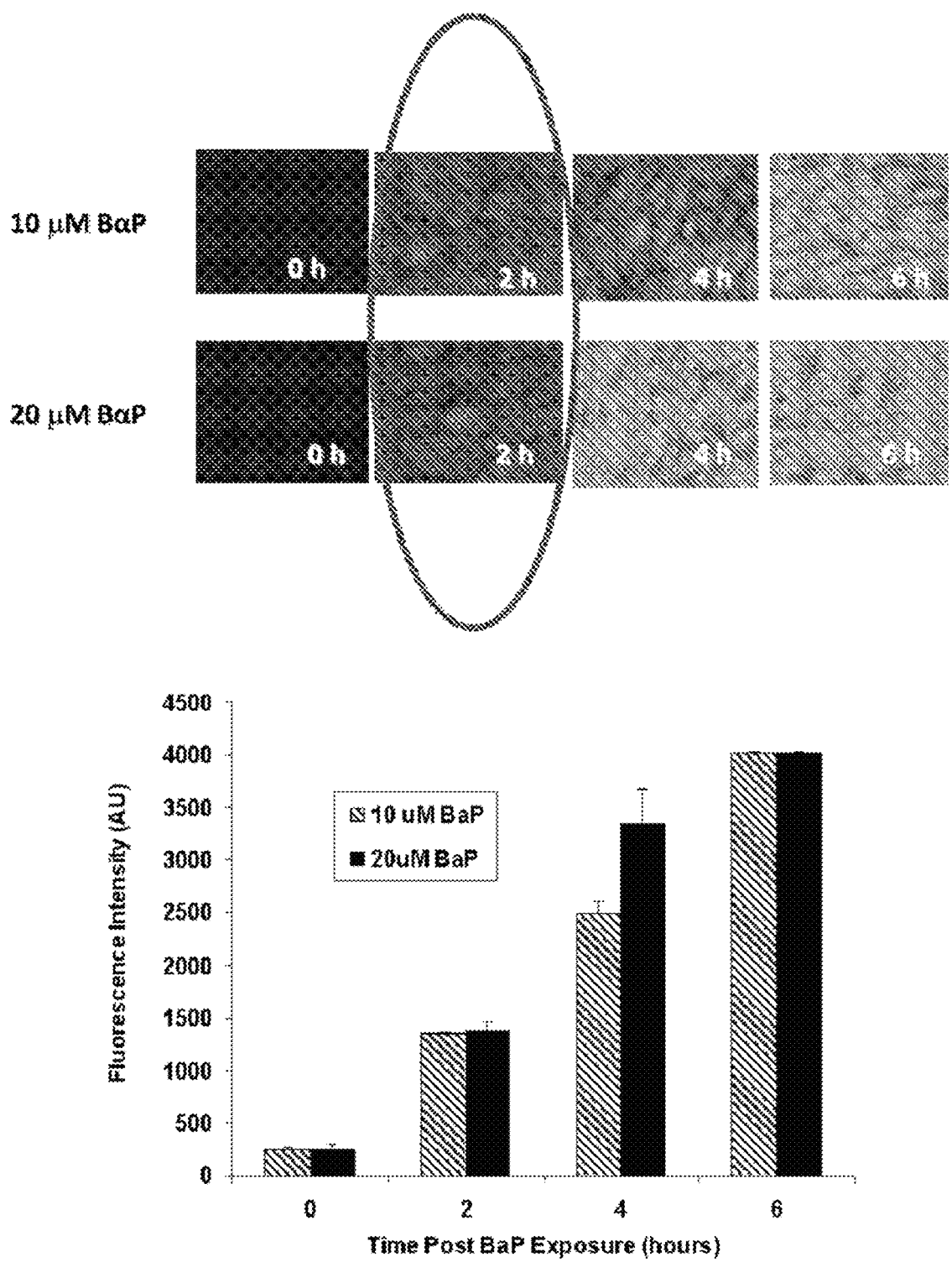
FIG. 23: The carcinogen benzo-alpha-pyrene induced ROS in cells. Exposure of murine epithelial cells to BaP induces damaging reactive oxygen species (ROS) as detected by a redox-sensitive fluorescence dye. As early as 2 hours, post exposure to the carcinogen, a robust increase of fluorescence intensity indicates ROS generation in cells.

Exposure of murine epithelial cells to the tobacco and environmental carcinogen benzo-alpha-pyrene (BaP) induces damaging reactive oxygen species (ROS) as detected by a redox-sensitive fluorescence dye (FIG. 23). As early as 2 hours, post exposure to the carcinogen, a robust increase of fluorescence intensity indicates ROS generation in cells.

Figure 22:
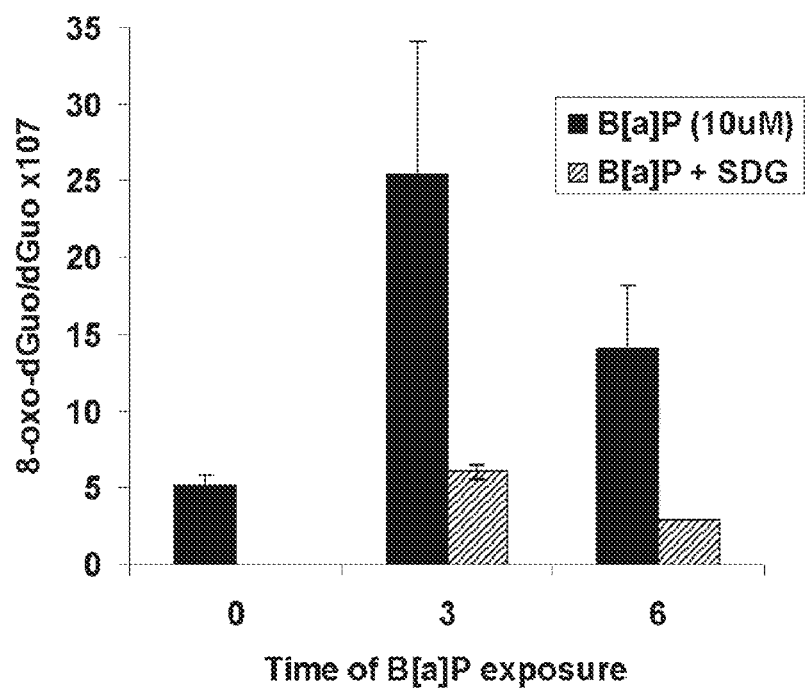
FIG. 22: SDG decreases oxidative DNA damage induced by benzo-alpha-pyrene in cells. SDG (10 µM) was added to human epithelial cells (A549) that were exposed to 25 µM of the tobacco and environmental carcinogen benzo-alpha-pyrene (BaP) and oxidative damage to DNA was detected using mass spectrometry as indicated by the presence of 8-oxo-7,8-dihydroguanine (8-oxo-dGuo). SDG decreased DNA damage at 3 and 6 hours post carcinogen exposure.
Figure 24:
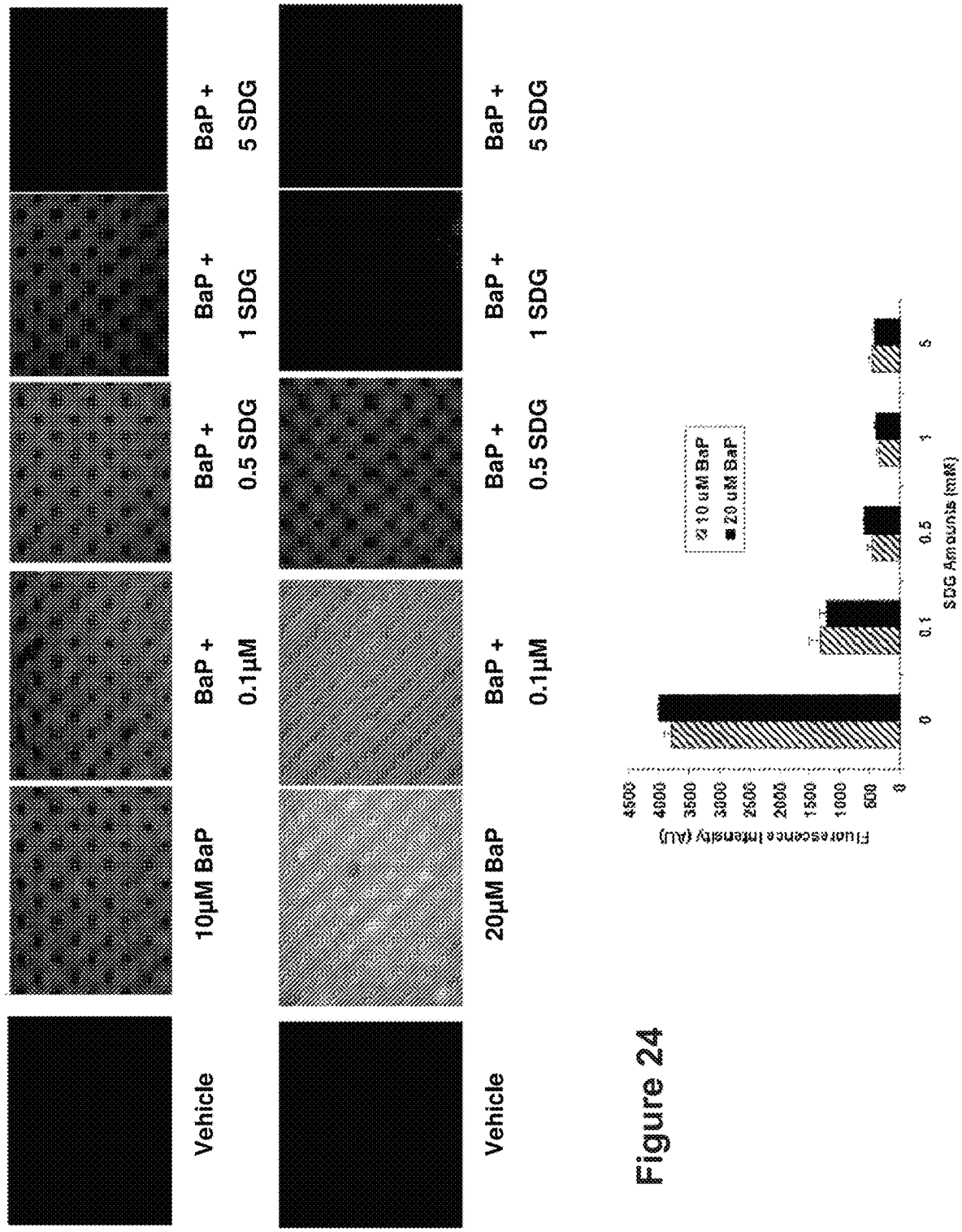
FIG. 24: SDG prevents ROS generation from carcinogen exposure. Mouse epithelial cells were exposed to 10 or 20 µM BaP and an increasing concentration of SDG (0, 0.1, 0.5, 1, 5 µM SDG) and ROS was detected 2 hours later (as determined appropriate in FIG. 23). SDG scavenged harmful ROS to negligible levels.

To demonstrate that SDG decreases oxidative DNA damage induced by carcinogens in cells, SDG (10 µM) was added to human epithelial cells (A549) that were exposed to 25 µM of BaP and oxidative damage to DNA was detected using mass spectrometry as indicated by the presence of 8-oxo-7,8-dihydroguanine (8-oxo-dGuo). SDG decreased DNA damage at 3 and 6 hours post carcinogen exposure (FIG. 22). Likewise, to demonstrate that SDG prevents ROS generation from carcinogen exposure, mouse epithelial cells were exposed to 10 or 20 µM BaP and an increasing concentration of SDG (0, 0.1, 0.5, 1, 5 µM SDG) and ROS was detected 2 hours later. SDG scavenged harmful ROS to negligible levels (FIG. 24).

Figure 25:
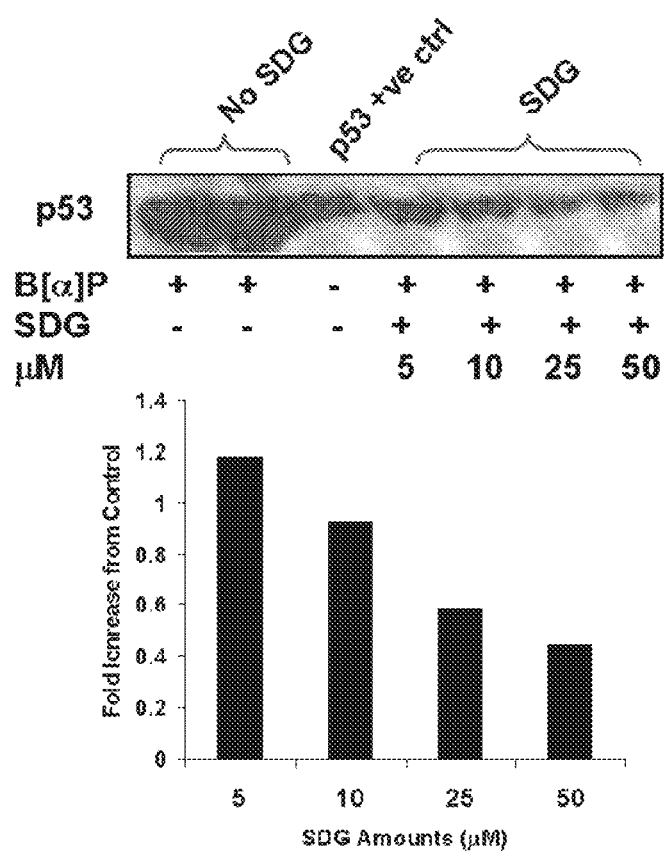
FIG. 25: SDG prevents genotoxic stress in human epithelial cells exposed to BaP. Exposure of cells to a potent carcinogen such as BaP, induces genotoxic stress as indicated by increased levels of p53 protein. This is mitigated dose-dependently by the presence of SDG, at 5, 10, 25 and 50 µM concentration.
Figure 26:
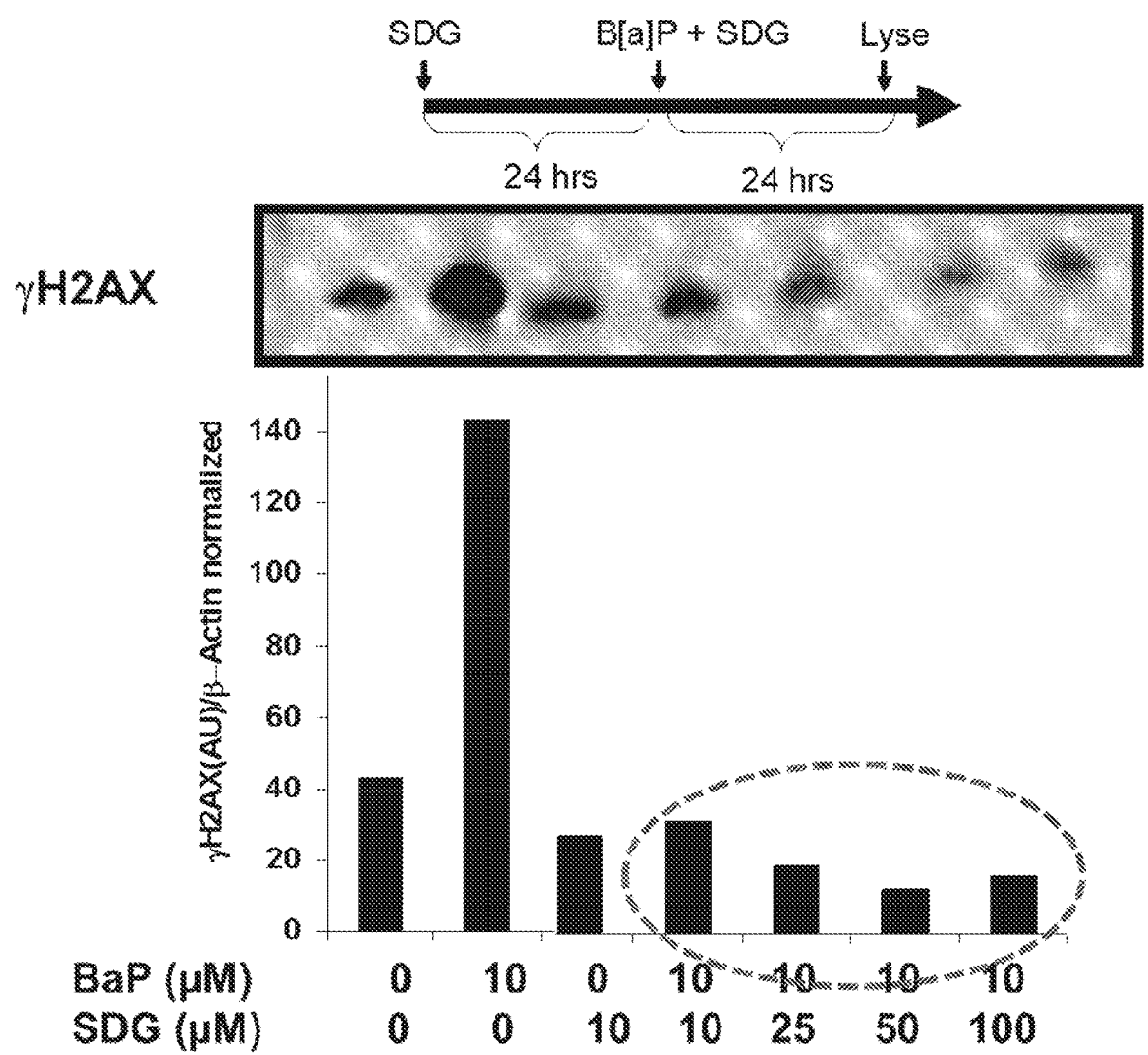
FIG. 26: SDG prevents oxidative DNA damages in human epithelial cells exposed to BaP. Exposure of cells to a potent carcinogen such as BaP, induces oxidative DNA damage as indicated by increased levels of gamma-H2AX, a marker for double-stranded DNA breaks. This is mitigated dose-dependently by the presence of SDG, at 5, 10, 25, 50 and 100 µM concentration.
Figure 27:
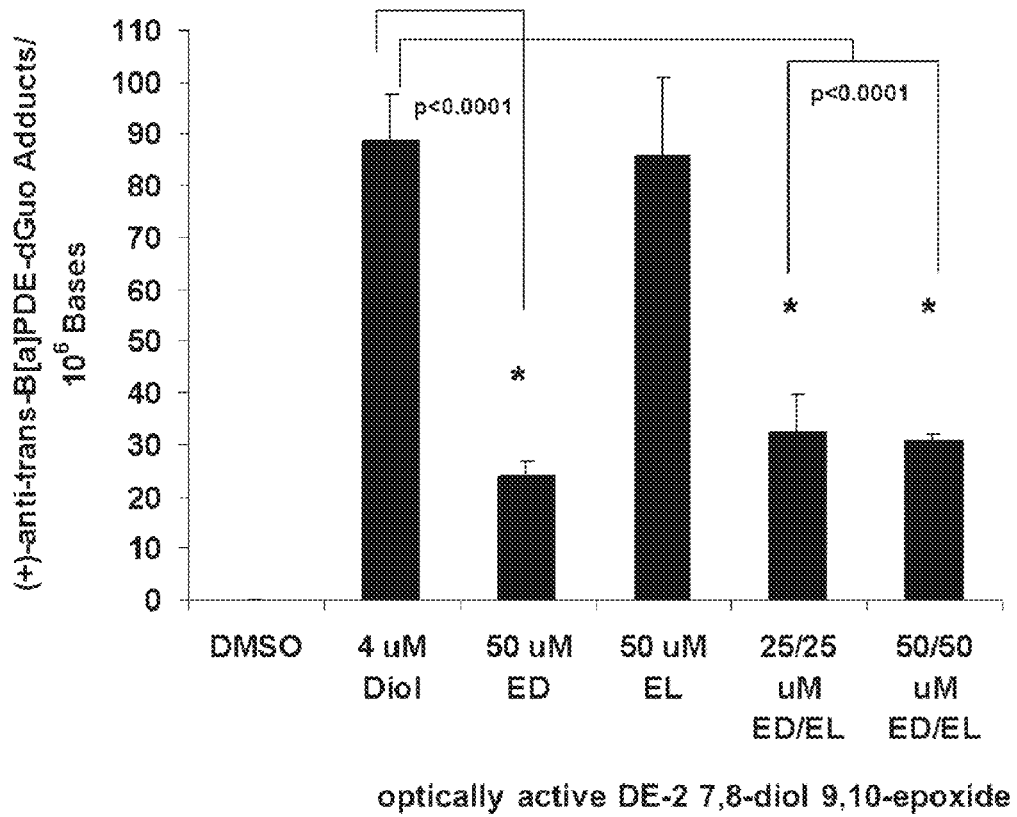
FIG. 27: SDG prevents DNA adduct formation in human epithelial cells exposed to BaP. Exposure of cells to a potent carcinogen such as BaP, induces the formation of DNA adducts. DNA adducts are pieces of DNA covalently linked to a carcinogen and is directly linked to the development of malignancy. The DNA adduct levels is decreased by the presence of SDG or its metabolites ED and EL given alone or in combination.

Similarly, SDG prevents genotoxic stress in human epithelial cells exposed to BaP. Exposure of cells to a potent carcinogen such as BaP, induces genotoxic stress as indicated by increased levels of p53 protein (FIG. 25). This is mitigated dose-dependently by the presence of SDG, at 5, 10, 25 and 50 μM concentration. SDG also prevents oxidative DNA damages in human epithelial cells exposed to BaP. Exposure of cells to a potent carcinogen such as BaP, induces oxidative DNA damage as indicated by increased levels of gamma-H2AX, a marker for double-stranded DNA breaks (FIG. 26). This is mitigated dose-dependently by the presence of SDG, at 5, 10, 25, 50 and 100 μM concentration. Furthermore, SDG prevents DNA adduct formation in human epithelial cells exposed to BaP. Exposure of cells to a potent carcinogen such as BaP, induces the formation of DNA adducts (FIG. 27). DNA adducts are pieces of DNA covalently linked to a carcinogen and is directly linked to the development of malignancy. The DNA adduct levels is decreased by the presence of SDG or its metabolites ED and EL given alone or in combination.

Figure 28:
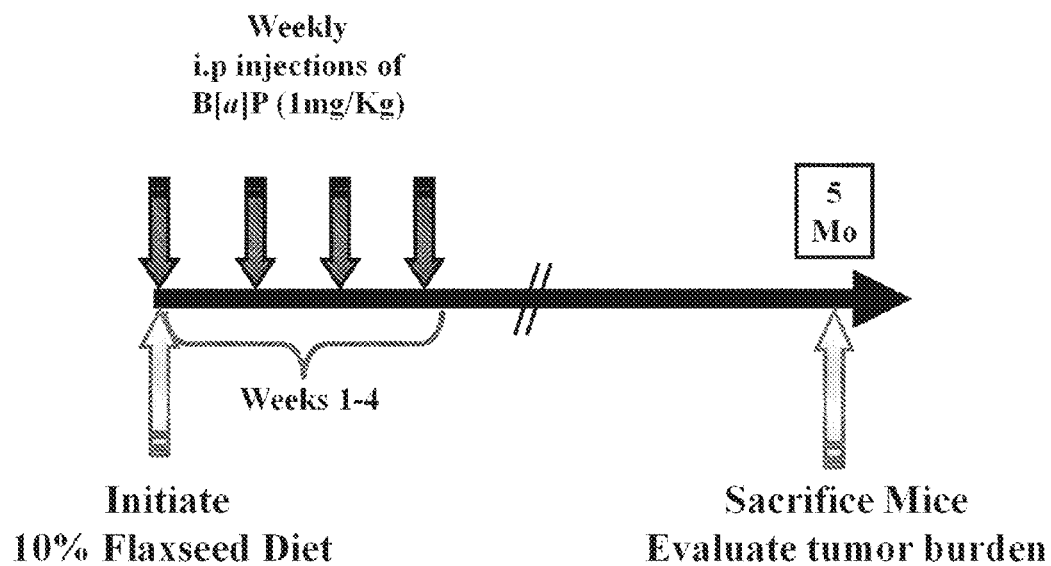
FIG. 28: Mouse model of chemical carcinogen-induced lung tumors. Mice (A/J strain) are given 4 injections intraperitoneally of the tobacco and environmental carcinogen BaP (once weekly) at 1 mg/Kg dose. Mice are initiated on flaxseed or lignan diet at the time of exposure. Mice are evaluated at various times post exposure to determine tumor burden, mouse weight, and overall health profile.

Flaxseed and its lignans provides protection in a mouse model of chemical carcinogen-induced lung tumors. Mice (A/J strain) are given 4 injections intraperitoneally of the tobacco and environmental carcinogen BaP (once weekly) at 1 mg/Kg dose (FIG. 28). Mice are initiated on flaxseed or lignan diet at the time of exposure. Mice are evaluated at various times post exposure to determine tumor burden, mouse weight, and overall health profile.

Flaxseed Decreases Tumor Burden in Mice:

FIG. 29 presents representative clinical images of murine lungs several months post BaP exposure and dietary flaxseed administration. FIG. 30 presents representative H&E-strained lung sections of murine lungs several months post BaP exposure and dietary flaxseed administration. Nodules indicated by the arrows from mice fed control diet (top panels) or flaxseed (lower panels) appear smaller in the flaxseed-fed mice. Each panel represents a different animal.

Figure 31A:
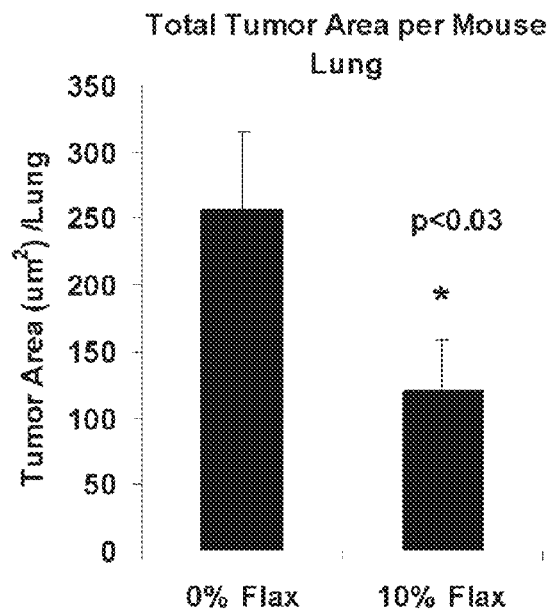
FIGS. 31A-31B: Flaxseed decreases tumor burden in mice: Quantitative assessment of tumor burden. Histological murine lung sections were evaluated morphologically using image analysis software for overall tumor area (FIG. 31A) and nodule size (FIG. 31B). There was a significant decrease in the area of the lung occupied by tumor in the mice fed a flaxseed diet ($p<0.03$). Similarly, there was a trend for smaller tumor nodule size.
Figure 31B:
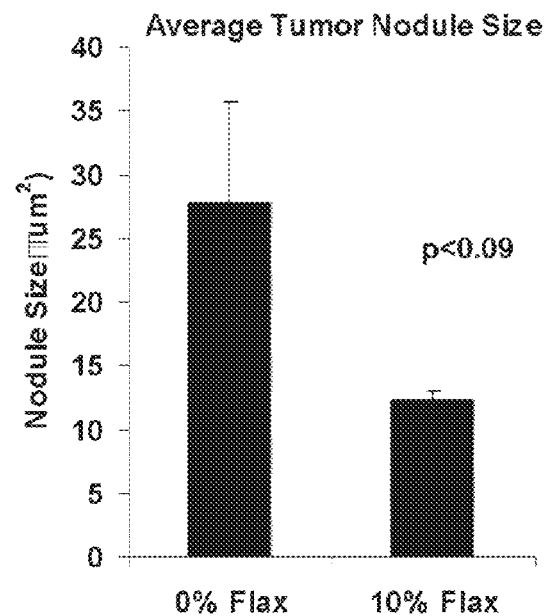
Figure 32A:
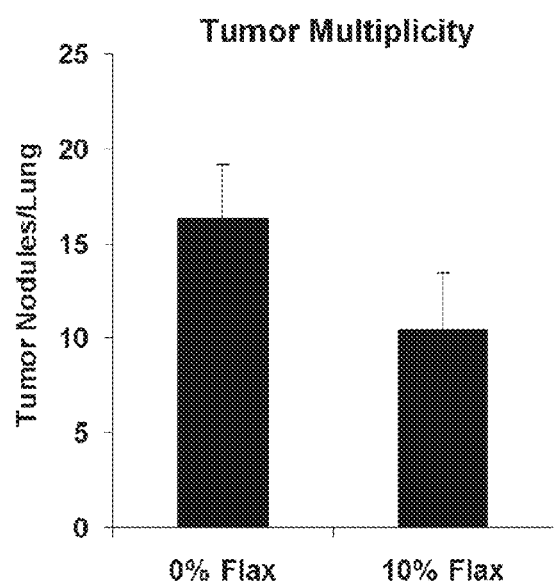
FIGS. 32A-32B: Flaxseed decreases tumor burden in mice: Quantitative assessment of tumor burden. Histological murine lung sections were evaluated morphologically using Image analysis software for overall number of tumor nodules per lung (FIG. 32A) and % tumor invading the lung (FIG. 32B). There was a trend for less tumor nodules per lung (FIG. 32A) and less tumor invading with flaxseed supplementation (FIG. 32B)
Figure 32B:
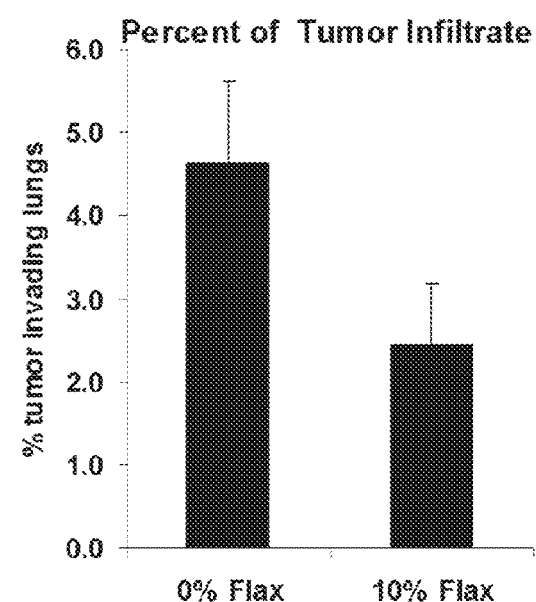

Histological murine lung sections were evaluated morphologically using image analysis software for overall tumor area and nodule size (FIGS. 31A and 31B). There was a significant decrease in the area of the lung occupied by tumor in the mice fed a flaxseed diet ($p<0.03$). Similarly, there was a trend for smaller tumor nodule size. Histological murine lung sections were also evaluated morphologically for overall number of tumor nodules per lung (FIG. 32A) and % tumor invading the lung (FIG. 32B). There was a trend for less tumor nodules per lung (A) and less tumor invading with flaxseed supplementation (B).

Figure 33:
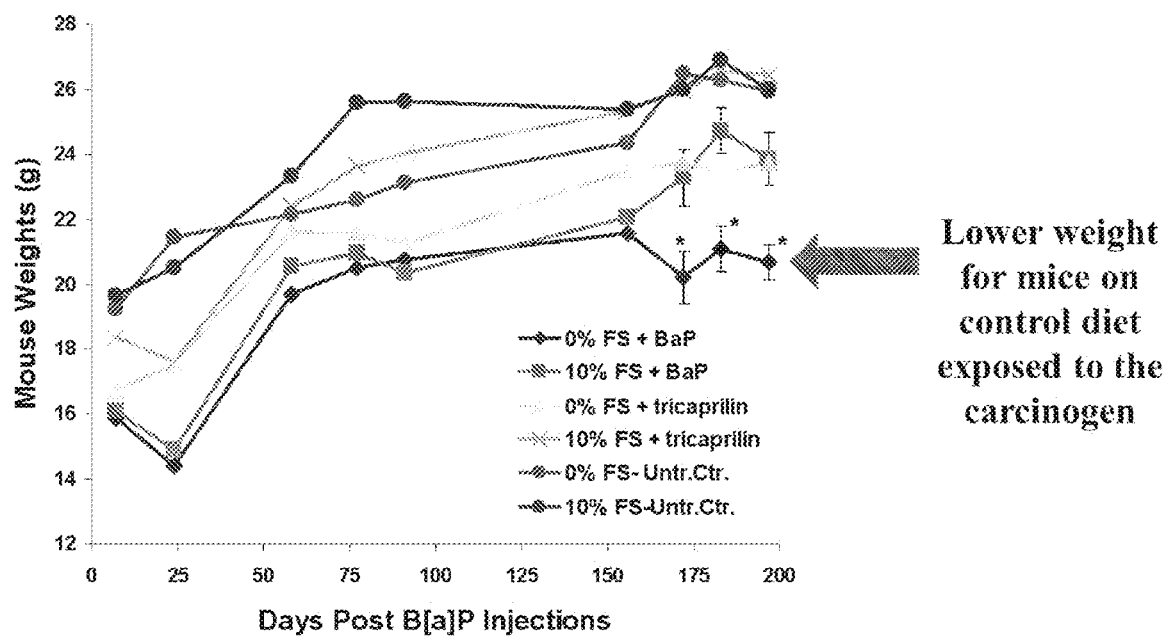
FIG. 33: Flaxseed supplementation prevents wasting effects from lung cancer induced by BaP Animal weight was measured longitudinally for 200 days post BaP exposure. Mice fed a flaxseed diet, exposed to BaP showed higher weight than those exposed to BaP on control diet.

Finally, flaxseed supplementation was shown to prevent wasting effects from lung cancer induced by BaP. Animal weight was measured longitudinally for 200 days post BaP exposure. Mice fed a flaxseed diet, exposed to BaP showed higher weight than those exposed to BaP on control diet (FIG. 33).

Example 5

Flaxseed and its Lignans Protect Cells and Tissues from Asbestos-Induced Damage

Introduction

Malignant mesothelioma (MM) is a devastating, painful and lethal type of cancer with no realistic chance for therapy and treatment. Development of MM has been linked directly to exposure to asbestos fibers. Recent studies have indicated that the pathogenesis of asbestos-induced cancers is due to chronic inflammation and oxidative tissue damage caused by persistent asbestos fibers. Whole grain Flaxseed (FS) has known antioxidant, anti-inflammatory and cancer chemo-preventive properties. In this Example, the ability of FS and its lignan component (FLC) enriched in the lignan secoisolariciresinol diglucoside (SDG) given in diets to prevent acute asbestos-induced inflammation and inflammatory cytokine release was tested in $Nf2^{+/mut}$;$Cdkn2a^{+/mut}$ mice.

Materials and Methods

Mouse Diets and Asbestos Exposure

Figure 34:
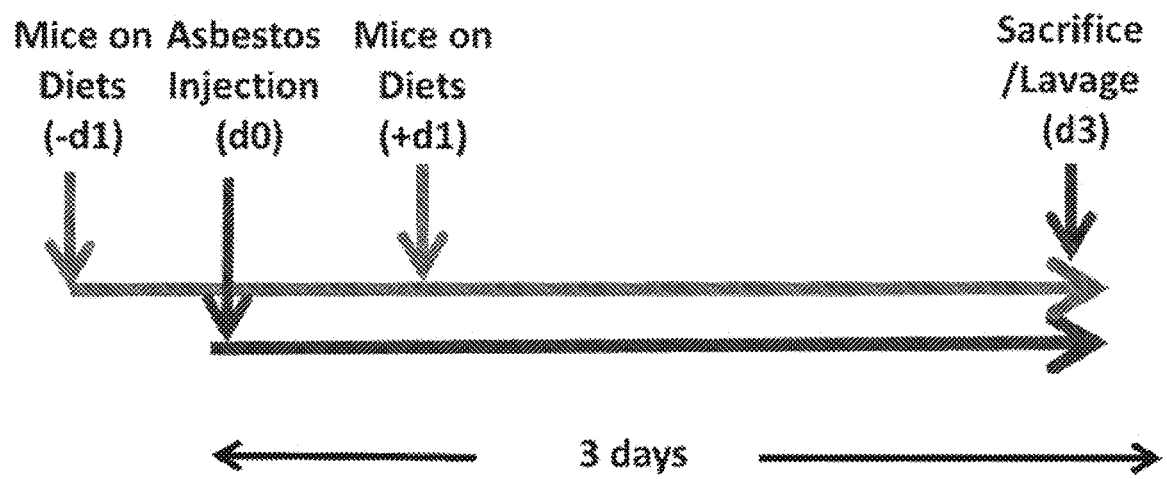
FIG. 34: Experimental Scheme for Example 5.
Figure 37A:
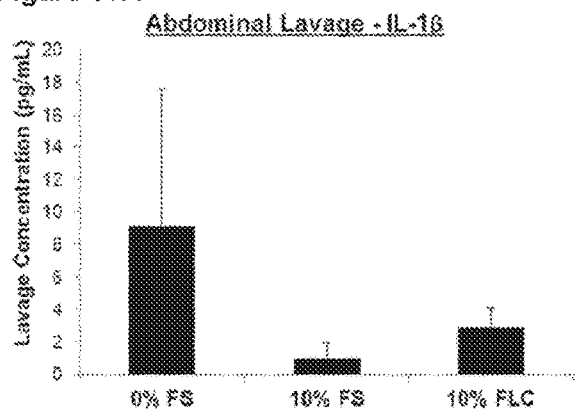
FIGS. 37A-37D: Mice were initiated on FS and FLC diets and exposed to asbestos 24 hours later. Cytokines levels (TNFα and IL-1β) in plasma (FIGS. 37B, 37D) and in abdomen, (FIG. 37A, 37C) were determined using ELISA 3 days post exposure according to the experimental scheme in FIG. 34. Both diets indicated a trend towards preventing secretion of pro-inflammatory cytokines in the abdomen and the systemic circulation induced by asbestos exposure.
Figure 37B:
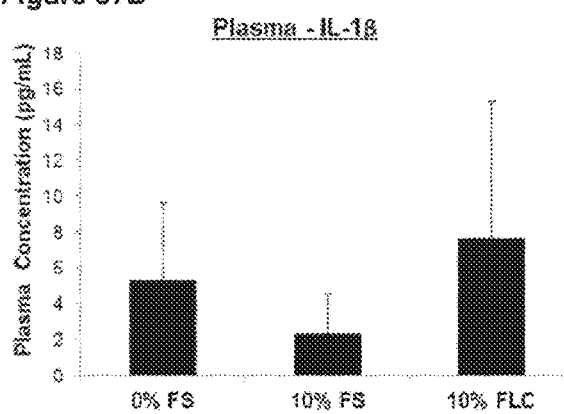
Figure 37C:
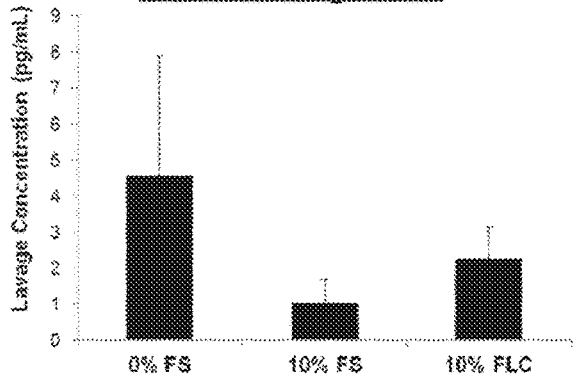
Figure 37D:
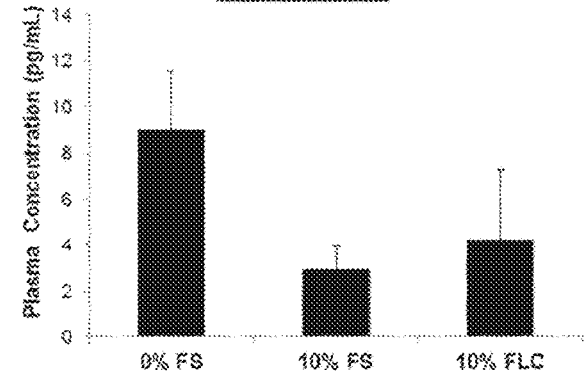
Figure 38A:
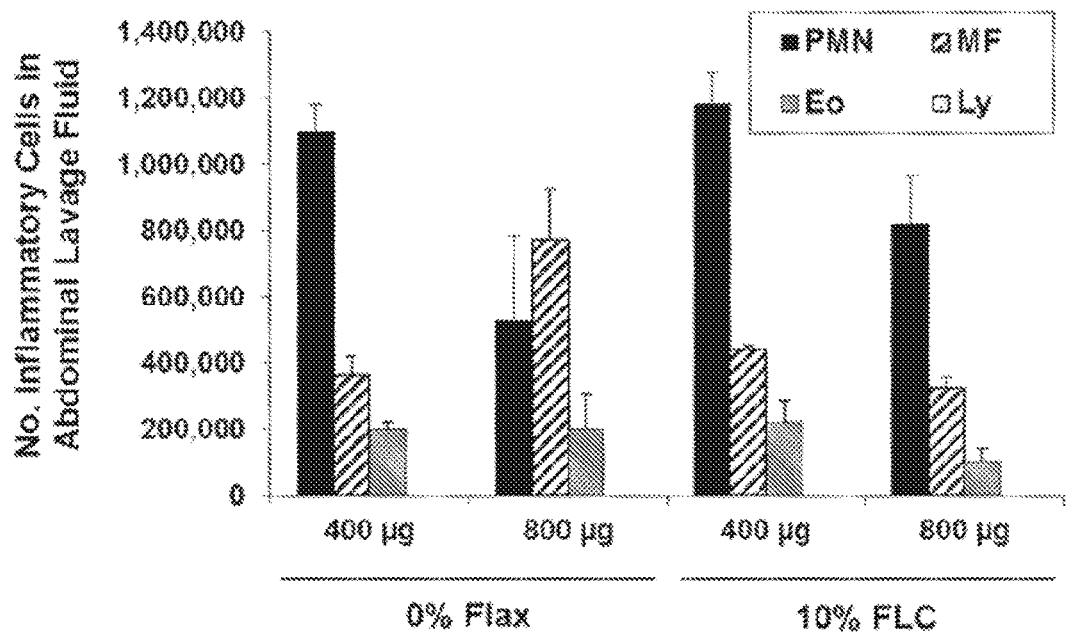
FIGS. 38A-38C: Inflammatory cells also trended lower with the diet (FIG. 38A) while TNFα (FIG. 38B) and IL-1β (FIG. 32C) cytokine levels induced by 400 and 800 mg crocidolite asbestos were significantly blunted by FLC added in the diet 1 day post asbestos exposure (*$p<0.05$). *p designates significance as compared to control diet exposed to asbestos.
Figure 38B:
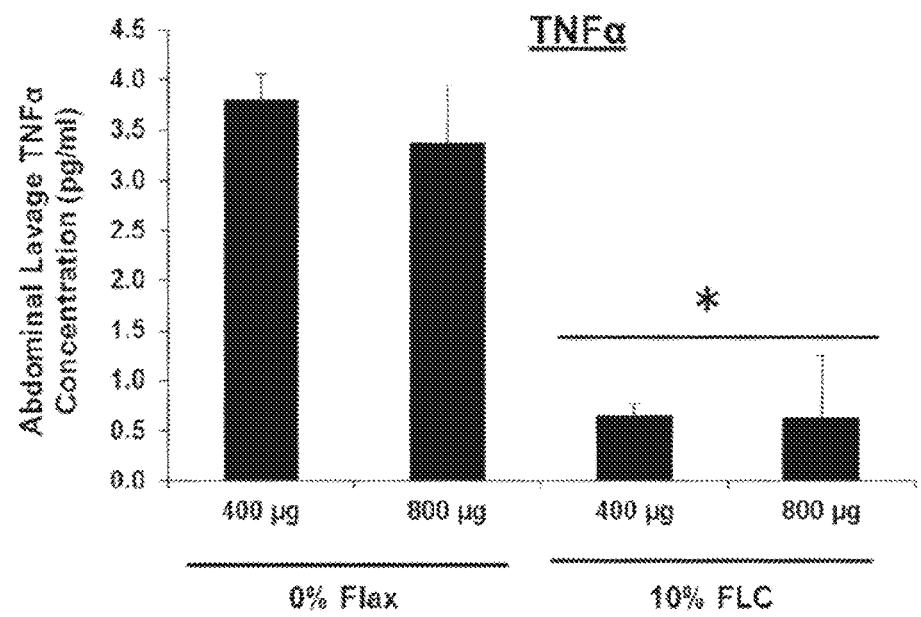
Figure 38C:
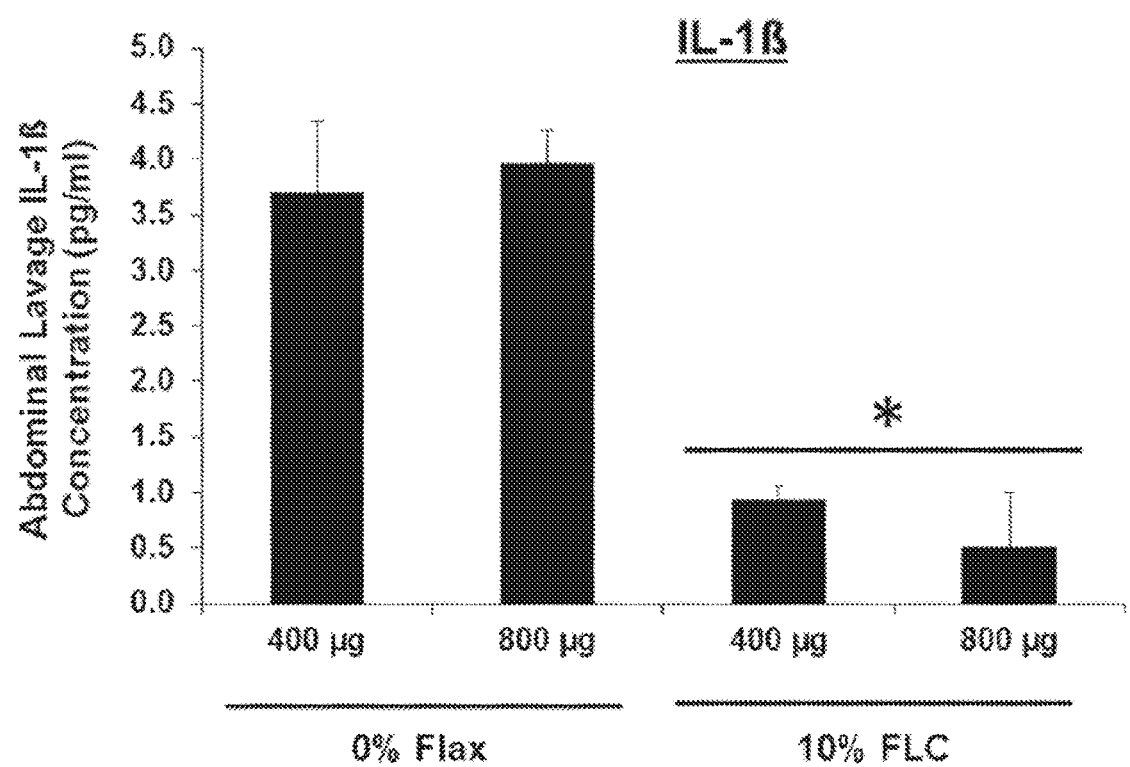

FS and its lignan component, (FLC) enriched in the lignan secoisolariciresinol diglucoside (SDG) was given in rodent chow. Mice ($Nf2^{+/mut}$;$Cdkn2a^{+/mut}$) were, placed a day later (+1) or prior (−1) to a single ip bolus of 400 mg of crocidolite asbestos on 10% FS or 10% FLC supplemented diets and evaluated 3 days later for abdominal inflammation and proinflammatory cytokine release (see FIG. 34). The NF2 mouse strain was selected as it develops an accelerated form of MM when exposed to asbestos.

Tissue Harvest and Analysis

Using liquid chromatography, tandem mass spectrometry (LC/MS/MS), systemic levels (i.e., plasma) of flaxseed lignan metabolites such as the mammalian lignans Enterolactone (EL) and Enterodiol (ED) were evaluated to ensure that FS was effectively metabolized by the gut flora of this mouse strain and that levels were comparable to those in other mouse models.

Abdominal lavage was performed using PBS and levels of macrophages (MF) and neutrophils (PMN) determined using cytospin analysis.

Discussion

Using liquid chromatography, tandem mass spectrometry (LC/MS/MS), systemic levels (i.e., plasma) of flaxseed lignan metabolites such as the mammalian lignans Enterolactone (EL) and Enterodiol (ED) were evaluated to ensure that FS was effectively metabolized by the gut flora of this mouse strain and that levels were comparable to those in other mouse models (FIGS. 37A-37D). Abdominal lavage levels of macrophages (MF) and neutrophils (PMN) indicated that both FS and FLC blunted acute abdominal inflammation induced by asbestos (FIGS. 36 and 38A-38C). In addition, the levels of pro-inflammatory cytokines TNF-α and IL-1β were also decreased by the dietary agents (FIGS. 37A-37D and 38A-38C).

Conclusions:

These findings indicate that the chemopreventive properties of Flaxseed and its lignan component extend to protection from asbestos-induced tissue and cellular damage. Flaxseed can thus, be used as a dietary agent in the chemoprevention of malignant mesothelioma.

Example 6

Optimizing Dose and Kinetics of SDG Administration In Vivo

In this Example, data is presented on pharmacokinetics, bioavailability, and dose response in mice given SDG via oral gavage in a water-soluble form.

Figure 39:
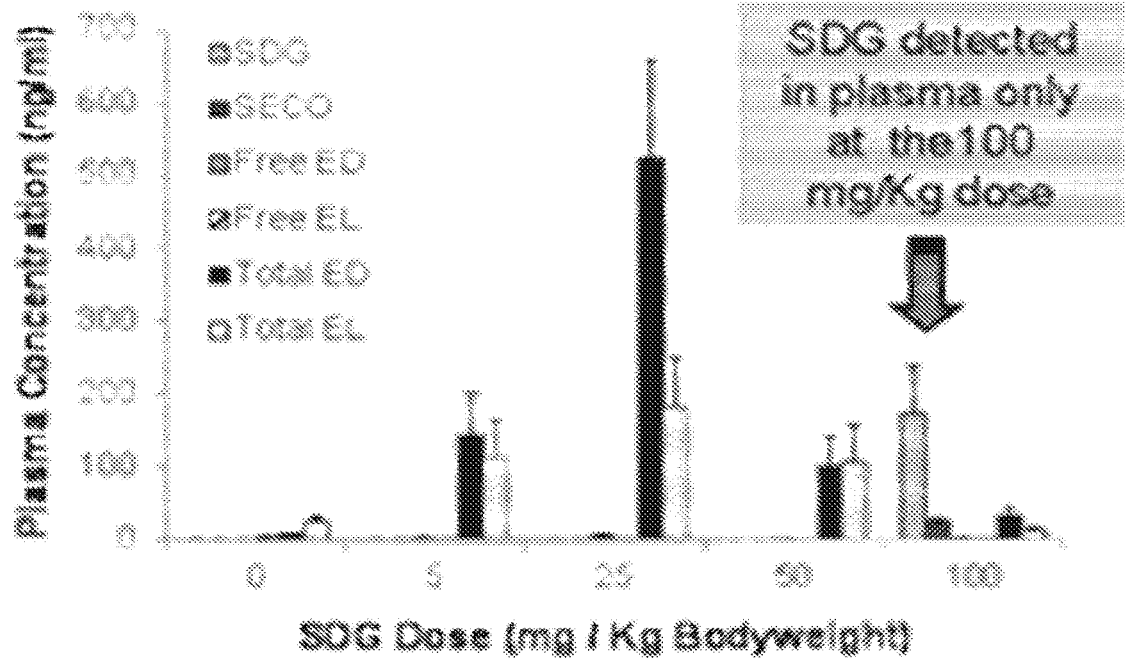
FIG. 39: Plasma concentration of SDG and metabolites following oral gavage of variable SDG concentrations in mice.
Figure 40:
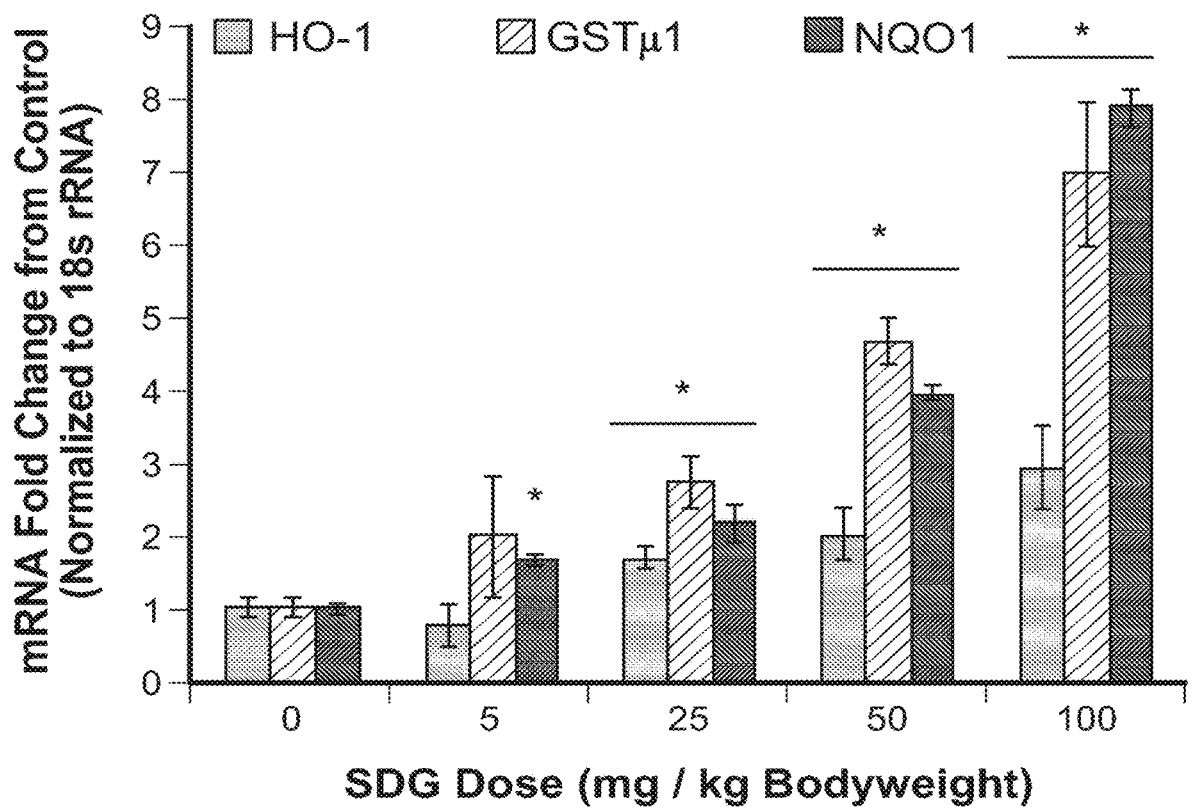
FIG. 40: Antioxidant enzyme gene expression levels in lung following oral gavage of variable doses of SDG in mice.

Dosing Study:

SDG doses of 5, 25, 50 and 100 mg/Kg body weight were administered orally to mice (n=5 per dose) and 4 hours later tissues were collected for analysis. Plasma concentrations of SDG and its bioactive metabolites ED, EL and SECO were analyzed by liquid chromatography and mass spectrometry and are expressed in ng/mL (FIG. 39) while gene expression levels of Nrf2-regulated antioxidant enzymes (AOE), an intracellular target of SDG and its metabolites, were determined in lung tissues from the same animals using qRT-PCR (FIG. 40). Gene expression levels of HO1, NQO1 and GST, increased 2-3 fold with as little as 5 mg SDG/Kg and reached an average of 6-fold increase over baseline with 100 mg/Kg SDG. Gene levels are supported by lower but yet significant increase in protein levels in lung tissues.

Figure 41A:
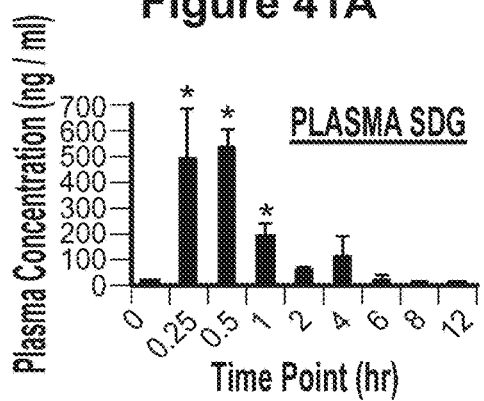
FIGS. 41A-41C: Kinetics of SDG levels in plasma (FIG. 41A) and lung tissues (FIG. 41B) following oral gavage of 100 mg/Kg SDG in mice and corresponding levels of AOE gene expression (FIG. 41C).
Figure 41B:
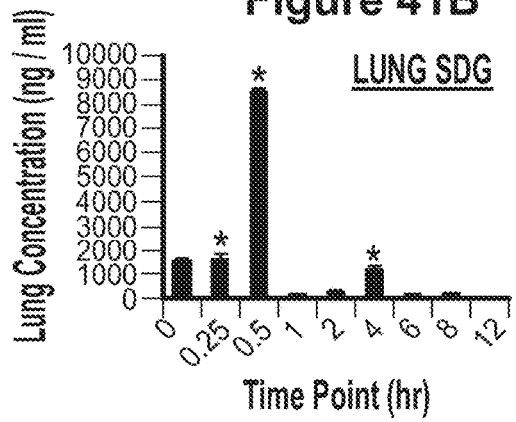
Figure 41C:
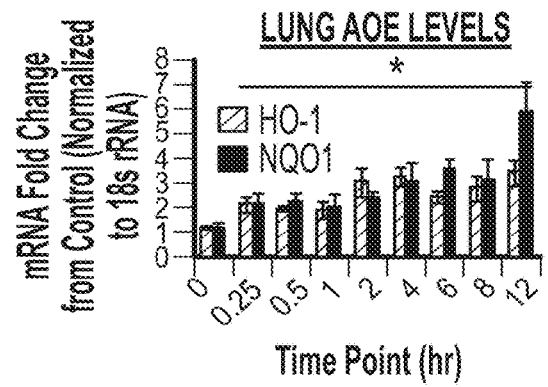

Pharmacokinetic Study:

After selecting the 100 mg/kg dose as a dose that induces significant AOE expression while allowing for SDG to be detected in circulation, a pharmacokinetic study was performed to determine bioavailability and biological effects in target tissues (i.e., lung). Blood samples as well as tissues (lung, brain, liver, kidneys, spleen) were collected at 15 min, 30 min, and 1, 2, 4, 6, 8, 12 hours. SDG levels were determined as above in plasma and lung (FIGS. 41A-C). A single dose of 100 mg SDG/Kg was well absorbed and intact SDG was detectable in the circulation up to 6 hours post administration (FIG. 41A) and in flushed, blood-free lung tissues for 4 hours (FIG. 41B). Plasma and lung tissue concentrations of SDG reached levels of 0.8 and 12.6 µM at 30 minutes post-administration, respectively. Remarkably, robust induction of representative AOE gene expression levels (HO-1, NQO1, GST) were significantly elevated (p<0.05) over baseline (FIG. 41C). The observed gene expression increase correlated with an increase in protein levels determined by western blotting (not shown). Importantly, SDG at the same dose given twice daily for 7 days showed neither intolerance nor toxicity. These data indicate that significant bioavailability and efficiency can be obtained by this soluble SDG form. The use of SDG in human therapy is thus greatly facilitated and the toxicity risk is unlikely. Therefore a dose of 50-100 mg/Kg (1 or 2 mg SDG per day) is sufficient to induce the anticipated protective effects in target tissues and can be used for further study.

Example 7

Effects of SDG in BaP-Induced Lung Tumorigenesis in Nrf2-Deficient Mice on the Initiation or Promotion Phases of Carcinogenesis Data from lung injury models show that FS and FS-derived SDG in diets can upregulate Nrf2 and Nrf2-actived genes and proteins in lungs. In this Example, using Nrf2 knockout mice, the hypothesis that activation of this pathway is an important mechanism of the chemopreventive effects of SDG is tested and it is determined if SDG has activity in both the initiation and promotion phases of carcinogenesis.

Effects of SDG in Nrf2-Deficient Mice.

Figure 42A:
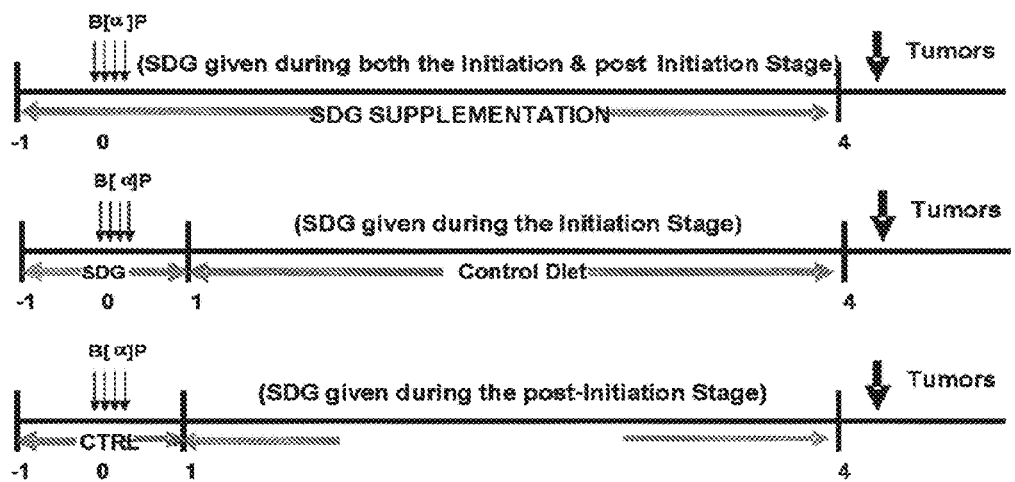

In these experiments, the effects of synthetic SDG given orally in the BaP-induced lung cancer model in wild-type A/J mice are compared to Nrf2-deficient mice backcrossed on an A/J background (colony currently maintained at our animal facility). Briefly, one group of wild-type (WT) mice and one group of knockout (KO) mice are fed a control diet. One group of WT mice and one group of KO mice are given SDG via their drinking water to achieve 50 and 100 mg/Kg daily SDG consumption (to test dose response relationship in inhibiting the development of lung cancer) as shown in FIG. 42A. SDG dosing studies and kinetics determined that SDG should be given for at least a few days, as this was determined to be the minimum time required for the diets to reach steady state in tissues, followed by 4 weekly injections of 1 mg/mouse Benzo[a]pyrene (BaP) given i.p. Both 50 and 100 mg/Kg SDG given orally (oral gavage or in drinking water) can induce Phase enzyme expression in lungs (see FIGS. 41A-41C). Mice are sacrificed at 4, 6 and 9 months (see FIG. 42B) and lung tissues are harvested for a) histological evaluation of tumor burden and quantification by image analysis, b) western blot detection of Nrf2-regulated AOE expression and oxidative stress, c) 8-oxo-7,8-dihydro-2'-deoxyguanosine (8-oxodGuo) levels in murine tissues and urine, and d) DNA adduct formation. A subset of mice are evaluated for lung inflammation using a) Bronchoalveolar lavage, and b) FACS analysis of inflammatory cells such as neutrophils, activated macrophages and T cells using antibodies to CD11b/Ly6G, CD11b/F4/80, and anti-CD3, respectively.

Statistics: The minimum number of mice required per group to achieve statistical significance and suggested 20 mice/group.

Analysis:

As above (FIGS. 29 and 31A-31B a reduction in the number and size of tumors is expected in the WT mice getting both 50 and 100 mg/Kg SDG, however results are more profound with the 100 mg/Kg dose (less tumor). A higher number of tumors is expected in the Nrf2 KO mice getting control (no drug) due to loss of ability to detoxify the BaP when compared to WT mice on control diet. However, no reduction in tumors is expected in the Nfr2 KO mice receiving the SDG (compared to the KO mice getting no drug), since the primary effect of SDG is mediated via Nrf2 activation. Whatever reductions are seen in the tumor burden in the Nrf2/SDG mice, is attributable to other mechanisms that are also contributing, such as the direct free radical scavenging effects of SDG, which should be detectable by measuring markers of oxidative stress.

Role of SDG and Nrf2 Activation in the Initiation and/or Promotion Phases of Carcinogenesis.

The data above is expected to provide clear mechanistic data regarding SDG administration during both the initiation and promotion phases of BaP. It is also of interest to determine the efficacy of SDG supplementation during just the initiation phase (FIG. 42A, Plan B) or during just the promotion phases (FIG. 42A, Plan C). Accordingly, the experiments outlined in this schema are performed in wild-type A/J mice using these different feeding schedules.

Analysis:

Decreases in tumor numbers and size are expected when giving SDG during either promotion or initiation. The studies are repeated in Nrf2 KO mice, as above, to define the contribution of Phase II enzyme upregulation to this activity. It has recently been reported that Nrf2 has two roles during carcinogenesis, one of which is preventive during tumor initiation and the second that promotes malignant progression. These findings suggest use of Nrf2 to prevent malignant progression in lung cancer, whereas Nrf2 activators are more suited for lung cancer prevention. SDG is expected to be effective as a chemopreventive agent. Notwithstanding the role of Nrf2 in the anti-carcinogenic effects of SDG, it is possible that other mechanisms are also involved or even more important such as the modulation of miRNA in systemic fluids (blood) or lung tissues.

The Effects of Administration of an SDG Supplement to Smokers on Systemic and Lung-Specific Biomarkers of Oxidant Stress.

A clinical study of oral administration of SDG with genetic and biochemical endpoints being genetic and biochemical is designed.

Population Selected:

The first group will consist of normal, healthy volunteers who have never smoked. This group allows assessment of true baseline levels (likely low) of genes of interest and oxidative biomarkers, in order to evaluate the changes induced by SDG supplementation in a "non-stimulated"

environment. The second group of subjects will consist of current, active smokers. This group is selected because: i) they are at high risk for active cancer initiation and are potential subjects in a chemoprevention trial and ii) it has previously been shown that smoking induces its own genomic changes in the respiratory epithelium, as well as active oxidative stress. This group allows profiling of genomic and oxidative stress markers in smokers and to determine what genomic changes are induced by SDG in an already "activated" environment. This group also allows a determination of the reduction of elevated markers of oxidative stress by SDG in this high risk population. A crossover design is selected where each patient will also ingest both a placebo control and an SDG supplement both given in gelatin capsules (See FIG. 43).

Dosage:

A commercial preparation (BREVAIL™) was chosen to avoid the marked variability in SDG content and bioavailability observed with different batches of raw or ground flaxseed. Alternatively, synthetic SDG such as that described by Mishra et al., *Bioorganic & Medicinal Chemistry Letters* 2013, (19):5325 will be used. Pharmacologic studies had shown that daily dosing with this formulation, which contains 50 mg of SDG, produced ENL levels (median, 63 nmol/L) similar to those found in the highest quintiles associated with reduction in cancer incidence in case-control studies.

Clinical Study:

The study will be a single center, randomized, double-blind, two period cross-over trial. There will be two 3 week treatment periods interspersed with a one-month washout period (FIG. 43). The rationale for the cross-over design is that comparison of treatments within subjects removes any "subject effect" from the comparison and enhances the efficiency and power of the study. Twenty (20) healthy volunteers (10 smokers and 10 lifelong nonsmokers) are randomized to ingest, in order, EITHER 50 mg SDG (either one capsule BREVAIL™ or synthetic SDG) daily for 3 weeks followed by a 1-month washout period and then placebo (same capsule without SDG, provided by the same provider (Lignan Research, San Diego, Calif.) for an additional 3 weeks, OR placebo for 3 weeks, a one month washout, and then 50 mg SDG for 3 weeks. Oral epithelium (obtained by a mouth swab), exhaled breath condensate, urine and blood are obtained at baseline, and weeks 2, 3, 7, 9, and 10. Active smoking status will be confirmed by urinary cotinine assays. The study will be approved by the Penn Institutional Review Board, and all participants will provide written informed consent. A detailed questionnaire will be administered at baseline including a comprehensive smoking history, and environmental tobacco exposure (ETS). Participants will be seen weekly for evaluation of side-effects, adherence to test agent ingestion, collection of data on interim tobacco and medication use and sample collection.

Statistical Rationale/Power Analysis:

The major comparisons of interest are the change in urinary oxidative stress, as measured by urinary 8-oxo-7,8-dihydro-2'-deoxyguanosine (8-oxo-dGuo), changes in exhaled breath condensate isoprostanes (exploratory), and changes in gene expression levels in buccal epithelium in study subjects following SDG treatment. 20 patients is expected to provide reasonable power for this exploratory study. Because of the nature of this study, corrections are not applied for multiple comparisons. The study is designed to get an assessment of the effect of the SDG supplement. Note also, that there is limited power to test for carryover effects, but the 4-week washout period should obviate these concerns.

Evaluation of Gene Expression Changes in Buccal Swab Epithelial Cells Post Oral SDG Ingestion In these experiments, buccal mucosal epithelial cells are used as surrogate tissue to bronchial epithelial tissue. Such cells are easier to obtain (i.e. by using a simple swabbing of the cheek) than bronchial epithelial cells which require an invasive bronchoscopy. The validity of this approach in humans is supported by evidence that buccal epithelium can serve as surrogate tissue for airway bronchial tissues in gene array studies.

This approach was further validated using ingested FS in mice. After mice were fed a control or 10% FS diet for three weeks, a range of tissues was harvested and analyzed for expression of two representative Nrf-2 inducible proteins (HO-1 and NQO1) by immunoblot. Marked increases in these markers in the lung and liver were seen (data not shown). Importantly, clearly detectable increases in nasal epithelium of both proteins were seen (FIG. 44), thus validating that nasopharyngeal tissue can also be used as a surrogate for lung. There is also some feasibility data to support this approach in humans Wholegrain FS (40 g daily) was given to 2 normal volunteers for a week. Buccal swabs were taken, RNA successfully extracted, and cDNA was made. The relative expression levels of the Nrf2-dependent gene HO-1 was measured. As shown in FIG. 45, HO-1 mRNA expression was increased by 34% in one subject and 63% in the second (p<0.05). These data show this approach is feasible and that FS and SDG boost Nrf2-dependent genes in normal healthy volunteers.

In the trial, buccal swabs are taken at baseline and after 2 & 4 weeks of the fiber control and FS diet, in both the control and smoking subjects. mRNA and cDNA are generated as above and subjected to RT-PCR to evaluate the relative expression levels of representative antioxidant and Phase II drug metabolizing enzymes, including NQO-1, HO-1, and glutathione-S-transferases (GST). In addition to being "classic" representatives of Nrf2-inducible enzymes, the selected enzymes may also play important mechanistic roles. NQO1 plays a dual role in the detoxification and activation of pro-carcinogens that are present in tobacco smoke. Variant genotypes of NQO1 were significantly associated with decreased risk of lung cancer in Japanese subjects. HO-1 has also been implicated as a cytoprotective agent against oxidants and aromatic hydrocarbons in cigarette smoke in genetic studies. Therefore, HO-1 also represents a significant biomarker for monitoring the effects of flaxseed. Numerous studies have shown relationships between GST polymorphisms, smoking, and lung cancer. Importantly, benzo[a]pyrene-derived DNA-adducts in lung cells are regulated by detoxification of the reactive intermediate resulting from both cytochrome P-450- and aldo-keto-reductase-mediated metabolism by a lung-specific GST. As benzo[a]pyrene is a significant lung carcinogen and it is present in tobacco smoke, GSTs are monitored as biomarkers of the effects of flaxseed in smokers.

Data Analysis:

A large pool of cDNA derived from buccal swabs of 5 normal, non-smoking volunteers is made to be used as the "baseline" comparator for all analyses. The cDNA from all trial samples is normalized to this pool using β-actin and GAPDH. Once normalized, each study sample is compared to the baseline comparator and the percent or fold-change is calculated. The primary analysis is to compare the change in gene expression before and after 3 weeks of SDG ingestion in the never smokers and current smokers (using the paired t-test). The values are also compared to the values in their placebo control samples. Additional analyses compare changes in expression with SDG across all time points, including the washout values (repeated measures ANOVA), and comparisons between non-smokers and smokers at baseline and after SDG and placebo. The 2 vs 3 week data and the 3 week vs the washout data is compared to establish the kinetics of response.

Figure 46:
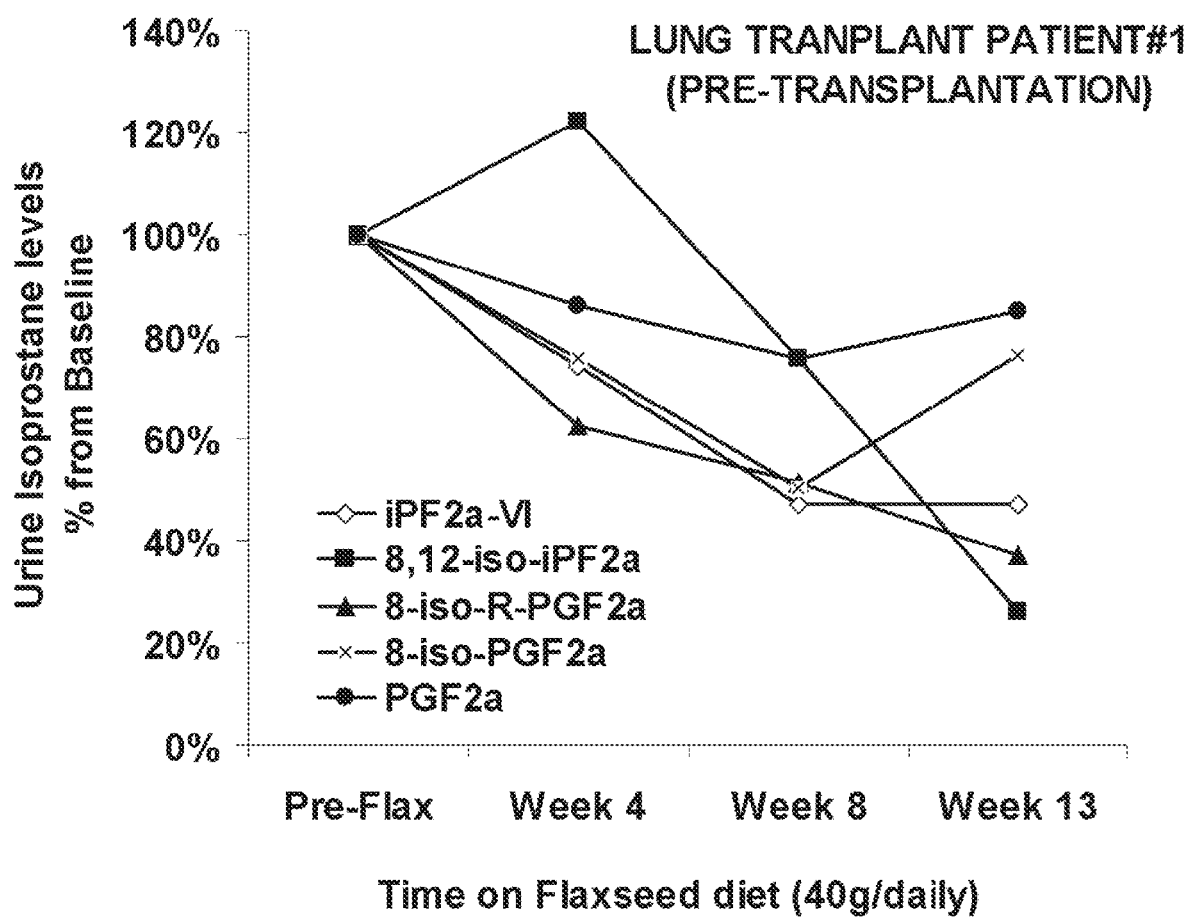
FIG. 46: Kinetics of urinary IsoP levels in one patient on FS.
Figure 47:
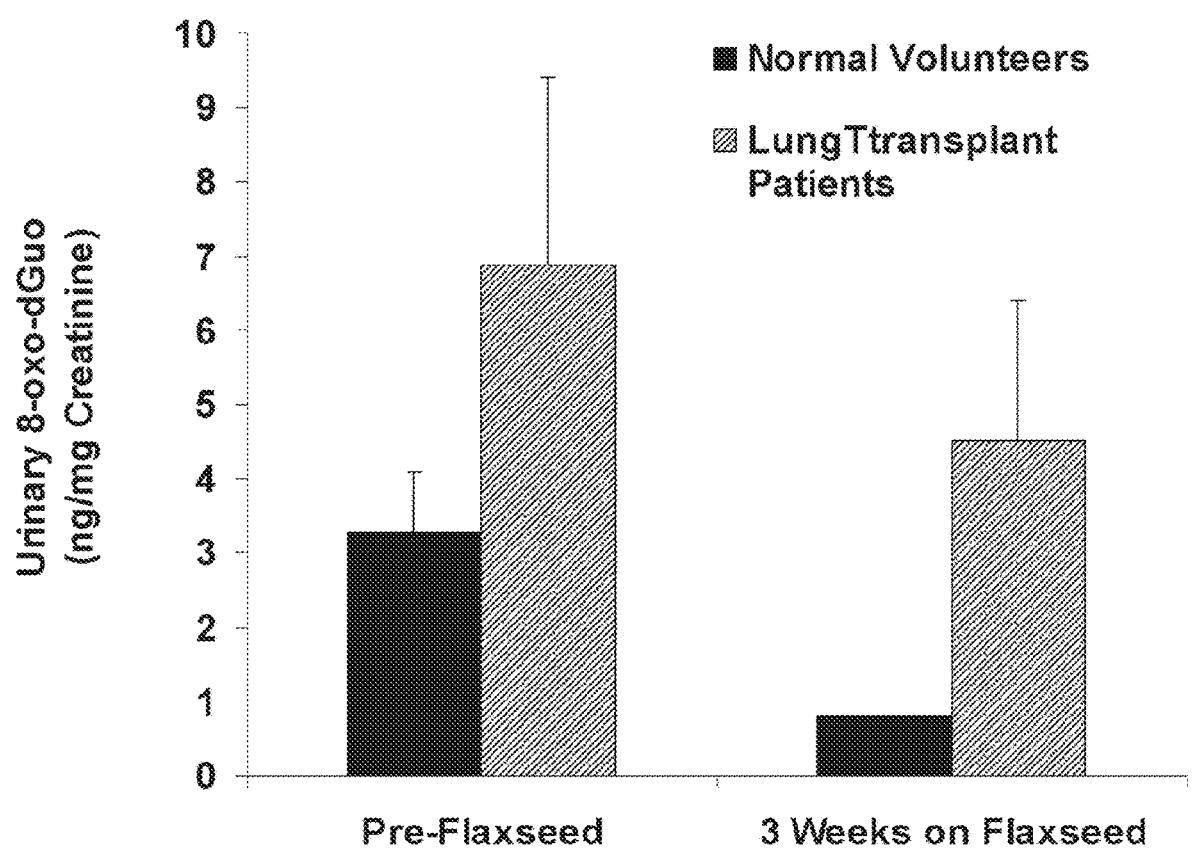
FIG. 47: Kinetics of urinary 8-oxo-dGuo levels in Normal and Lung transplant patients on FS.

Determination of Decreases in Oxidative Stress by SDG in the Same Patient Population Although it is difficult to measure oxidant stress in human subjects, one of the most established approaches is to measure urinary levels of IsoPs. Reliable and reproducible assays for this marker have been developed. Data was obtained from patients awaiting lung transplantation who ingested 40 g FS for up to 13 weeks. Urine IsoPs were found to steadily decline while on the FS, an indication of systemic lowering of oxidative stress (some IsoP subcategories ↓ down to 26% of the pre-FS level). Data for a representative patient are shown in FIG. 46. BaP, a carcinogen in cigarette smoke, causes reactive oxygen species-mediated DNA strand breaks and 8-oxo-7,8-dihydro-2'-deoxyguanosine ( 8-oxo-dGuo) formation. 8-oxo-dGuo can be detected in biological specimens (urine, liver, lung) using LC-MRM/ MS. Data from 2 human volunteers indicated that daily consumption of 40 g FS for 3 weeks induced a trend in decrease in 8-oxo-dGuo, a trend also seen in lung transplant patients (n=5) fed the same diet (FIG. 47).

Trial:

In the trial, urine samples are taken at multiple time points, in both the control and smoking subjects. Levels of urinary IsoPs and 8-oxo-dGuo are measured in a blinded fashion.

Exhaled Breath Condensate for Evaluating Lung Oxidative Stress:

Given that it is not feasible to perform invasive tests like bronchoscopy in these subjects, a non-invasive sample collection technique, exhaled breath condensate (EBC) is used for investigating lung oxidant stress. Many substances are found in expired breath that are detectable in the liquid that can be obtained by cooling (i.e., condensing) it. The advantages of this method are that it is non-invasive and convenient, as a non-invasive sampling method for the real-time analysis and evaluation of oxidative stress biomarkers in lung. Biomarkers of oxidative stress include: $H_2O_2$, isoprostanes (IsoPs), malondialdehyde, 4-hydroxy-2-nonenal, antioxidants, glutathione and nitrosative stress markers. Isoprostane levels in EBC are evaluated as a useful noninvasive approach to study the effect of FS on lung oxidative stress. 8-isoPs was measure from EBCs collected from control subjects and smokers. The levels in non-smokers were uniformly low—near the sensitivity of the test (1.2 pg/ml+/− 0.6, n=8), suggesting that EBC is not useful in non-smokers. Although levels were only measured in four smokers, interestingly, two of these subjects had much higher levels: 16 pg/ml and 6.5 pg/ml. Thus, in those smokers who have high baseline levels, EBC is used to follow lung specific oxidative stress.

Data Analysis.

The baseline value for each subject is determined and the change seen at end of treatment (3 weeks) is evaluated using a paired t-test. Additional analyses compare changes in expression with SDG across all time points, including the washout values (repeated measures ANOVA), and comparisons between non-smokers and smokers at baseline and after SDG. We can compare the 2 vs 3 week data and the 3 week vs the washout data to establish the kinetics of response.

The Chemopreventive Properties of the Flaxseed Lignan, SDG

In these experiments, the hypothesis that SDG can reduce the toxicities from xenobiotics and detoxify of carcinogens, such as BaP, similarly to Sulforaphane is tested. First, the in vitro effects of SDG on bronchial epithelial cells are evaluated. Cytotoxicity tests, such as MTT assay, are conducted for all SDG doses described below. Second, SDG given orally in the BaP mouse model is evaluated.

Evaluation of SDG-Mediated Detoxification of BaP in Normal Mouse and Human Primary Lung Epithelial Cells and Induction of Nrf2-Mediated, Phase II Enzyme Expression.

BaP (10 or 20 µM) induces ROS in a dose- and time-dependent manner when metabolically activated by epithelial cells (FIG. 23). For mouse studies, the immortalized C10 mouse bronchial cell line (derived from Balb/C mice) are used given that these cells are non-tumorigenic, contact-inhibited, and contain all the Nrf2-regulating machinery under investigation. Similar studies are performed using A549 cells (a transformed, but highly differentiated lung cancer cell line used to model human type 1 alveolar epithelial cells—see data in FIGS. 22-23, and importantly, primary human bronchial epithelial cells.

To evaluate direct ROS interception, a range of clinically-relevant, SDG concentrations (0.1-10 µM) is added at the same time as 10 µM B[a]P and is measured for decreases in $H_2DCF$ fluoresence, signifying direct anti-oxidant activity. Liquid chromatography/multiple reaction monitoring mass spectrometry (LC/MRM-MS) is also to determine the GSSG:GSH ratio. BaP can also quickly induce DNA adduct formation that can be measured using LC-MRM/MS (FIG. 22). BaP-induced oxidative DNA damage caused by BaP can be measured by 8-oxo-dGuo formation, tail moment of individual cells using standard COMET image analysis (data not shown), or densitometric analysis of immunoblots for the detection of γH2AX (data not shown). To evaluate DNA adduct and oxidative changes, a range of SDG concentrations is added at the same time as 10 µM B[a]P and these parameters are measured. Additionally, MTT cytotoxicity assays are performed to evaluate direct SDG effects on these cells in the absence and presence of the carcinogen (FS and FLC can only be tested in vivo). Next, the ability of the purified SDG to upregulate Phase II enzymes in bronchial epithelial cells is tested. Specifically, the induction of GST-Ya, and NQO-1 message and protein after 0, 1, 2, 4, 24, 48, and 72 hours of incubation with the lignan SDG (0.1-10 µM) treatment is measured. These enzymes are selected as characteristic representative ARE-regulated enzymes of the Phase II system. RT-PCR and immunoblot analyses are carried out. After identifying the time course of Phase II enzyme upregulation, the epithelial cells are pretreated with SDG, and at the time point of maximal Phase II induction BaP is added. Oxidant stress, DNA damage, and cell death is assessed using the assays described above.

Data Analysis, Expected Results and Additional Studies:

The first set of studies define the direct antioxidant effects of SDG. The second set of studies, performed at the later time points when the SDG itself is gone (thus no direct antioxidant effects present), define the effects of SDG due to its Phase II enzyme-inducing effects. Additional measurements of oxidative stress and inflammation are performed to determine the decrease by SDG of plasma oxidative stress measurements (plasma malondialdehyde) and pro-inflammatory stress markers such as (IL-6, IL-1α, IL1β, TNF-α, C-reactive protein).

The Chemopreventive Properties of SDG, in the Murine Model of A/J Mice-Chemical Carcinogen Induced Lung Tumorigenesis.

The effects of orally administered SDG on progression of BaP-induced carcinogenesis are studied in A/J mouse lung following the same study design described above (FIG. 42A, Plan A). The SDG supplemented mice are directly compared to control. Follow-up studies are performed including: studies using SDG during only the initiation phase (FIG. 42A, Plan B), and studies using SDG during only the promotion phase (FIG. 22A, Plan C).

Statistics:

The animal studies generally contain more than two groups (e.g. control vs. 50 mg/Kg SDG) of 20 mice and are analyzed using ANOVA or other suitable linear models. All calculations assume a two-sided test, an alpha level of 0.05, and at least 80% power.

TABLE 1

Mice on 3 test groups placed on 3 experimental plans (See FIG. 42A: Plans A, B, C) are sacrificed at 4, 6 and 9 months (3 time-points) i.e., 3 × 3 × 3 × 20 mice = 540 mice.

| Diet Groups | vehicle | BaP | Totals |
| --- | --- | --- | --- |
| Control (0) | 20 | 20 | 40 |
| 50 mg/Kg SDG | 20 | 20 | 40 |
| 100 mg/Kg SDG | 20 | 20 | 40 |
| TOTALS | 60 | 60 | 120 |

Example 8

Effects of SDG on Asbestos-Induced Carcinogenesis

SDG or flaxseed diets are hypothesized to decrease asbestos induced ROS/inflammation leading to: 1) ROS, 2) decreased cytokines; 3) decreased HMGB1; 4) less tumorigenic foci; and 5) less tumors. The underlining hypothesis is that decreased inflammation and oxidative stress will lead to decreased malignant transformation of cells and less tumor burden (see FIG. 48).

Figure 49:
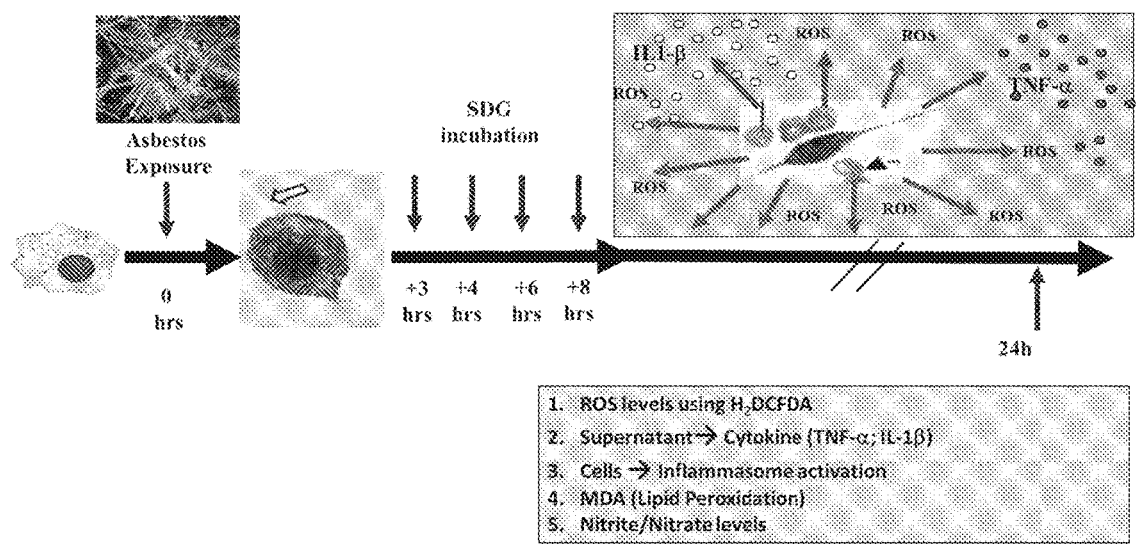
FIG. 49: Experimental plan (schematic) of asbestos exposure of cells to detect inflammatory cytokine secretion and nitrosative/oxidative stress.

To test the hypothesis that the flaxseed lignan SDG will decrease asbestos-induced inflammation, and oxidative and nitrosative stress, mouse peritoneal macrophages were exposed to varying concentrations of crocidolite asbestos fibers (10, 20, 30, and 40 ng/cm²). At variable times post asbestos exposure (3, 4, 6, and 8 hours), cells were incubated with SDG (50 µM) and supernatants collected 24 hours later to detect inflammatory cytokine secretion and nitrosative/oxidative stress (FIG. 49).

Figure 50:
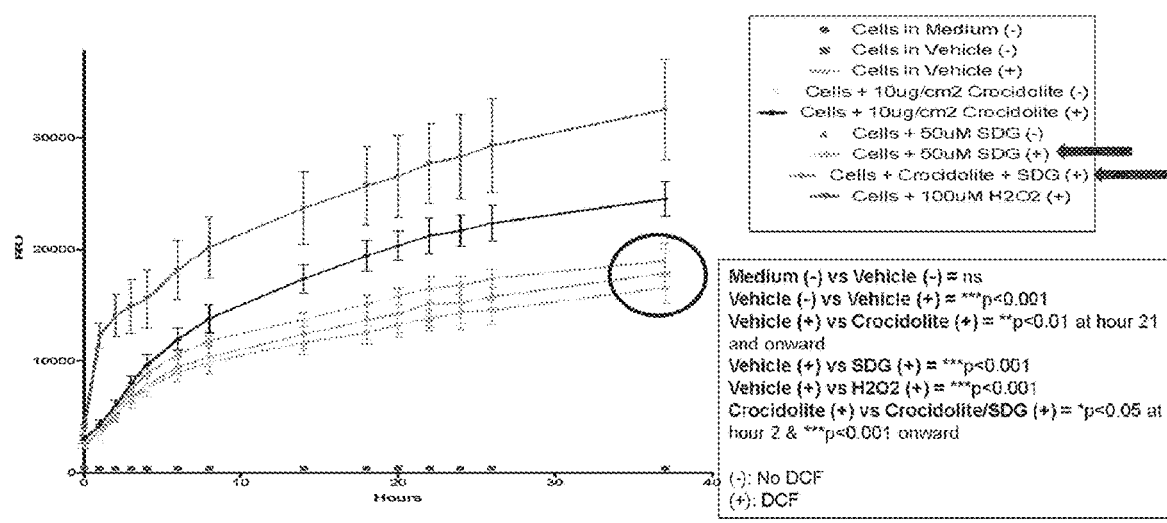
FIG. 50: SDG blunts asbestos-induced ROS secretion by human mesothelial cells in vitro.

SDG blunts asbestos-induced ROS secretion by human mesothelial cells in vitro (FIG. 50). Experimental plan for detecting asbestos-induced ROS in cells: (human mesothelial) HM cells or mouse macrophages plated in 20% DMEM for 24 hours; Added 20 µM DCF in HBSS for 1 hour; Supernatant replaced with 1% DMEM containing $H_2O_2$ (100 µM), asbestos (10 µg crocidolite/cm²) and/or SDG (50 µM); and Fluorescence level monitored up to 36 hours post-initiation of asbestos exposure. Results show that asbestos and $H_2O_2$ induce high levels of ROS, however addition of SDG in the medium significantly lowers ROS levels to baseline levels (FIG. 50).

Asbestos-Induced Oxidative Stress (ROS release) in Culture RAW Macrophages was evaluated. Cells were treated with the ROS-sensitive dye H2DCFDA for 30 min and then they were exposed to vehicle to 40 µg/cm2 asbestos fibers, or 4 uM hypochlorite solution and fluorescence intensity was measured spectrophotometrically for 90, 150 minutes and 27 hours. Asbestos-induced ROS was generated shortly post asbestos exposure and continued for the duration of the observation period (FIG. 51).

SDG given to macrophages several hours post exposure to asbestos decreases oxidative stress (FIGS. 52A-52B). Female C57/Bl6 mice were injected with 2 mL of thioglycollate and peritoneal macrophages harvested after 3 days. 2 million cells per well were plated in a 6 well plate and exposed to 20 µg/cm² asbestos. Cells were treated with 25 or 50 µM SDG (synthetic SDG) 3, 4, 6, or 8 hours post-asbestos exposure. Cells were harvested 24 hours post-asbestos exposure. Analysis performed on frozen supernatant samples. Results show that malondialdehyde, a marker for lipid peroxidation, increased over time with asbestos exposure (FIG. 52A). With 25 and 50 µM SDG added to the cells, the levels of MDA significantly decreased (p<0.05) (FIG. 52B).

Figure 53A:
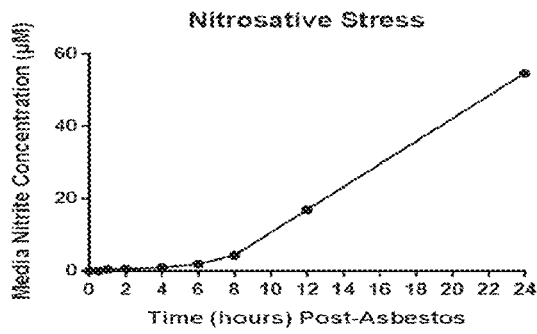
FIGS. 53A-53B: SDG given to macrophages several hours post exposure to asbestos decreases nitrosative stress.
Figure 53B:
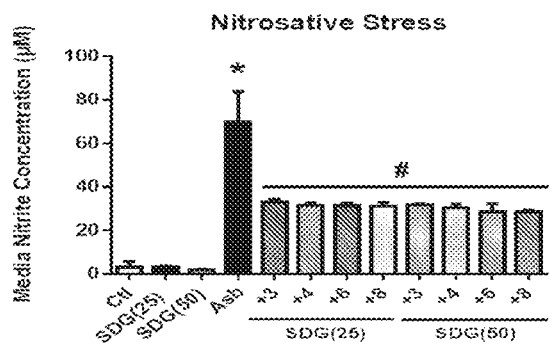

SDG Given to Macrophages Several Hours Post Exposure to Asbestos Decreases Nitrosative Stress (FIGS. 53A-53B). To evaluate of SDG in blunting nitrosative stress in cells post asbestos exposure, female C57/Bl6 mice were injected with 2 mL of thioglycollate and peritoneal macrophages harvested after 3 days. 2 million cells per well were plated in a 6 well plate and exposed to 20 µg/cm² asbestos. Cells were treated with 25 or 50 µM SDG (synthetic SDG) 3, 4, 6, or 8 hours post-asbestos exposure. Cells were harvested 24 hours post-asbestos exposure. Analysis performed on frozen supernatant samples. Results show that nitrite, a marker for nitrosative stress, increased over time with asbestos exposure (FIG. 53A). With 25 and 50 µM SDG added to the cells, the levels of MDA were significantly decreased (p<0.05) (FIG. 53B).

Figure 54A:
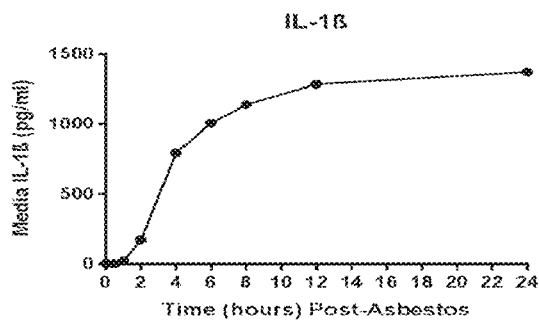
FIGS. 54A-54B: SDG given to macrophages several hours post exposure to asbestos decreases inflammatory cytokine secretion (IL-1β).
Figure 54B:
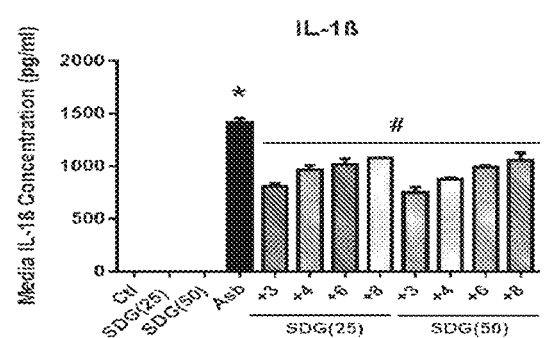

SDG Given to Macrophages Several Hours Post Exposure to Asbestos Decreases inflammatory cytokine secretion (IL-1β) (FIGS. 54A-54B). To evaluate SDG in blunting inflammatory cytokine secretion (IL-1β) in cells post asbestos exposure, female C57/Bl6 mice were injected with 2 mL of thioglycollate and peritoneal macrophages harvested after 3 days 2 million cells per well were plated in a 6 well plate and exposed to 20 µg/cm² asbestos. Cells were treated with 25 or 50 µM SDG (synthetic SDG) 3, 4, 6, or 8 hours post-asbestos exposure. Cells were harvested 24 hours post-asbestos exposure. Analysis performed on fresh supernatant samples. Results show that IL-1β, an pro-inflammatory cytokine, increased over time with asbestos exposure (FIG. 54A). With 25 and 50 µM SDG added to the cells, the levels of IL1β were significantly decreased (p<0.05) (FIG. 54B).

Figure 55A:
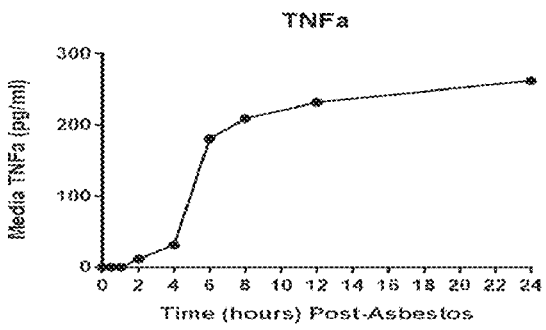
Figure 55B:
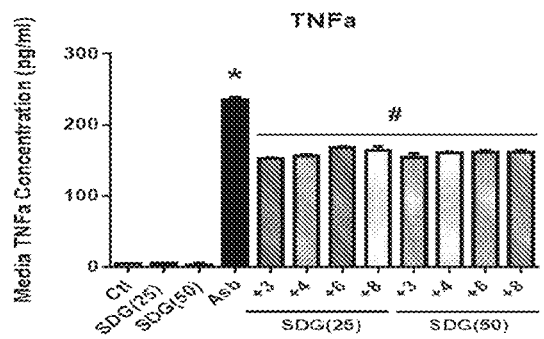

SDG Given to Macrophages Several Hours Post Exposure to Asbestos Decreases inflammatory cytokine secretion (TNF-α) (FIGS. 55A-55B). To evaluate SDG in blunting inflammatory cytokine secretion (TNF-α) in cells post asbestos exposure, female C57/Bl6 mice were injected with 2 mL of thioglycollate and peritoneal macrophages harvested after 3 days. 2 million cells per well were plated in a 6 well plate and exposed to 20 µg/cm² asbestos. Cells were treated with 25 or 50 µM SDG (synthetic SDG) 3, 4, 6, or 8 hours post-asbestos exposure. Cells were harvested 24 hours post-asbestos exposure. Analysis performed on fresh supernatant samples. Results show that TNF-α, an pro-inflammatory cytokine, increased over time with asbestos exposure (FIG. 55A). With 25 and 50 µM SDG added to the cells, the levels of TNF-α were significantly decreased (p<0.05) (FIG. 55B).

Briefly, the in vitro experiments in this Example demonstrate that (1) SDG blocks asbestos-induced ROS in human mesothelial cells and mouse RAW macrophages; (2) SDG blocks inflammatory cytokine secretion by mouse peritoneal macrophages exposed to asbestos; and (3) SDG blocks oxidative (lipid peroxidation) and nitrosative stress (nitrite levels) in mouse peritoneal macrophages exposed to asbestos. These in vitro experiments support in vivo experimentation to determine the usefulness of SDG in blunting chronic inflammation and ultimately malignancy due to asbestos exposure.

Figure 56:
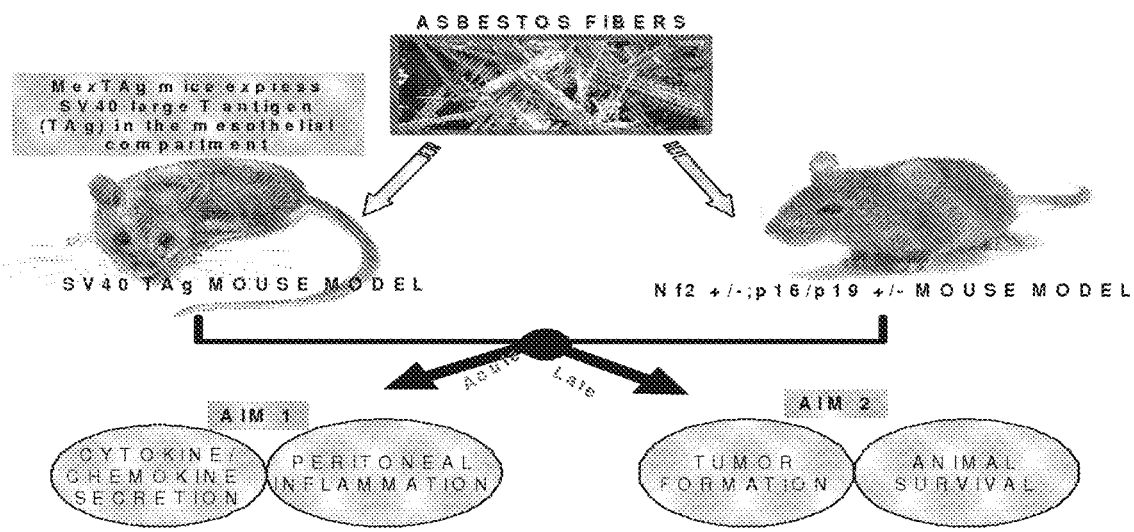
FIG. 56: Testing SDG in Asbestos-Induced Mesothelioma using two mouse models: Using at least 2 models of mice genetically predisposed to develop mesothelioma after asbestos exposure, we will: Evaluate the acute effects of Flaxseed and SDG on a single dose of asbestos in mice; test whether Flaxseed and SDG inhibits the development of tumors in genetic models of accelerated, asbestos induced MM.

Accordingly, SDG is tested in Asbestos-Induced Mesothelioma using two mouse models, where the mice are genetically predisposed to develop mesothelioma after asbestos exposure. Using these models, the acute effects of Flaxseed and SDG on a single dose of asbestos in these mice are evaluated, as well as testing whether Flaxseed and SDG inhibits the development of tumors in these models of accelerated, asbestos induced MM (FIG. 56).

Figure 57:
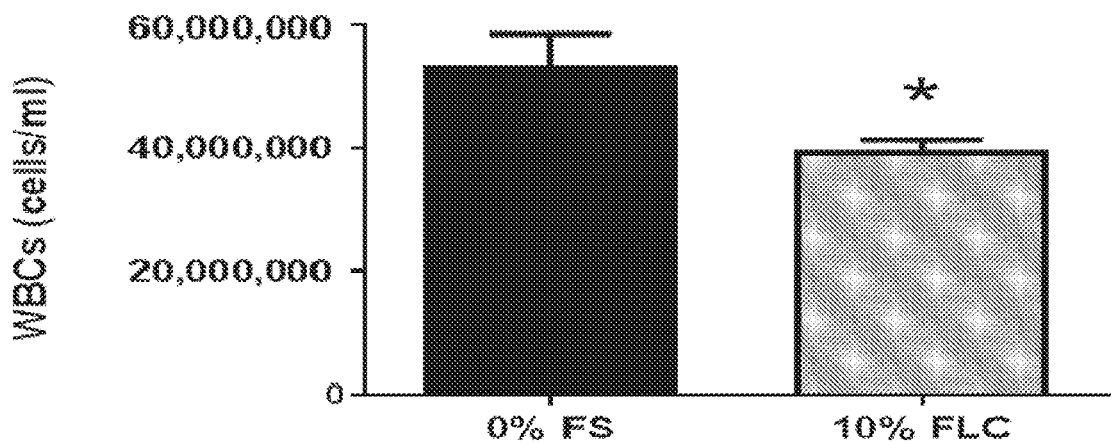
FIG. 57: FLC Diet Enriched in SDG (35% SDG) Given to MEXTAG Mice Exposed to Asbestos Decreased Inflammation.

SDG-enriched flaxseed lignan diet (FLC) blunts asbestos-induced abdominal inflammation in MEXTAG mice (FIG. 57). Briefly, 6 male MEXTAG mice (10-12 weeks old) were injected ip with 400 µg of crocidolite asbestos in a volume of 0.5 mL. Half the mice were placed on a FLC diet enriched in SDG (35% SDG) for two weeks prior to asbestos injection—the others were on standard diet. After 3 days, mice were lavaged with 5 mL of PBS and lavage taken for sups and cell counts. Cytospins were done and 3-5 separate fields were counted for differential—% of total cells were calculated. Compared to 0% FS fed mice, mice fed 10% FLC had a 26% reduction in abdominal lavage fluid WBCs (P=0.014) (FIG. 57).

Figure 58:
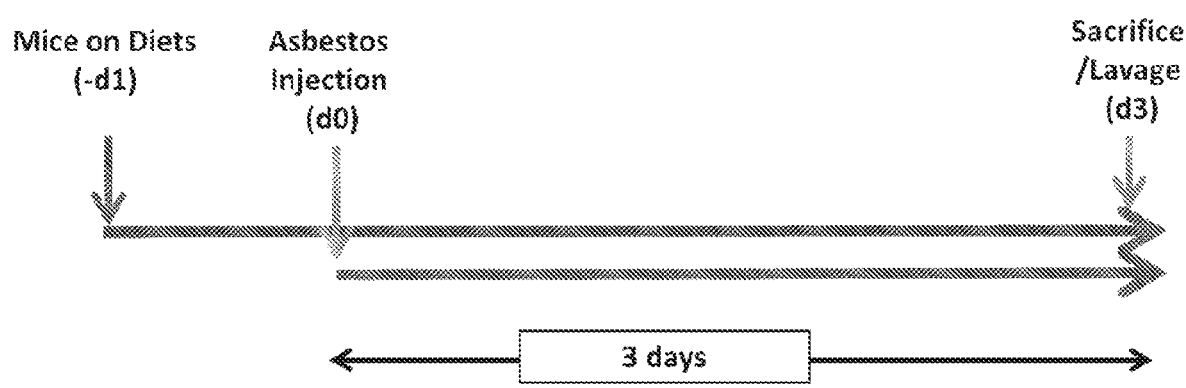
FIG. 58: Experimental Plan of asbestos exposure of NF2 mice and flaxseed/SDG lignan formulation evaluation.
Figure 59A:
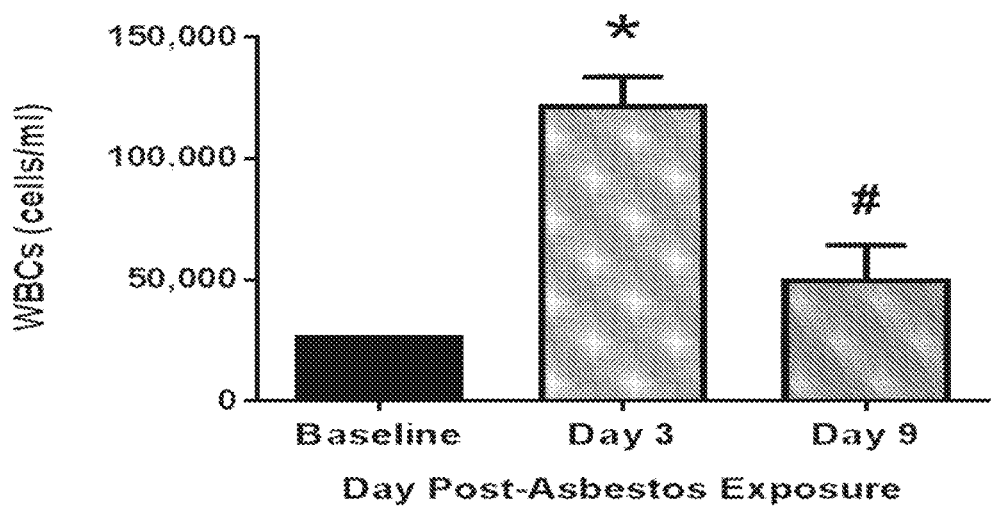
FIGS. 59A-59B: Kinetics of abdominal inflammation in NF2 mice post asbestos exposure: Inflammatory cell influx peaked by 3 days and tapered off by 9 days post asbestos exposure. Therefore, 3 days was selected as the time point to evaluate inflammation in all subsequent experiments.
Figure 59B:
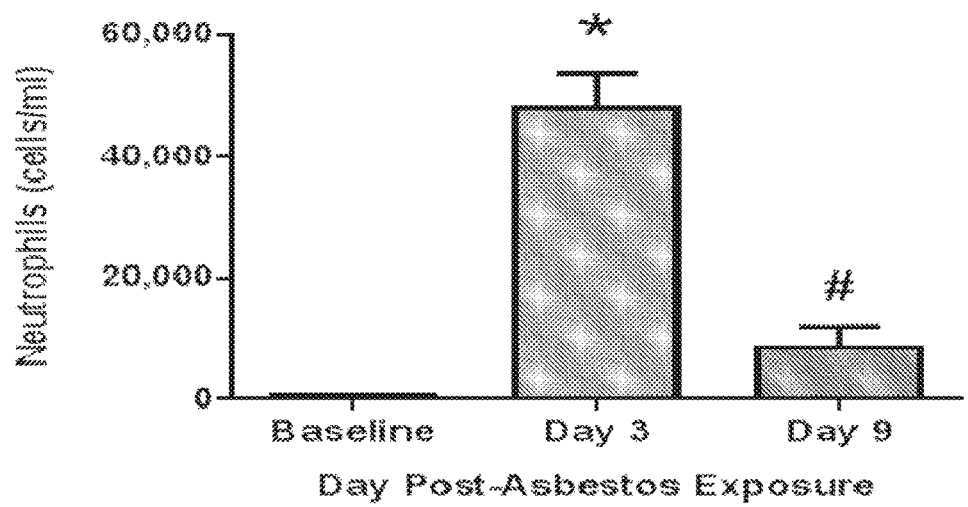

Acute phase studies in 7 week old, male NF2 (129sv) (+/−) mice exposed to asbestos were performed to evaluate the effects of flaxseed and lignan SDG formulations administered in diets. The experimental plan of asbestos exposure of NF2 mice and flaxseed/SDG lignan formulation evaluation is shown in FIG. 58. Briefly, Male NF2 (129SV) (+/−) were exposed to 400 µg asbestos via intraperitoneal injection on Day 0. Mice were initiated on the test diets (0% FS, 10% FS, 10% FLC; n=2 mice per group) 24 hours prior to asbestos exposure (Day −1) and sacrificed on Day 3 post-asbestos. Abdominal lavage (AL) was performed using 5 mL of 1×PBS. Inflammatory cell influx peaked by 3 days and tapered off by 9 days post asbestos exposure. Therefore, 3 days was selected as the time point to evaluate inflammation in all subsequent experiments (FIG. 59).

Figure 60A:
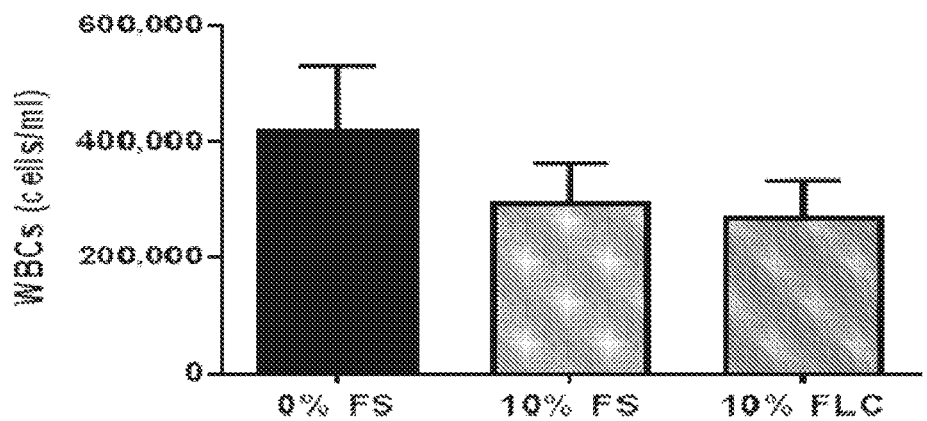
FIGS. 60A-60B: Flaxseed and its SDG-rich lignan component blunted asbestos-induced inflammation (younger mice): Total white blood cells (FIG. 60A) decreased with FS or FLC addition in the diet, albeit not significantly. However, when looking at cell differentials, and macrophage levels in particular, levels were significantly blunted by both flaxseed and the SDG-lignan diet (FIG. 60B).
Figure 60B:
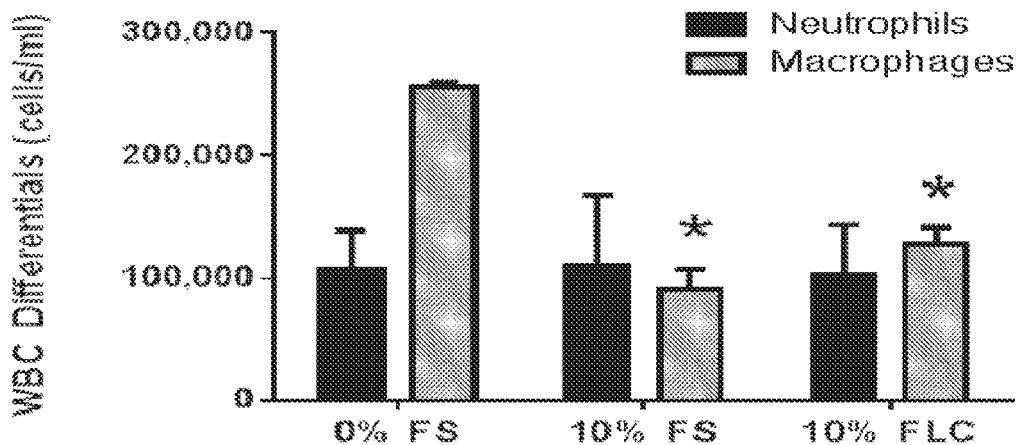

Flaxseed and its SDG-rich lignan component blunted asbestos-induced inflammation (younger mice) (FIGS. 60A-60B). Total white blood cells (FIG. 60A) decreased with FS or FLC addition in the diet, albeit not significantly. However, when looking at cell differentials, and macrophage levels in particular, levels were significantly blunted by both flaxseed and the SDG-lignan diet (FIG. 60B).

Figure 61A:
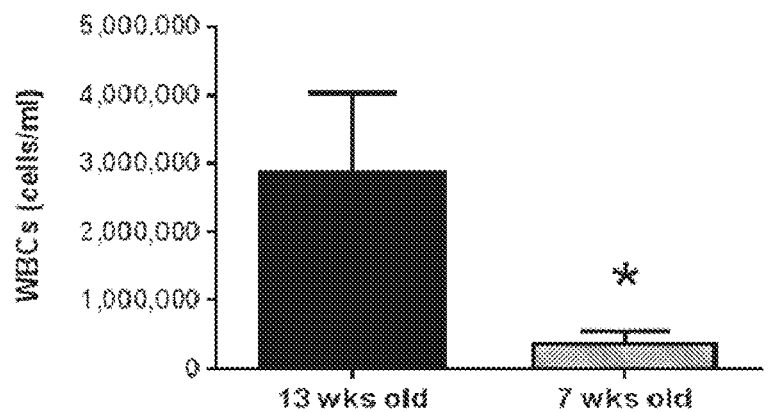
FIGS. 61A-61C: Flaxseed and its SDG-rich lignan component blunted asbestos-induced inflammation (older mice): Older mice exposed to abdominal asbestos (FIG. 61A) are more sensitive to asbestos by presenting with approx. 3,000,000 WBC/mL of abdominal lavage fluid as compared to just 300,000 cells/mL (10-fold higher). Results indicated that the inflammatory cells Neutrophils (FIG. 61B) and Macrophages (FIG. 61C) were both significantly higher in older than in younger mice.
Figure 61B:
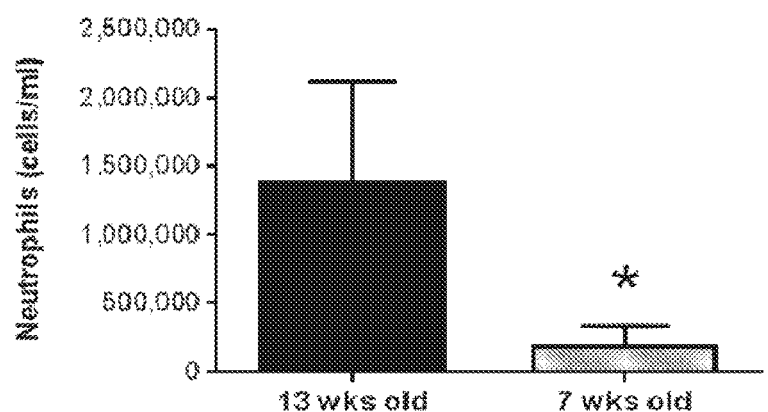
Figure 61C:
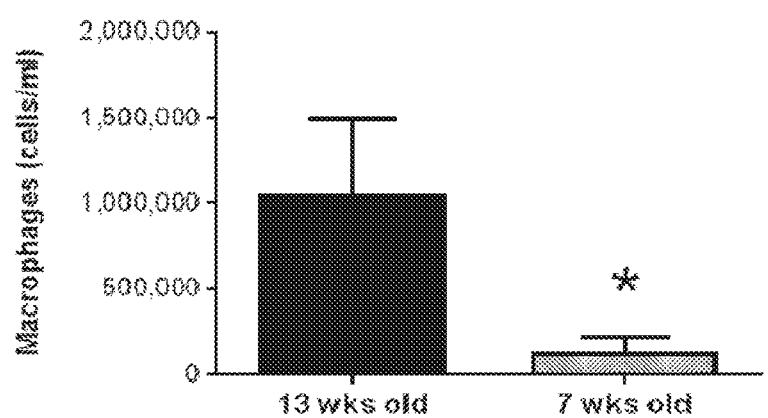

Flaxseed and its SDG-rich lignan component blunted asbestos-induced inflammation (older mice) (FIGS. 61A-61C). Older mice exposed to abdominal asbestos (FIG. 61A) are more sensitive to asbestos by presenting with approx. 3,000,000 WBC/mL of abdominal lavage fluid as compared to just 300,000 cells/mL (10-fold higher). Results indicated that the inflammatory cells Neutrophils (FIG. 61B) and Macrophages (FIG. 61C) were both significantly higher in older than in younger mice.

Figure 62A:
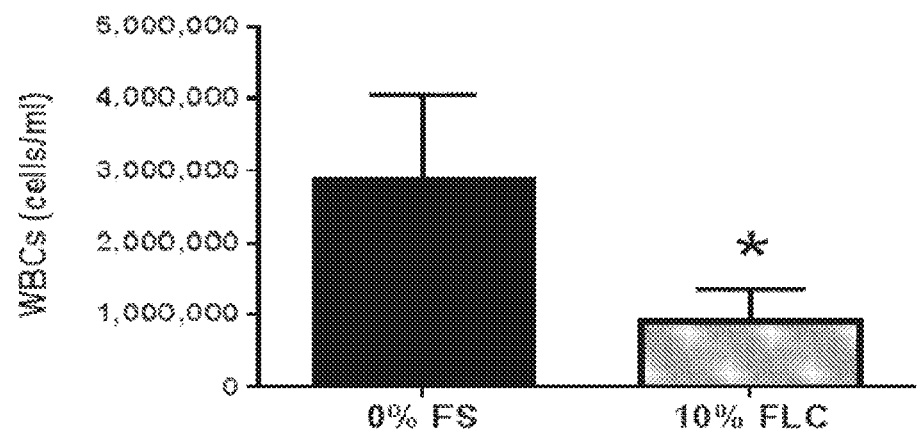
FIGS. 62A-B: Flaxseed lignan extract enriched in SDG (given in diet formulation) blunts asbestos inflammation in older mice: Male NF2 (129SV) (+/−) mice were injected (intraperitoneal) with 400 μg of asbestos on Day 0. Mice were initiated on the test diets (0% FS or 10% FLC) the week prior to asbestos exposure (Day-7) and sacrificed on Day 3 post-asbestos exposure. Abdominal lavage (AL) was performed with 5 mL 1×PBS (1 ml of belly lavage fluid was centrifuged and the supernatant was frozen). Plasma was collected at frozen at −80°. Cells were evaluated in lavage fluid and showed that total WBC and neutrophils, macrophages and eosinophils were all significantly decreased by the SDG-rich diet.
Figure 62B:
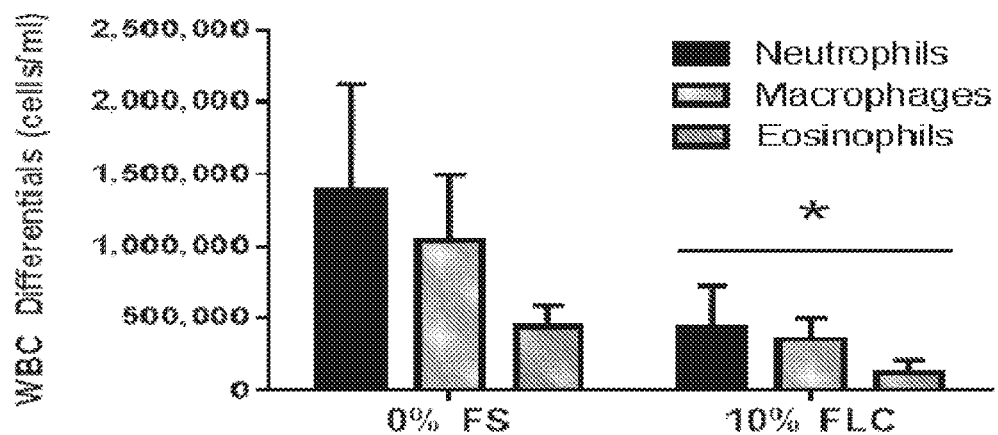

FIG. 62:

Flaxseed lignan extract enriched in SDG (given in diet formulation) blunts asbestos inflammation in older mice (FIG. 62). Male NF2 (129SV) (+/−) mice were injected (intraperitoneal) with 400 µg of asbestos on Day 0. Mice were initiated on the test diets (0% FS or 10% FLC) the week prior to asbestos exposure (Day −7) and sacrificed on Day 3 post-asbestos exposure. Abdominal lavage (AL) was performed with 5 mL 1×PBS (1 ml of belly lavage fluid was centrifuged and the supernatant was frozen). Plasma was collected at frozen at −80°. Cells were evaluated in lavage fluid and showed that total WBC and neutrophils, macrophages and eosinophils were all significantly decreased by the SDG-rich diet.

Figure 63A:
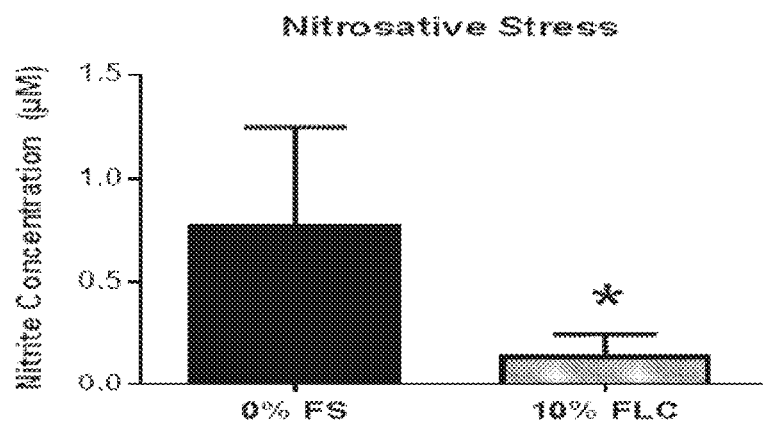
FIGS. 63A-C: Flaxseed lignan extract enriched in SDG (given in diet formulation) blunts asbestos inflammatory cytokine secretion and nitrosative stress in older mice: Male NF2 (129SV)(+/−) mice were injected (intraperitoneal) with 400 μg of asbestos on Day 0. Mice were initiated on test diets (0% FS or 10% FLC) the week prior to asbestos exposure (Day 7) and sacrificed on Day 3 post-asbestos exposure. Abdominal lavage (AL) was performed with 5 mL 1×PBS (1 mL of belly lavage fluid was centrifuged and the supernatant frozen). Plasma was collected at frozen at −80°. Levels of cytokines IL1β and TNFα as well as nitrites were significantly blunted by the SDG-rich diet.
Figure 63B:
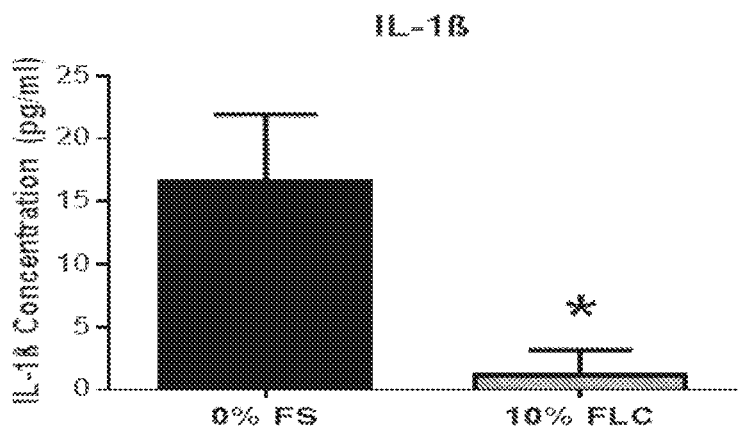
Figure 63C:
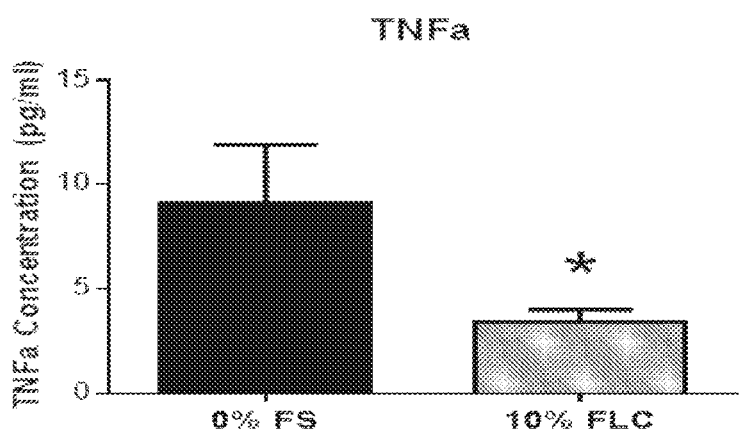

Flaxseed lignan extract enriched in SDG (given in diet formulation) blunts asbestos inflammatory cytokine secretion and nitrosative stress in older mice (FIG. 63). Male NF2 (1295V)(+/−) mice were injected (intraperitoneal) with 400 µg of asbestos on Day 0. Mice were initiated on test diets (0% FS or 10% FLC) the week prior to asbestos exposure (Day 7) and sacrificed on Day 3 post-asbestos exposure. Abdominal lavage (AL) was performed with 5 mL 1×PBS (1 mL of belly lavage fluid was centrifuged and the supernatant frozen). Plasma was collected at frozen at −80°. Levels of cytokines IL1β and TNFα as well as nitrites were significantly blunted by the SDG-rich diet.

Briefly, these in vivo experiments with NF2 mice demonstrate that (1) Mice fed SDG-enriched diet had significantly reduced abdominal inflammation, as determined by abdominal lavage fluid WBCs; (2) SDG-enriched diet reduced the number of neutrophils in abdominal lavage fluid; (3) Levels of pro-inflammatory cytokines, IL-1β and TNFα, were reduced in mice fed SDG-enriched; and (4) SDG-enriched diet-fed mice had lower levels of abdominal lavage fluid nitrite, indicative of reduced nitrosative stress induced by exposure to asbestos fibers.

These studies in these Examples demonstrate SDG's chemopreventive activity. Larger scale biomarker studies are conducted to evaluate the induction of Phase II enzymes in buccal epithelium and oxidative stress reduction by SDG. Additional measurements are performed measuring oxidative stress and inflammation after oral SDG daily administration in carcinogen exposed subjects, e.g. former or current smokers, and include plasma oxidative stress measurements (plasma malondialdehyde) and pro-inflammatory stress markers such as (IL-6, IL-1α, IL1β, TNF-α, C-reactive protein, F2-isoprostanes).

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A method for treating asthma in a subject in need thereof, the method comprising: administering to the subject a therapeutically effective amount of secoisolariciresinol diglucoside (SDG).

2. The method of claim 1, wherein the SDG is (S,S)-SDG.

3. The method of claim 1, wherein the SDG is (R,R)-SDG.

4. The method of claim 1, wherein the SDG is synthetic SDG.

5. The method of claim 1, wherein the SDG is administered in a dietary composition.

6. The method of claim 1, wherein administering comprises orally administering.

7. The method of claim 1, wherein the SDG is in a concentration about 1 nanomolar (nM) to about 1 molar (M).

8. The method of claim 7, wherein the SDG concentration is about 25 µM to about 250 µM.

9. The method of claim 1, wherein the subject is a human subject.

* * * * *